(12) United States Patent
Posner et al.

(10) Patent No.: US 7,166,585 B2
(45) Date of Patent: Jan. 23, 2007

(54) 24-SULFUR-SUBSTITUTED ANALOGS OF 1α,25-DIHYDROXY VITAMIN $D_3$

(75) Inventors: Gary H. Posner, Baltimore, MD (US); Kenneth Crawford, Decatur, GA (US); Hong Woon Yang, Baltimore, MD (US); HeungBae Jeon, Baltimore, MD (US); Mark Hatcher, Baltimore, MD (US); Byung-Chul Suh, Cockeysville, MD (US); Jay White, Newmarket (CA); Glenville Jones, Kingston (CA)

(73) Assignees: Cytochroma Inc., Ontario (CA); Johns Hopkins University, Baltimore, MD (US)

( * ) Notice: Subject to any disclaimer, the term of this patent is extended or adjusted under 35 U.S.C. 154(b) by 244 days.

(21) Appl. No.: 10/612,302

(22) Filed: Jul. 3, 2003

(65) Prior Publication Data

US 2004/0132695 A1    Jul. 8, 2004

Related U.S. Application Data

(63) Continuation-in-part of application No. 10/225,475, filed on Aug. 22, 2002, now abandoned.

(60) Provisional application No. 60/387,931, filed on Jun. 13, 2002, provisional application No. 60/328,429, filed on Oct. 12, 2001, provisional application No. 60/313,769, filed on Aug. 22, 2001.

(51) Int. Cl.
*A61K 31/593* (2006.01)
*C07C 401/00* (2006.01)
(52) U.S. Cl. ...................................... 514/167; 552/653
(58) Field of Classification Search ................ 552/653; 514/167
See application file for complete search history.

(56) References Cited

U.S. PATENT DOCUMENTS 4,927,815 A * 5/1990 DeLuca et al. ............. 514/167

OTHER PUBLICATIONS

Posner et al., "Conceptually New Sulfone Analogues of the Hormone 1alpha,25-Dihydroxyvitamin D3: Synthesis and Preliminary Biological Evaluation."*

* cited by examiner

*Primary Examiner*—Barbara P. Badio
(74) *Attorney, Agent, or Firm*—Rothwell, Figg, Ernst & Manbeck pc

(57) ABSTRACT

The present invention provides novel C24-sulfone analogs of 1α,25-dihydroxy vitamin $D_3$, compositions comprising these compounds and methods of using these compounds as selective inhibitors of CYP24. In particular, the compounds of the invention are useful for treating diseases which benefit from a modulation of the levels of 1α,25-dihydroxy vitamin $D_3$, for example, cell-proliferative disorders.

20 Claims, 11 Drawing Sheets

| Compound | $B_{50}$ (pg) |
|---|---|
| 1,25(OH)$_2$D$_3$ | 370 |
| KRC25SO$_2$PMP-1 | 20090 |
| KRC25SO$_2$PFP-1 | 30160 |
| KRC24SO$_2$Ph-1 | 12500 |

24-SULFUR-SUBSTITUTED ANALOGS OF 1α,25-DIHYDROXY VITAMIN D₃

CROSS REFERENCE TO RELATED APPLICATIONS

This application is a continuation-in-part of U.S. application Ser. No. 10/255,475 filed on Aug. 22, 2002, now abandoned, which claims the benefit under 35 USC § 119(e) from U.S. provisional patent application Ser. No. 60/313,769, filed Aug. 22, 2001; U.S. provisional patent application Ser. No. 60/328,429, filed Oct. 12, 2001; and U.S. provisional patent application Ser. No. 60/,387,931 filed on Jun. 13, 2002, the contents of which are incorporated herein by reference in their entirety.

GOVERNMENT RIGHTS STATEMENT

This invention was made with government support under NIH Grant Number CA 44530. The government has certain rights to this invention.

FIELD OF THE INVENTION

The present invention relates to novel analogs of the hormone 1α,25-dihydroxy vitamin D₃ that show selective inhibition of the enzyme CYP24 and which are low-calcemic, to pharmaceutical and diagnostic compositions containing them and to their medical use, particularly in the treatment and/or prevention of cancer, dermatological disorders, bone disorders, parathyroid disorders, wound healing, osteoporosis and autoimmune disorders.

BACKGROUND OF THE INVENTION

The vitamin D metabolic pathway is part of a vital endocrine system that is highly regulated at certain stages and produces metabolites that control the secretion of the parathyroid gland hormones (Beckman, M., and DeLuca, H. (1997) *Methods in Enzymol.* 282, 200–223; Jones, G., Strugnell, S., and DeLuca, H. (1998) *Physiol. Rev.* 78, 1193–1231). 1α,25-Dihydroxy vitamin D₃, also known as calcitriol (see below), a hormone produced in the vitamin D pathway, regulates phosphate and calcium levels in the blood which in turn control bone mass, the state of bones, and affects cellular differentiation in the skin and the immune system (Armbrecht, H. J., Okuda, K., Wongsurawat, N., Nemani, R., Chen, M., and Boltz, M. (1992) *J. Steroid Biochem. Molec. Biol.* 43, 1073–1081). In the vitamin D pathway, cytochrome P450s are enzymes that introduce functional groups by hydroxylation, usually at positions 1, 25, and 24, of vitamin D₃ (Beckman, M., and DeLuca, H. (1997) *Methods in Enzymol.* 282, 200–223).

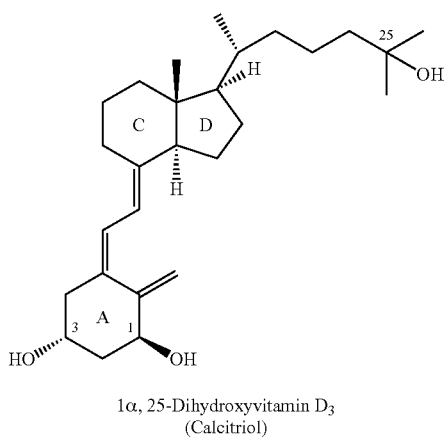

1α, 25-Dihydroxyvitamin D₃
(Calcitriol)

1α,25-Dihydroxy vitamin D₃ is converted to 1α,24,25-trihydroxy-D₃ by a mitochondrial P450 known as CYP24 (Bell, N. H., (1998) *J. Bone Miner. Res.* 13, 350–35211). CYP24 is induced by 1α,25-dihydroxy-D₃ and is found in the kidney as well as other vitamin D target tissues such as the parathyroid cells, keratinocytes, osteoblasts, and enteroctyes (Jones, G., Strugnell, S., and DeLuca, H. (1998) *Physiol. Rev.* 78, 1193–1231).

The biological effects of 1α,25-dihydroxy vitamin D₃ (calcitriol) and its synthetic analogs are mediated by the nuclear vitamin D receptor (VDR). Calcitriol has an important role in the antiproliferative and growth regulatory effects on normal and neoplastic cells (for e.g. prostate cancer cells). VDR ligands have potential widespread clinical application, however in many cases, hypercalcemia develops as a side effect which prevents sustained systemic administration. Inhibiting the catabolism of calcitriol and its analogs is expected to lengthen the biological lifetime of these compounds and thus to allow smaller amounts of them to be used for effective human chemotherapy. Such smaller dosing will avoid, or at least minimize, the hypercalcemic toxicity associated with medicinal use of these compounds. Further inhibition of the catabolism of 1α,25-dihydroxy vitamin D₃ increases the endogenous levels of this hormone, which will also have beneficial therapeutic effects.

There is a need for compounds that modulate the activity of CYP24, and therefore the levels of 1α,25-dihydroxy vitamin D₃ and analogs thereof.

SUMMARY OF THE INVENTION

It has been found that certain 24-sulfur-substituted analogs of 1α,25-dihydroxy vitamin D₃ show selective inhibition of the enzyme CYP24.

The present invention therefore provides compounds of Formula I, and pharmaceutically acceptable salts, hydrates, solvates and prodrugs thereof:

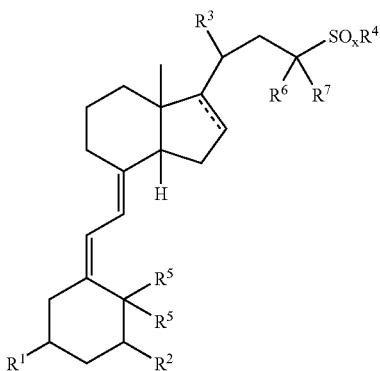

wherein
R¹ and R² are independently selected from the group consisting of OH, OC$_{1-4}$alkyl, and halo;
R³ is C$_{1-4}$alkyl;
R⁴ is selected from the group consisting of C$_{1-6}$alkyl, aryl and heteroaryl with both aryl and heteroaryl being unsubstituted or substituted with 1–5 groups independently selected from C$_{1-4}$alkyl, hydroxy-substituted C$_{1-6}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, CH=N—OC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;
R⁵ are either both H or together form =CH$_2$;
R⁶ and R⁷ are independently H, C$_{1-4}$alkyl or are taken together to form a C$_{3-6}$cyloalkyl ring;
x is 0–2; and
----- represents a single or a double bond.

In an embodiment, the present invention provides compounds of Formula I wherein the stereochemistry is that of natural 1α,25-dihydroxy vitamin D$_3$. Accordingly, the present invention relates to a compound of Formula I, and pharmaceutically acceptable salts, hydrates, solvates and prodrugs thereof, having the following relative stereochemistry:

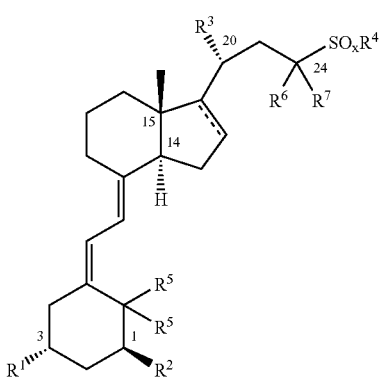

wherein
R¹ and R² are independently selected from the group consisting of OH, OC$_{1-4}$alkyl, and halo;
R³ is C$_{1-4}$alkyl;
R⁴ is selected from the group consisting of C$_{1-6}$alkyl, aryl and heteroaryl with both aryl and heteroaryl being unsubstituted or substituted with 1–5 groups independently selected from C$_{1-4}$alkyl, hydroxy-substituted C$_{1-6}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, CH=N—OC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;
R⁵ are either both H or together form =CH$_2$;
R6 and R⁷ are independently H. C$_{1-4}$alkyl or are taken together to form a C$_{3-6}$cyloalkyl ring;
x is 0–2; and
----- represents a single or a double bond.

In further embodiments of the invention, the compounds of Formula I are those where R⁴ is selected from unsubstituted and substituted aryl and heteroaryl. Accordingly, the present invention relates to a compound of Formula I, and pharmaceutically acceptable salts, hydrates, solvates and prodrugs thereof:

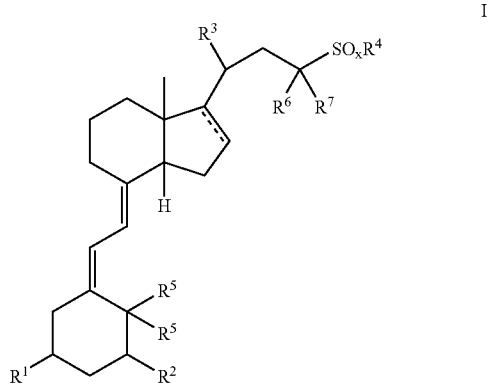

wherein
R¹ and R² are independently selected from the group consisting of OH, OC$_{1-4}$alkyl, and halo;
R³ is C$_{1-4}$alkyl;
R⁴ is selected from the group consisting of C$_{1-6}$alkyl, aryl and heteroaryl with both aryl and heteroaryl being unsubstituted or substituted with 1–5 groups independently selected from C$_{1-4}$alkyl, hydroxy-substituted C$_{1-6}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, CH=N—OC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;
R⁵ are either both H or together form =CH$_2$;
R6 and R⁷ are independently H. C$_{1-4}$alkyl or are taken together to form a C$_{3-6}$cyloalkyl ring;
x is 0–2; and
----- represents a single or a double bond.

In still further embodiments of the invention, the compounds of Formula I are those wherein R⁶ and R⁷ are H. Accordingly, the present invention relates to a compound of Formula I, and pharmaceutically acceptable salts, hydrates, solvates and prodrugs thereof:

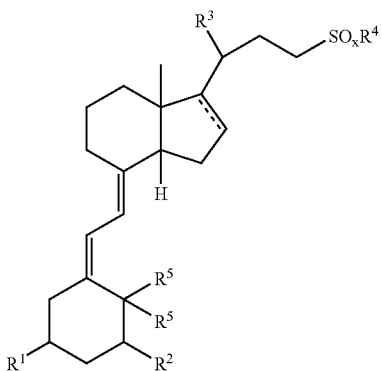

wherein $R^1$ and $R^2$ are independently selected from the group consisting of OH, $OC_{1-4}$alkyl, and halo;

$R^3$ is $C_{1-4}$alkyl;

$R^4$ is selected from the group consisting of $C_{1-6}$alkyl, aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, $CH=N-OC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;

$R^5$ are either both H or together form $=CH_2$;

$R^6$ and $R^7$ are independently H. $C_{1-4}$alkyl or are taken together to form a $C_{3-6}$cyloalkyl ring;

x is 0–2; and

-----represents a single or a double bond.

According to another aspect of the present invention, there is provided a pharmaceutical composition comprising a compound of the invention and a pharmaceutically acceptable carrier or diluent.

By selectively modulating CYP24, the enzyme that metabolizes 1α,25-dihydroxy vitamin $D_3$, the levels of 1α,25-dihydroxy vitamin $D_3$ (either endogenous or administered as part of a chemotherapeutic regimen), or an analog of 1α,25-dihydroxy vitamin $D_3$, will also be modulated. Diseases that benefit from a modulation of the levels of 1α,25-dihydroxy vitamin $D_3$ can therefore be treated using a modulator of CYP24. Further, by inhibiting the catabolism of 1α,25-dihydroxy vitamin $D_3$, the compounds of the invention will increase the endogenous levels of this hormone, which will result in similar beneficial therapeutic effects. By acting preferentially on CYP24, side effects caused by interaction with other enzymes and receptors will be reduced. Accordingly, the present invention provides a method for treating diseases which benefit from a modulation of the levels of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from a modulation of the levels of 1α,25-dihydroxy vitamin $D_3$, or an analog of 1α,25-dihydroxy vitamin $D_3$. Further, the invention includes a use of a compound of the invention to prepare a medicament to treat diseases which benefit from a modulation of the levels of 1α,25-dihydroxy vitamin $D_3$, or an analog of 1α,25-dihydroxy vitamin $D_3$.

Inhibition of CYP24 will inhibit the catabolism of 1α,25-dihydroxy vitamin $D_3$, or its analogs, which will lengthen the biological lifetime of these compounds and thus allow smaller amounts of them to be used for effective disease treatment. Such smaller dosing will avoid, or at least minimize, the hypercalcemic toxicity associated with medicinal use of 1α,25-dihydroxy vitamin $D_3$ and its analogs. Therefore, in an embodiment, the present invention provides a method for treating diseases which benefit from inhibiting the catabolism of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from inhibiting the catabolism of 1α,25-dihydroxy vitamin $D_3$, or an analog of 1α,25-dihydroxy vitamin $D_3$. Further, the invention includes a use of a compound of the invention to prepare a medicament to treat diseases which benefit from inhibiting the catabolism of 1α,25-dihydroxy vitamin $D_3$, or an analog of 1α,25-dihydroxy vitamin $D_3$.

Diseases which will benefit from a modulation in the levels of 1α,25-dihydroxy vitamin $D_3$ or its analogs, include, but are not limited to:

(i) in the parathyroid—hyper- and hypo-parathyroidism, Osudohypo-parathyroidism, Secondary hyperparathyroidism;

(ii) in the pancreas—diabetes;

(iii) in the thyroid—medullary carcinoma;

(iv) in the skin—psoriasis; wound healing;

(v) in the lung—sarcoidosis and tuberculosis;

(vi) in the kidney—chronic renal disease, hypophosphtatemic VDRR, vitamin D dependent rickets;

(vii) in the bone—anticonvulsant treatment, fibrogenisis imperfecta ossium, osteitits fibrosa cystica, osteomalacia, osteoporosis, osteopenia, osteosclerosis, renal osteodytrophy, rickets;

(viii) in the intestine—glucocorticoid antagonism, idopathic hypercalcemia, malabsorption syndrome, steatorrhea, tropical sprue; and (ix) autoimmune disorders.

In embodiments of the invention, the disease that benefits from a modulation in the levels of 1α,25-dihydroxy vitamin $D_3$, or an analog of 1α,25-dihydroxy vitamin $D_3$, are selected from cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation in the levels of 1α,25-dihydroxy vitamin $D_3$, or an analog of 1α,25-dihydroxy vitamin $D_3$, is a cell proliferative disorder. Accordingly, there is provided a method for modulating cell proliferation (preferably inhibiting cell proliferation) and/or for promoting cell differentiation, comprising administering an effective amount of a compound of the invention to a cell or animal in need thereof. The invention also includes a use of a compound of the invention to modulate cell proliferation (preferably to inhibit cell proliferation) and/or to promote cell differentiation. The invention further includes a use of a compound of the invention to prepare a medicament to modulate cell proliferation (preferably to inhibit cell proliferation) and/or to promote cell differentiation.

In another embodiment of the present invention, the disease that benefits from a modulation in the levels of 1α,25-dihydroxy vitamin D₃, or an analog of 1α,25-dihydroxy vitamin D₃, is cancer, Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention. In a further aspect, the invention provides a method of inhibiting CYP24 activity in a cell by administering an effective amount of a compound of the invention. The present invention also provides a use of a compound of the invention to modulate, preferably to inhibit, CYP24 activity. The present invention further provides a use of a compound of the invention to prepare a medicament to modulate CYP24 activity, preferably to inhibit CYP24 activity.

The compounds of the invention can be used alone or in combination with other agents that modulate CYP24 activity, or in combination with other types of treatment (which may or may not modulate CYP24) for diseases that benefit from a modulation in the levels of 1α,25-dihydroxy vitamin D₃, or an analog thereof, and/or an inhibition of the catabolism of 1α,25-dihydroxy vitamin D₃, or an analog thereof. Preferably the compounds of the invention are administered in combination with 1α,25-dihydroxy vitamin D₃ (calcitriol), an analog of 1α,25-dihydroxy vitamin D₃ or other vitamin D receptor agonists. Inhibiting catabolism of vitamin D receptor agonists such as 1α,25-dihydroxy vitamin D₃, or analogs thereof, will lengthen the biological lifetime or efficacy of these therapies and thus to allow smaller amounts of the drug to be used for effective human chemotherapy; such smaller dosing will avoid, or at least to minimize, the hypercalcemic toxicity associated with medicinal use of these compounds. The present invention therefore provides a method of increasing the efficacy of a vitamin D receptor agonist, preferably 1α,25-dihydroxy vitamin D₃, or an analog thereof, comprising co-administering an effective amount of a compound of the invention and an effective amount of the vitamin D receptor agonist, preferably 1α,25-dihydroxy vitamin D₃, or an analog thereof. Further the invention includes the use of a compound of the invention to increase the efficacy of a vitamin D receptor agonist, preferably 1α,25-dihydroxy vitamin D₃, or an analog thereof, and a use of a compound of the invention to prepare a medicament to increase the efficacy of a vitamin D receptor agonist, preferably 1α,25-dihydroxy vitamin D₃, or an analog thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Definitions

Figure 1:
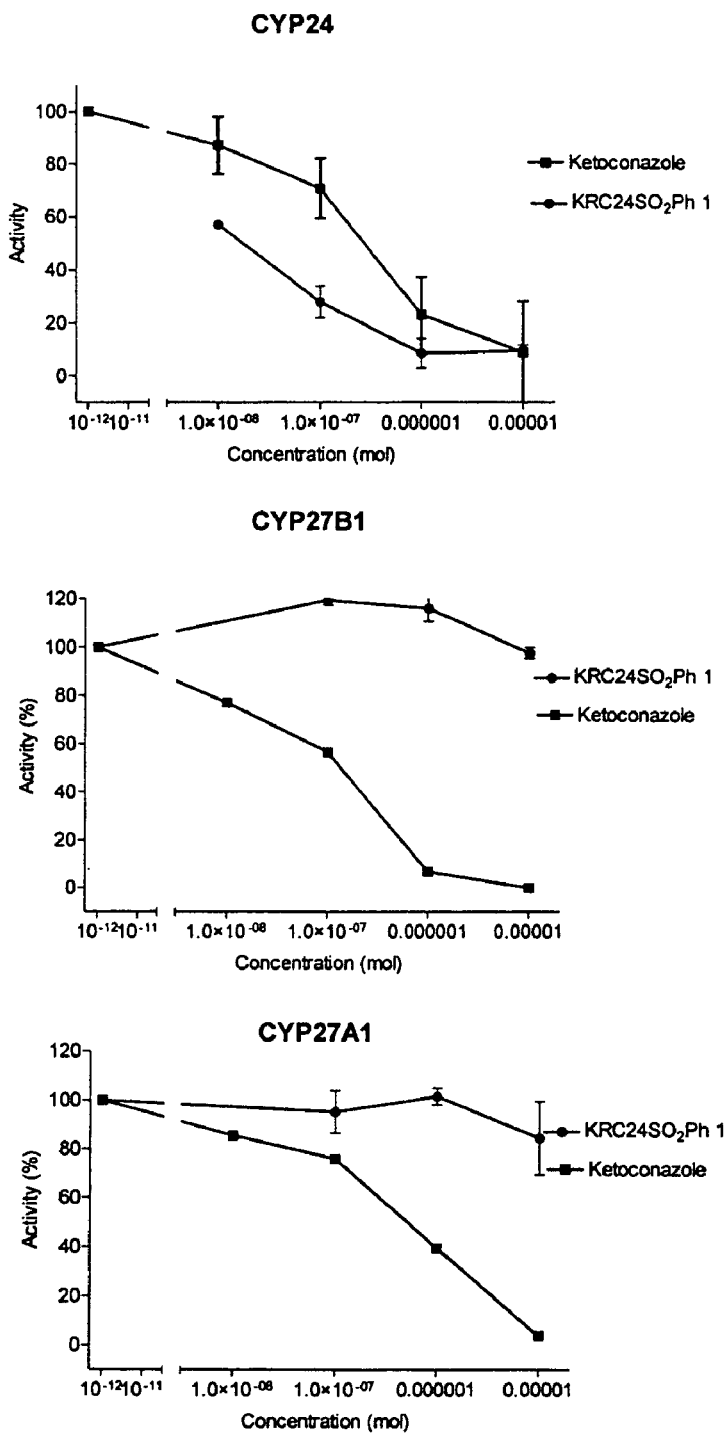
FIG. 1A is a graph showing the inhibition of CYP24 activity by compound I(a) (indicated as KRC24SO₂Ph-1) compared to ketoconazole.
FIG. 1B is a graph showing the inhibition of CYP27B1 activity by compound I(a) (indicated as KRC24SO₂Ph-1) compared to ketoconazole.
FIG. 1C is a graph showing the inhibition of CYP27A1 activity by compound I(a) (indicated as KRC24SO₂Ph-1) compared to ketoconazole.

The term "$C_{1-4}$alkyl" as used herein means straight and/or branched chain alkyl groups containing from one to four carbon atoms and includes methyl, ethyl, propyl, isopropyl, t-butyl and the like.

The term "hydroxy-substituted $C_{1-4}$alkyl" as used herein means straight and/or branched chain alkyl groups containing from one to four carbon atoms and substituted with 1–2 hydroxyl groups and includes hydroxymethyl, 1-hydroxyethyl, 2-hydroxyl-2-propyl and the like.

The term "$C_{1-4}$alkoxy" as used herein means straight and/or branched chain alkoxy groups containing from one to four carbon atoms and includes methoxy, ethoxy, propyoxyl, isopropyloxy, t-butoxy and the like.

The term "$C_{3-6}$cycloalkyl" as used herein means a 3- to 6-membered saturated carbocyclic ring.

The term "aryl" as used herein means unsubstituted or substituted mono- or bicyclic aromatic groups containing from 6 to 10 carbon atoms and includes phenyl and naphthyl and the like.

The term "heteroaryl" as used herein means unsubstituted or substituted mono- or bicyclic heteroaromatic groups containing from 5 to 10 atoms, of which 1–3 atoms may be a heteroatom selected from the group consisting of S, O and N, and includes furanyl, thienyl, pyrrolo, pyridyl, indolo, benzofuranyl and the like.

The term "halo" as used herein means halogen and includes chloro, flouro, bromo, iodo and the like.

As to any of the above groups that contain one or more substituents, it is understood, of course, that such groups do not contain any substitution or substitution patterns which are sterically impractical and/or synthetically non-feasible.

The term "pharmaceutically acceptable" as used herein means to be compatible with the treatment of animals, in particular humans.

The term "pharmaceutically acceptable salt" means an acid addition salt or a basic addition salt which is suitable for or compatible with the treatment of animals, in particular humans.

The term "pharmaceutically acceptable acid addition salt" as used herein means any non-toxic organic or inorganic salt of any base compound of the invention, or any of its intermediates. Basic compounds of the invention that may form an acid addition salt include those where $R^4$ is substituted with a group having a basic nitrogen, for example $NH_2$ and $NHC_{1-4}$alkyl. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the invention are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the invention, for laboratory use, or for subsequent conversion to a pharmaceutically acceptable acid addition salt.

The term "pharmaceutically acceptable basic addition salt" as used herein means any non-toxic organic or inorganic base addition salt of any acid compound of the invention, or any of its intermediates. Acidic compounds of the invention that may form a basic addition salt include those where $R^4$ is substituted with a group having acidic hydrogen, for example C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art.

The term "solvate" as used herein means a compound of the invention, or a pharmaceutically acceptable salt of a compound of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

The term "compound(s) of the invention" as used herein means compound(s) of Formula I, and salts, hydrates, solvates and prodrugs thereof.

The term an "effective amount" or a "sufficient amount" of an agent as used herein is that amount sufficient to effect beneficial or desired results, including clinical results, and, as such, an "effective amount" depends upon the context in which it is being applied. For example, in the context of administering an agent that modulates CYP24 activity, an effective amount of an agent is, for example, an amount sufficient to achieve such a modulation in CYP24 activity as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "modulate" as used herein includes the inhibition or suppression of a function or activity (such as CYP24 activity) as well as the enhancement of a function or activity.

To "inhibit" or "suppress" or "reduce" a function or activity, such as CYP24 activity, is to reduce the function or activity when compared to otherwise same conditions except for a condition or parameter of interest, or alternatively, as compared to another conditions.

The term "animal" as used herein includes all members of the animal kingdom including human. The animal is preferably a human.

The term "a cell" as used herein includes a plurality of cells. Administering a compound to a cell includes in vivo, ex vivo and in vitro treatment.

The term "cancer" as used herein includes all forms of cancer or neoplastic disease.

The term "1α,3β-stereochemistry" as used herein refers to the relative configuration of the groups, $R^1$ and $R^2$, in which $R^2$ is above the plane of the page, and the $R^1$ is below the plane of the page. The term "1β,3α-stereochemistry" as used herein refers to the relative configuration of the groups, $R^1$ and $R^2$, in which $R^1$ is above the plane of the page, and the $R^2$ is below the plane of the page.

II. Compounds of the Invention

Novel compounds showing selective inhibition of the enzyme CYP24 have been prepared. As such, the compounds of the invention are useful for modulating CYP24 activity and to treat diseases or disorders which benefit from such a modulation.

Accordingly, the present invention provides compounds of Formula I, and pharmaceutically acceptable salts, hydrates, solvates and prodrugs thereof:

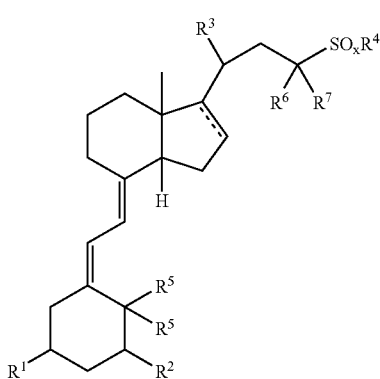

I wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of $C_{1-6}$alkyl, aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$, CN, C(O)OH, $C(O)OC_{1-4}$alkyl, $C(O)NHC_{1-4}$alkyl, CH=N—$OC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;

$R^5$ are either both H or together form =$CH_2$;
$R^6$ and $R^7$ are independently H. $C_{1-4}$alkyl or are taken together to form a $C_{3-6}$cyloalkyl ring;
x is 0–2; and
----represents a single or a double bond.

The compounds of Formula I include those in which $R^1$ and $R^2$ are independently selected from the group consisting of OH, $OC_{1-4}$alkyl, and halo. In embodiments of the invention, $R^1$ and $R^2$ are independently selected from the group consisting of OH, $OCH_3$, and fluoro. In a further embodiment, $R^1$ and R are both OH.

The present invention includes compounds of Formula I wherein $R^3$ is $C_{1-4}$alkyl. In embodiments of the invention, $R^3$ is $CH_3$.

The present invention includes compounds of Formula I wherein $R^4$ is selected from the group consisting of $C_{1-6}$alkyl, aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$, CN, C(O)OH, $C(O)OC_{1-4}$alkyl, $C(O)NHC_{1-4}$alkyl, CH=N—$OC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. In embodiments of the invention, $R^4$ is selected from $C_{1-6}$alkyl, unsubstituted or substituted phenyl, pyridyl, thienyl, furanyl and pyrrolo. In further embodiments, $R^4$ is selected from $C_{1-4}$alkyl, unsubstituted or substituted phenyl. In still further embodiments of the present invention, both aryl and heteroaryl may be either unsubstituted or substituted with 1–3 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$, CN, C(O)OH, $C(O)OC_{1-4}$alkyl, CH=N—$OC_{1-4}$alkyl, C(O)$NHC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$. Preferably the substituent is located at a position other than that ortho to the $SO_2$ group. In further embodiments, both aryl and heteroaryl may be either unsubstituted or substituted with 1–2 groups independently selected from methyl, 3-hydroxy-3-pentyl, methoxy, OH, $CF_3$, $OCF_3$, halo, $NH_2$, $NMe_2$ and CH=N—OMe. In further embodiments, both aryl and heteroaryl may be either unsubstituted or substituted with 1–2 groups independently selected from methyl, 3-hydroxy-3-pentyl, Cl, F and CH=N—OMe. In specific embodiments of the invention, $R^4$ is selected from the group consisting of methyl, ethyl, n-propyl, t-butyl, isopropyl, isobutyl, phenyl, 4-chlorophenyl, 3,4-dichloropheny, 4-fluorophenyl, 4-methylphenyl, 3,4-difluorophenyl, 4-(3-hydroxy-3-pentyl)phenyl, 4-(CH=N—OMe)phenyl, 4-methoxyphenyl, 4-trifluormethylpheny and 4-ntirophenyl. In more specific embodiments of the invention, $R^4$ is selected from the group consisting of t-butyl, isopropyl, phenyl, 4-chlorophenyl, 3,4-dichloropheny, 4-(3-hydroxy-3-pentyl)phenyl, 4-fluorophenyl and 4-methylphenyl.

The compounds of Formula I include those where $R^5$ are either both H or, together, $R^5$ form the group =$CH_2$.

The compounds of Formula I include those where $R^6$ and $R^7$ are independently H, $C_{1-4}$alkyl or are taken together to form a $C_{3-6}$cyloalkyl ring. In embodiments of the invention, $R^6$ and $R^7$ are independently H, methyl or are taken together to form a $C_{3-4}$cyloalkyl ring. In further embodiments of the invention, $R^6$ and $R^7$ are both H or are taken together to form a $C_{3-4}$cyloalkyl ring.

The present invention further includes compounds of Formula I wherein x is 0–2. In embodiments of the invention, x is 2.

The present invention also includes compounds of Formula I wherein ----- represents a single or a double bond. In an embodiment of the invention, ----- represents a single bond.

In further embodiments of the invention, the compounds of Formula I are those where $R^4$ is selected from unsubstituted and substituted aryl and heteroaryl. Accordingly, the present invention relates to a compound of Formula I, and pharmaceutically acceptable salts, hydrates, solvates and prodrugs thereof:

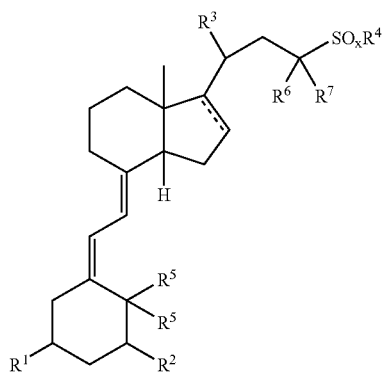

I wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of $C_{1-6}$alkyl, aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)$(C_{1-4}$alkyl), CN, C(O)OH, C(O)$OC_{1-4}$alkyl, C(O)$NHC_{1-4}$alkyl, CH=N—$OC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$;
$R^5$ are either both H or together form =$CH_2$;
$R^6$ and $R^7$ are independently H. $C_{1-4}$alkyl or are taken together to form a $C_{3-6}$cyloalkyl ring;
x is 0–2; and
----- represents a single or a double bond.

All of the compounds of Formula I have more than one asymmetric centre. Where the compounds according to the invention possess more than one asymmetric centre, they may exist as diastereomers. It is to be understood that all such isomers and mixtures thereof in any proportion are encompassed within the scope of the present invention. The stereochemistry of the compounds of the invention is preferably that of natural 1α,25-dihydroxy vitamin $D_3$. Therefore, in an embodiment, the present invention provides compounds of Formula I, and pharmaceutically acceptable salts, hydrates, solvates and prodrugs thereof, having the following relative stereochemistry:

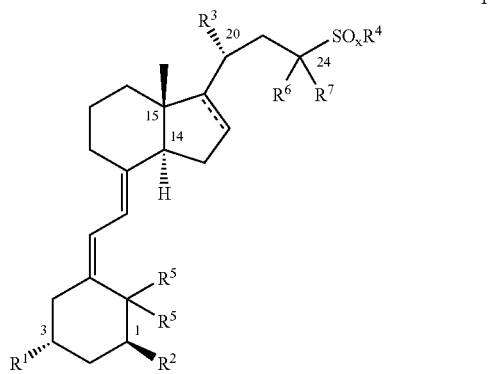

I wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of $C_{1-6}$alkyl, aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}$alkyl)$(C_{1-4}$alkyl), CN, C(O)OH, C(O)$OC_{1-4}$alkyl, C(O)$NHC_{1-4}$alkyl, CH=N—$OC_{1-4}$ alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$;
$R^5$ are either both H or together form =$CH_2$;
$R^6$ and $R^7$ are independently H. $C_{1-4}$alkyl or are taken together to form a $C_{3-6}$cyloalkyl ring;
x is 0–2; and
----- represents a single or a double bond.

When ----- is a single bond in the compounds of Formula I, it is an embodiment of the invention that the stereochemistry at carbon 17 is that of natural 1α,25-dihydroxy vitamin $D_3$ (i.e. R). It is to be understood that, while the relative stereochemistry of the compounds of Formula I is preferably as shown above, such compounds of Formula I may also contain certain amounts (e.g. less than 20%, preferably less than 10%, more preferably less than 5%) of compounds of Formula I having alternate stereochemistry. For example, a compound of Formula I having the 1α,3β-stereochemistry of natural 1α,25-Dihydorxy Vitamin $D_3$, shown above, may contain less then 20%, preferably less then 10%, more preferably less then 5%, of a compound of Formula I having the unnatural 1α,3α-sterochemistry.

In a further embodiment of the invention, the compounds of Formula I are those wherein $R^6$ and $R^7$ are H. Accordingly, the present invention relates to a compound of Formula I, and pharmaceutically acceptable salts, hydrates, solvates and prodrugs thereof:

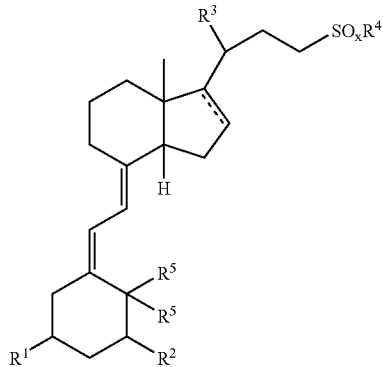

I wherein

R$^1$ and R$^2$ are independently selected from the group consisting of OH, OC$_{1-4}$alkyl, and halo;

R$^3$ is C$_{1-4}$alkyl;

R$^4$ is selected from the group consisting of C$_{1-6}$alkyl, aryl and heteroaryl with both aryl and heteroaryl being unsubstituted or substituted with 1–5 groups independently selected from C$_{1-4}$alkyl, hydroxy-substituted C$_{1-6}$alkyl, OC$_{1-4}$alkyl, OH, CF$_3$, OCF$_3$, halo, SH, SC$_{1-4}$alkyl, NH$_2$, NHC$_{1-4}$alkyl, N(C$_{1-4}$alkyl)(C$_{1-4}$alkyl), CN, C(O)OH, C(O)OC$_{1-4}$alkyl, C(O)NHC$_{1-4}$alkyl, CH═N—OC$_{1-4}$alkyl, NHC(O)C$_{1-4}$alkyl, OC(O)C$_{1-4}$alkyl, SOC$_{1-4}$alkyl, SO$_2$C$_{1-4}$alkyl, SO$_2$NHC$_{1-4}$alkyl and SO$_2$NH$_2$;

R$^5$ are either both H or together form ═CH$_2$;

x is 0–2; and

----- represents a single or a double bond.

In specific embodiments of the present invention, the compounds of Formula I are selected from the group consisting of:

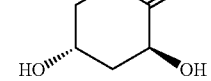

I(a)

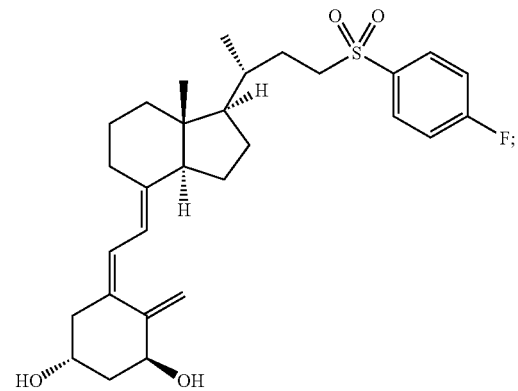

I(c)

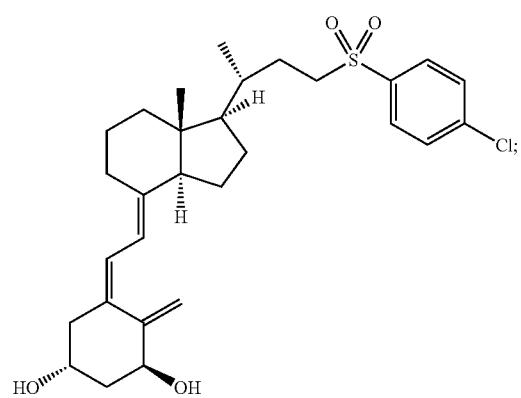

I(e)

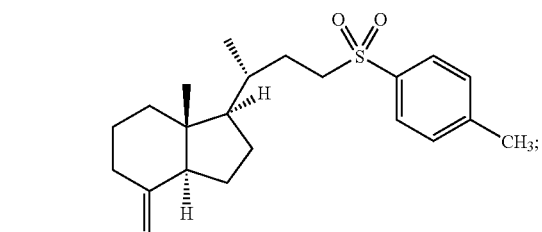

I(g)

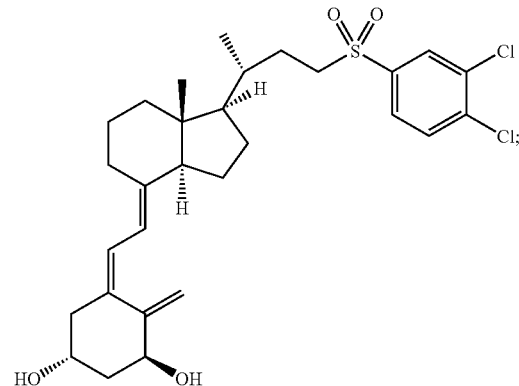

I(i)

I(k)
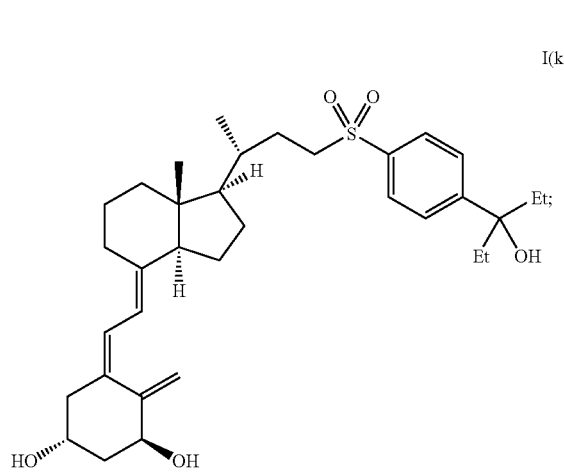
I(m)
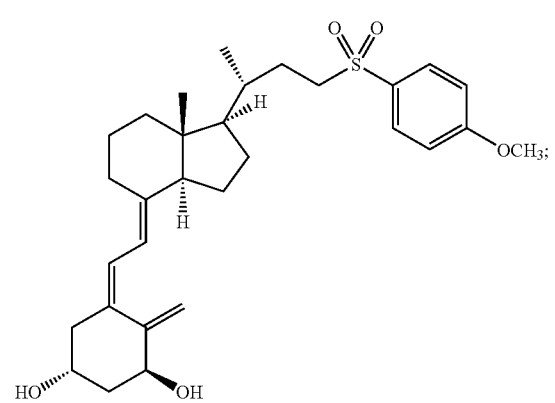
I(o)
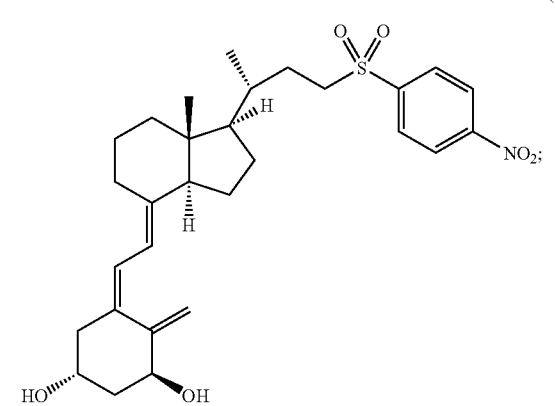
I(q)
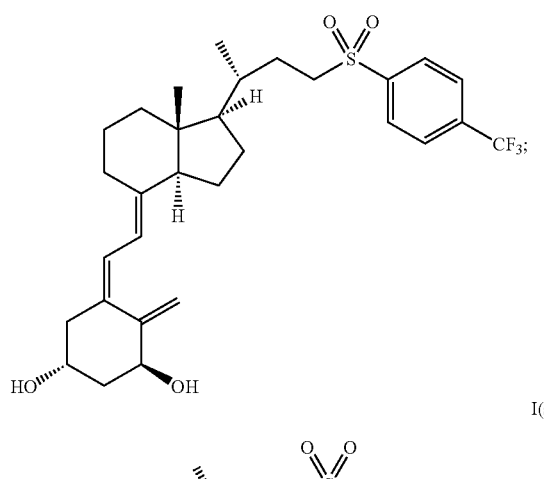
I(s)
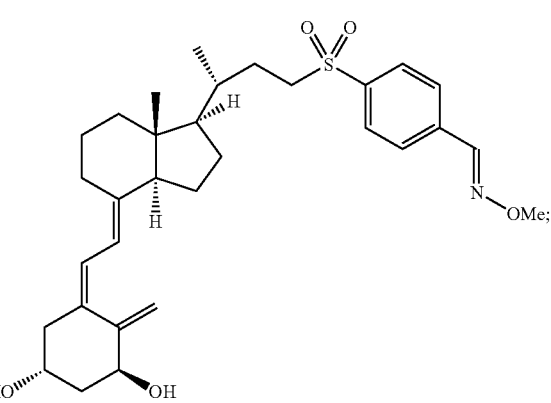
I(u)
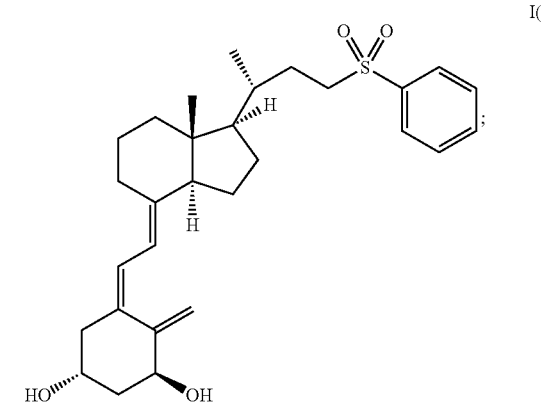
I(v)
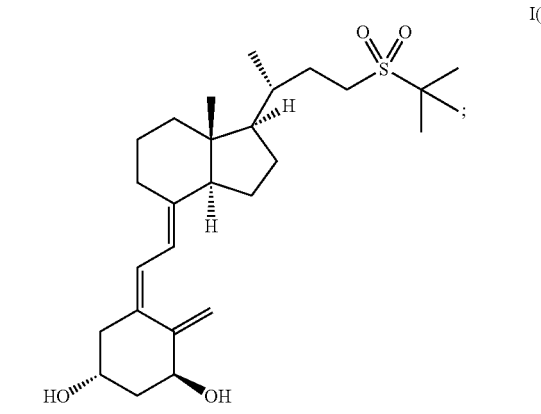

-continued
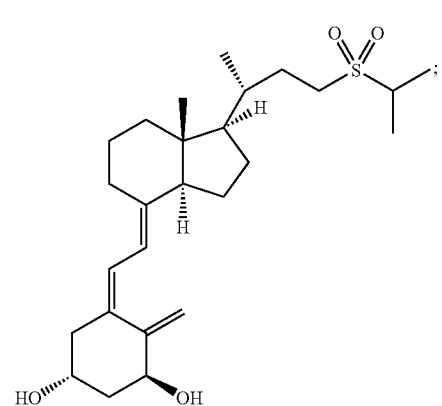
I(w)
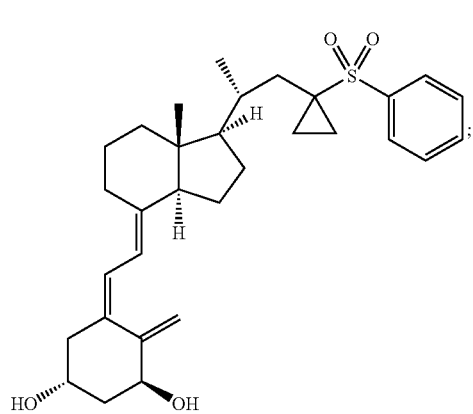
I(cc)
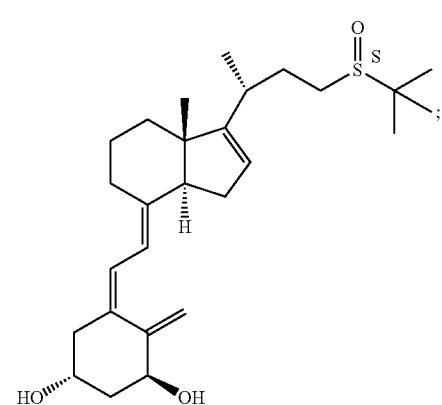
I(x)
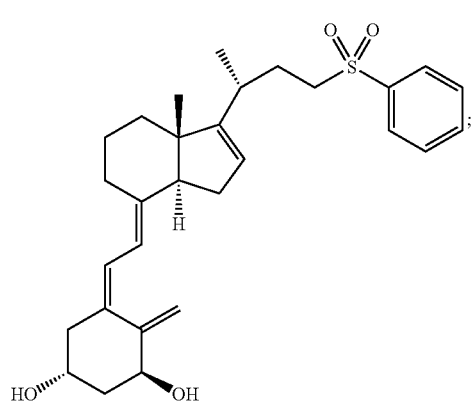
I(ee)
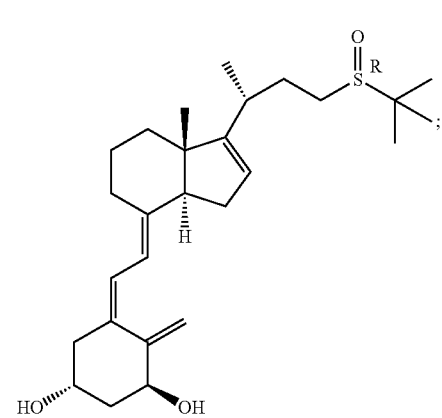
I(y)
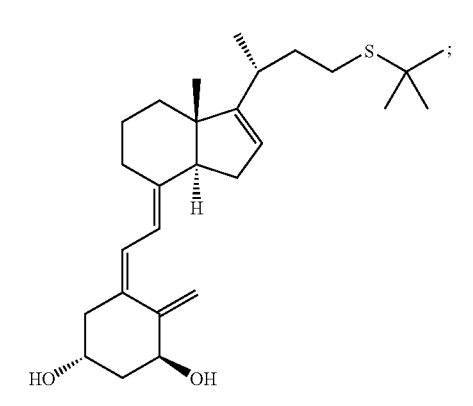
I(gg)
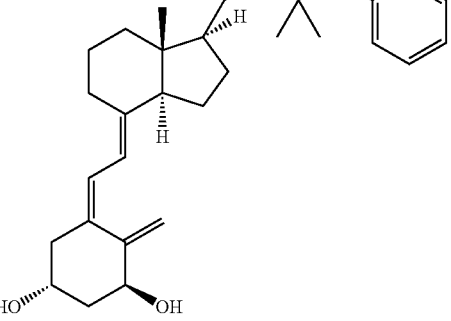
I(aa)
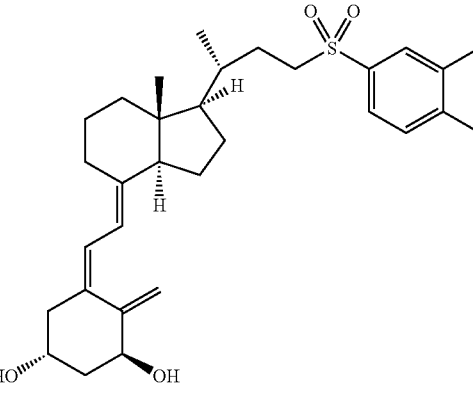
I(ii)

-continued

I(jj)
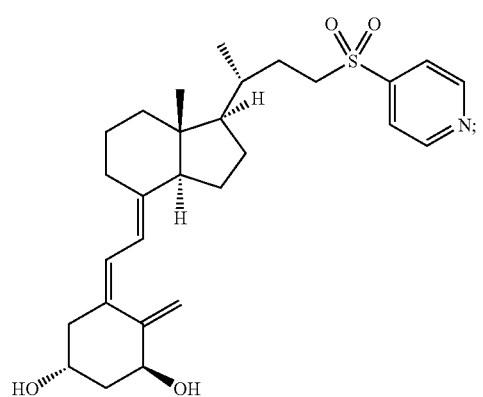

I(ll)
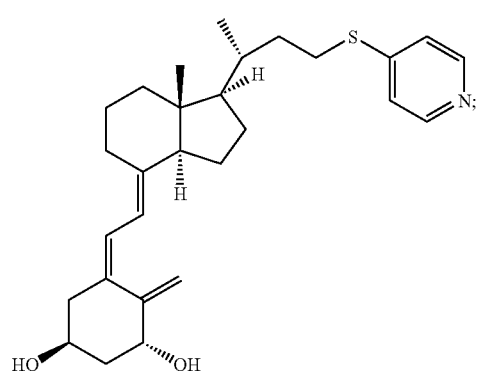

I(nn)
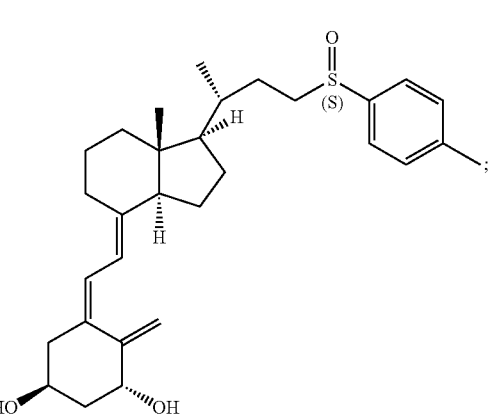

I(oo)
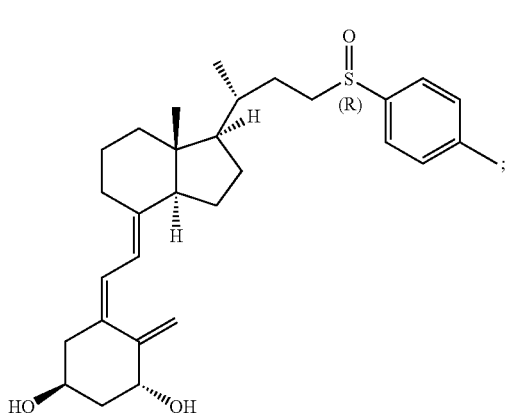

and pharmaceutically acceptable salts, hydrates, solvates and prodrugs thereof.

In embodiments of the invention the compound of Formula I is selected from the group consisting of I(a), I(c), I(e), I(g), I(i), I(k), I(m), I(o), I(q), I(s), I(u), I(aa), I(cc), I(ee), I(ii), I(jj), I(ll), I(nn) and I(oo), and pharmaceutically acceptable salts, hydrates, solvates and prodrugs thereof. In further embodiments of the invention, the compound of Formula I is selected from the group consisting of I(a), I(e), I(g), I(i), I(m), I(o), I(q), I(u), I(cc), I(ee), I(jj), I(ll), I(nn) and I(oo), and pharmaceutically acceptable salts, hydrates, solvates and prodrugs thereof. In still further embodiments of the invention, the compound of Formula I is selected from the group consisting of I(a), I(e), I(g), I(i), I(u), I(cc), I(ee), I(jj), I(nn) and I(oo), and pharmaceutically acceptable salts, hydrates, solvates and prodrugs thereof. In yet further embodiments of the present invention the compound of Formula I is selected from the group consisting of I(v), I(w), I(x), I(y) and I(gg), and pharmaceutically acceptable salts, hydrates, solvates and prodrugs thereof. In still further embodiments of the present invention the compound of Formula I is selected from the group consisting of I(v), I(w) and I(y), and pharmaceutically acceptable salts, hydrates, solvates and prodrugs thereof.

III. Methods of Preparing Compounds of the Invention

In accordance with another aspect of the present invention, the compounds of the invention can be prepared by processes analogous to those established in the art. Therefore, compounds of this invention may be prepared, for example, by the reaction sequence shown in Scheme 1:

Scheme 1

III

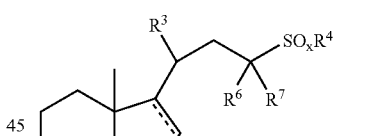

IV

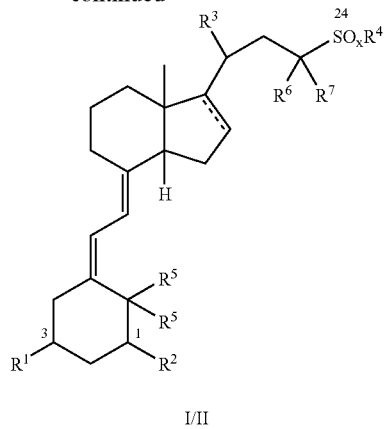

I/II

Ketones of Formula III, wherein $R^3$, $R^4$, $R^5$, $R^6$, x and ----- are as defined in Formulae I ad II, may be reacted with phosphine oxides of Formula IV, wherein $R^1$, $R^2$ and $R^5$ are as defined in Formula I, under standard Horner-Wadsworth-Emmons (HWE) coupling conditions. Therefore phosphine oxides IV, wherein $R^1$, $R^2$ and $R^5$ are as defined in Formula I, are treated with a strong base, for example an alkyl lithium such as n-butyl lithum, under anhydrous conditions in an inert atmosphere and solvent, for example tetrahydrofuran (THF), at temperatures in the range of about –60° C. to about –90° C., suitably at about –78° C. To the resulting intermediate ylide is added a cold, preferably at about –78° C., solution of a ketone III in an inert solvent such as THF while maintaining the anhydrous conditions. After removal of any protecting groups using standard chemistries (if needed), compounds of Formula I may be obtained.

Ketones of Formula III, wherein wherein $R^3$, $R^4$, $R^5$, $R^6$, x and ----- are as defined in Formula I, may be prepared, for example, as shown in Scheme 2:

Scheme 2

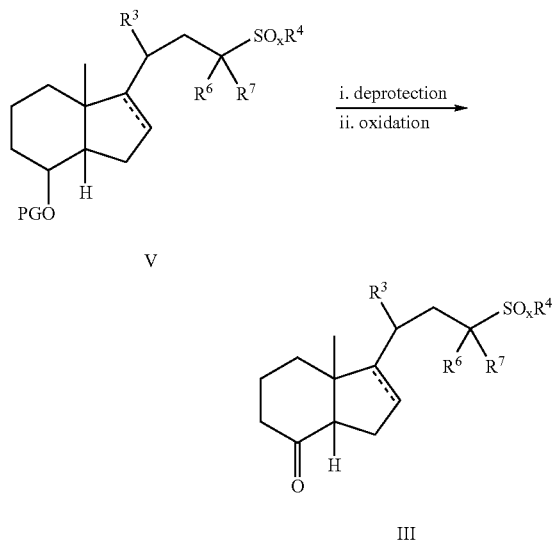

Suitably protected oxysulfones V, wherein $R^3$, $R^4$, $R^5$, $R^6$, x and ----- are as defined in Formula I and PG is a suitable protecting group, are first deprotected and then oxidized to provide ketones III, wherein $R^3$, $R^4$, $R^5$, $R^6$, x and ----- are as defined in Formula I. For example, when PG is trialkyl silyl, such as triethyl silyl, deprotection may be affected by reacting compounds of Formula V with tetrabutylammonium fluoride (TBAF) in an inert solvent, such as THF, and in an inert atmosphere, suitably at about room temperature. Oxidation of the resulting alcohol may be performed, for example, using pyridinium dichromate (PDC), tetrapropylammonium perruthenate (TPAP)/morpholine N-oxide (NMO), or any other suitable oxidizing agent, in an inert solvent such as methylene chloride, under standard conditions.

Compounds of Formula V, wherein $R^3$, $R^4$, $R^6$, $R^7$, x and ----- are as defined in Formula I and PG is a suitable protecting group, may be obtained, for example, as shown in Scheme 3:

Scheme 3

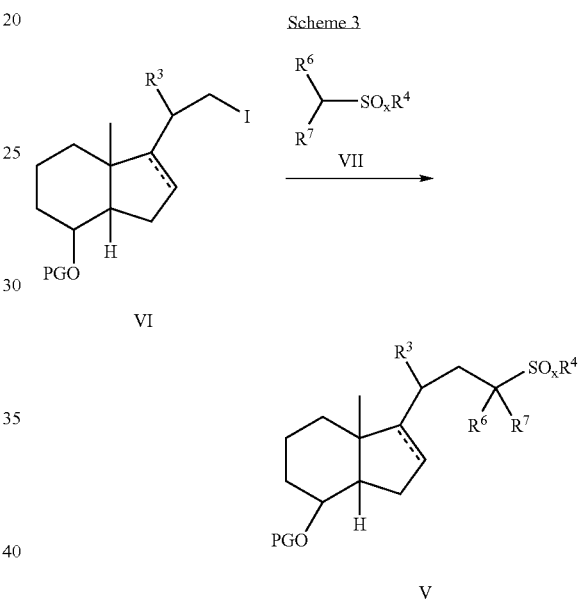

Compounds of Formula VI, wherein $R^3$ and ----- are as defined in Formula I and PG is a suitable protecting group, may be reacted with the anion of compounds of Formula VII, wherein $R^4$, R , $R^7$, x and ----- are as defined in Formula I, under anhydrous conditions at temperatures in the range of about –60° C. to about –90° C., suitably at about –78° C. The anions of compounds of Formula VII may be prepared by treating compounds of Formula VII with a strong base, for example an alkyl lithium such as n-butyl lithium, under inert conditions and, in the presence of hexamethyl phosphoramide (HMPA), for example, or $N,N,N^1,N^1$-tetramethylethylenediamine (TMEDA).

Compounds of Formula VII, wherein $R^4$, $R^6$ and $R^7$ are as defined in Formula I and x is 1 or 2, are either commercially available or may be prepared, for example, by the oxidation of the corresponding compounds of Formula VII, wherein $R^4$, $R^6$ and $R^7$ are as defined in Formula I and x is 0, as shown in Scheme 4. Suitable oxidizing agents include Ozone®, m-chloroperbenzoic acid and $RuCl_3H_2O$/periodic acid ($H_5IO_6$). The use of sterically hindered oxidizing reagents assists in the isolation of the sulfoxide (i.e. compounds of Formula VII, where x=1). An example of such an oxidizing reagent is camphorsulfonyl oxaziridine (available as pure enantiomers which can lead to the formation of enantiomerically enriched sulfoxides).

Scheme 4

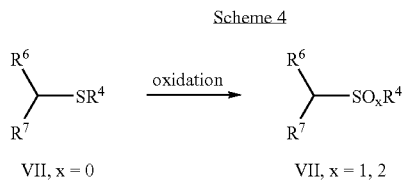

VII, x = 0   VII, x = 1, 2

Compounds of Formula VII, wherein $R^4$, $R^6$ and $R^7$ are as defined in Formula I and x is 0, are either commercially available or may be prepared, for example, as shown in Scheme 5. Therefore a reagent of Formula VIII, wherein $R^6$ and $R^7$ are as defined in Formula I and PG is a suitable leaving group, such as halogen, may be reacted with a compound of Formula IX, wherein $R^4$ is as defined in Formula I, in the presence of a base, for example sodium methoxide and an inert solvent, to provide compounds of Formula VII, wherein $R^4$, $R^6$ and $R^7$ are as defined in Formula I and x is 0.

Scheme 5

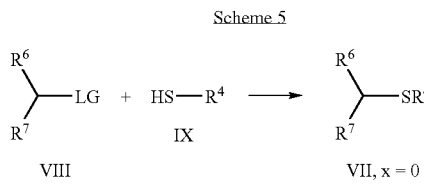

VIII   IX   VII, x = 0

An alternate route to the compounds of Formula V, wherein $R^3$, $R^4$, x and ----- are as defined in Formula I, $R^6$ and $R^7$ are H and PG is a suitable protecting group, is shown in Scheme 6. Accordingly, a compound of Formula X wherein $R^3$ and ----- are as defined in Formula I and PG is a suitable protecting group, may be reacted with a compound of Formula IX, wherein $R^4$ is as defined in Formula I, in the presence of a base such as 1,8-diazabicyclo[5.4.0]undec-7-ene (DBU), at elevated temperatures, such as about 110–150° C., suitably at about 130° C., in an inert, high-boiling solvent, such as benzene, to provide a compound of Formula V, wherein $R^3$, $R^4$, and ----- are as defined in Formula I, $R^6$ and $R^7$ are H, x is 0 and PG is a suitable protecting group. Oxidation of a compound of Formula V, wherein $R^3$, $R^4$, and ----- are as defined in Formula I, $R^6$ and $R^7$ are H, x is 0 and PG is a suitable protecting group, with suitable oxidizing agents, provides compounds of Formula V, wherein $R^3$, $R^4$, and ----- are as defined in Formula I, $R^6$ and $R^7$ are H, x is 1 or 2 and PG is a suitable protecting group. Suitable oxidizing agents include, for example Ozone®, m-chloroperbenzoic acid and $RuCl_3,H_2O$/periodic acid ($H_5IO_6$). The use of sterically hindered oxidizing reagents assists in the isolation of the sulfoxide (i.e. compounds of Formula V, where x=1). An example of such an oxidizing reagent is camphorsulfonyl oxaziridine (available as pure enantiomers which can lead to the formation of enantiomerically enriched sulfoxides).

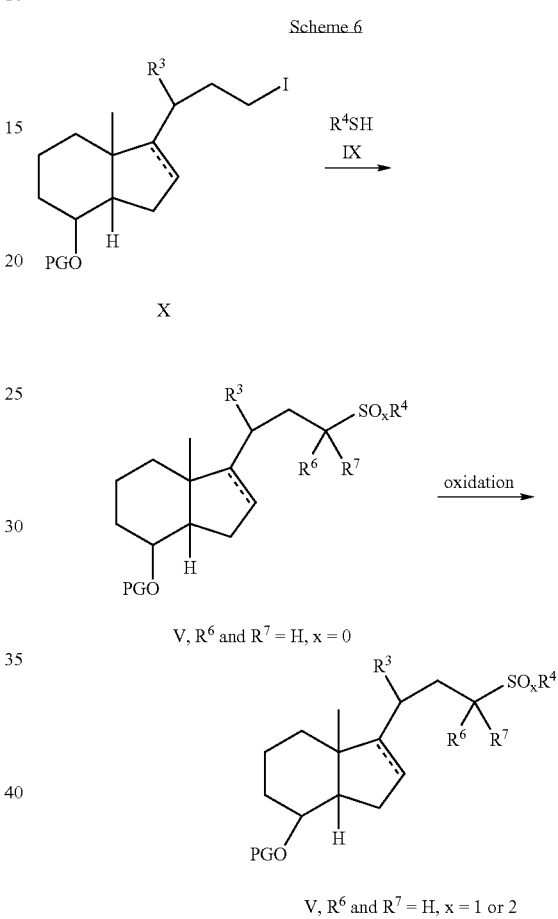

Scheme 6

Compounds of Formula V, wherein $R^3$, $R^4$ and ----- are as defined in Formula I, x is 1 or 2, $R^7$ and $R^8$ are both H and PG is a suitable protecting group, may alternatively be prepared from aldehyde XI as shown in Scheme 7. Therefore, a compound of Formula VII, wherein $R^4$ is as defined in Formula I, $R^6$ and $R^7$ are both H, and x is 1 or 2, is first treated with a strong base, such as an alkyl lithium, such as n-butyl lithium, under inert conditions and, in the presence of hexamethyl phosphoramide (HMPA), for example, or $N,N,N^1,N^1$-tetramethylethylenediamine (TMEDA), to generate the corresponding anion, which is then reacted with a compound of Formula XI, wherein $R^3$ and ----- are as defined in Formula I and PG is a suitable protecting group, under anhydrous conditions at temperatures in the range of about −60° C. to about −90° C., suitably at about −78° C. The resulting α,β-unsaturated sulfone may then be hydrogenated, for example, in the presence of $H_2$ over palladium on carbon, to provide compounds of Formula V, wherein $R^3$, $R^4$ and ----- are as defined in Formula I, x is 1 or 2, $R^7$ and $R^8$ are both H and PG is a suitable protecting group.

Scheme 7

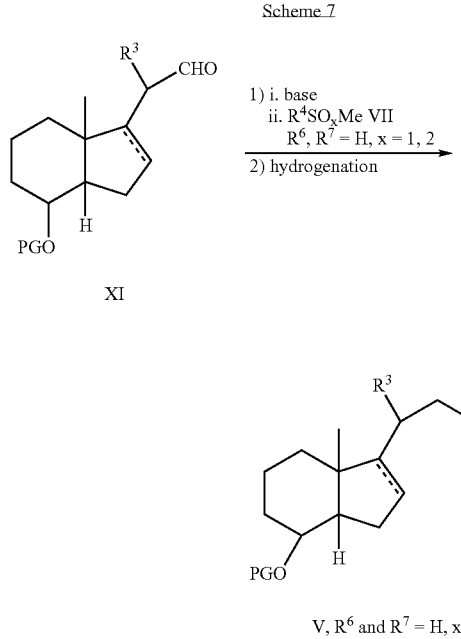

Aldehydes of Formula XI, wherein $R^3$ and ----- are as defined in Formula I and PG is a suitable protecting group may be prepared using standard chemistries, for example as shown in Scheme 8. The alcohol groups of compounds of Formula XII, wherein $R^3$ and ----- are as defined in Formula I, may be selectively protected to form compounds of Formula XIII, wherein PG and PG are the protecting groups for the primary and secondary alcohol groups respectively, using standard chemistries (see "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.). The primary protected alcohol tosylate of compounds of Formula XII may then be selectively oxidized directly to the corresponding aldehyde XI, for example, in the presence of sodium hydrogen carbonate in a polar aprotic solvent such as dimethylsulfoxide (DMSO) at an elevated temperature, for example 150° C., using a procedure described in Kornblum, et al. *J. Am. Chem. Soc.* 1959, 81:4113–4116.

Scheme 8

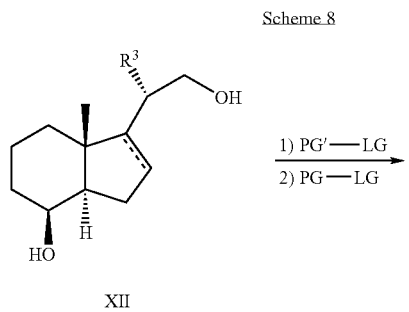

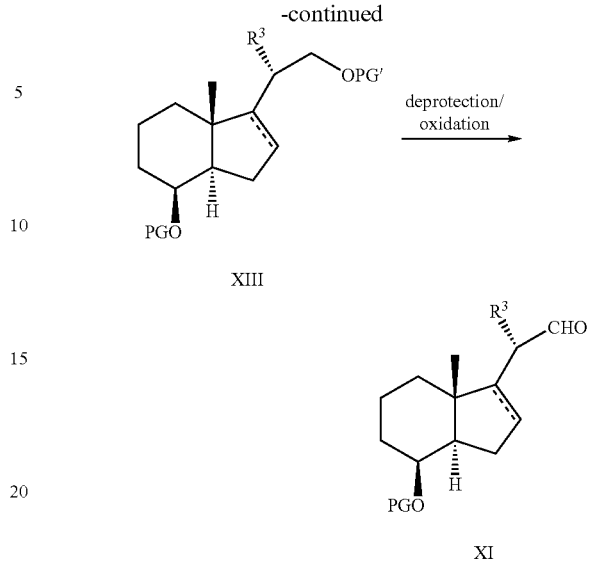

The preparation of compounds of Formula VI, wherein $R^3$ and ----- are as defined in Formula I, and PG is a suitable protecting group, is known in the art. Therefore compounds of Formula VI may be prepared as described in Posner, G. H. et al. *J. Med. Chem* .1992, 42, 3425–3435, the contents of which are incorporated herein by reference.

The preparation of compounds of Formula X, wherein $R^3$ and ----- are as defined in Formula I, and PG is a suitable protecting group, is known in the art. Therefore compounds of Formula X may be prepared as described in Posner, G. H. et al. *J. Med. Chem.* 1992, 42, 3425–3435; in Jaekyoo Lee, Ph.D. Thesis, 1997, Johns Hopkins University; or in Posner G. H. et al. U.S. Pat. No. 6,380,408, the contents of which are incorporated herein by reference.

The preparation of compounds of Formula IV, wherein $R^1$, $R^2$ and $R^5$ are as defined in Formula I is known in the art. Therefore compounds of Formula IV, wherein $R^1$ and $R^2$ are as define in Formula I and both $R^5$'s together form $=CH_2$, may be prepared as described in Posner, G. H. et al. *J. Med. Chem.* 1992, 35, 3280–3287, the contents of which are incorporated herein by reference. Compounds of Formula IV, wherein $R^1$ and $R^2$ are as define in Formula I and both $R^5$'s are is H, may be prepared as described in Hilpert, H. and Wirz, B. *Tetrahedron* 2001, 57, 681–694, the contents of which are incorporated herein by reference.

The preparation of compounds of Formula XII, where $R^3$ and ----- are as defined in Formula I is known. Therefore compounds of Formula XII, where R and ----- are as defined in Formula I, may be prepared as described in Posner, G. H. et al. *J. Org. Chem.* 1997, 62, 3299–3314, the contents of which are incorporated herein by reference.

The preparation of enantiomerically pure compounds of Formula I, may be accomplished by using enantiomerically pure compounds of Formula III and IV in the reaction shown in Scheme I. In this reaction, a mixture of the 1α,3β and 1β,3α diastereomers is typically obtained, with the 1α,3β diastereomer as the major product. These diastereomers may be separated using chromatography, for example using high performance liquid chromatography (HPLC).

In some cases the chemistries outlined above may have to be modified, for instance by use of protective groups, to prevent side reactions due to reactive groups, such as reactive groups attached as substituents. This may be achieved by means of conventional protecting groups, for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 1991.

Further, the chemistries above may be modified by changing the order of the reaction sequences. For example, compounds of Formula VI or compounds of Formula X, or compounds that may be converted to a compound of Formula VI or a compound of Formula X, may first be coupled with compounds of Formula IV, using standard HWE coupling conditions, and these coupled products, after conversion to the corresponding iodide (for example) if necessary, may be reacted with compounds of Formula VII or compounds of Formula IX, respectfully, as described above, to provide (after deprotection, if necessary) compounds of Formula I. An example of such a reaction sequence is shown below in Scheme 9:

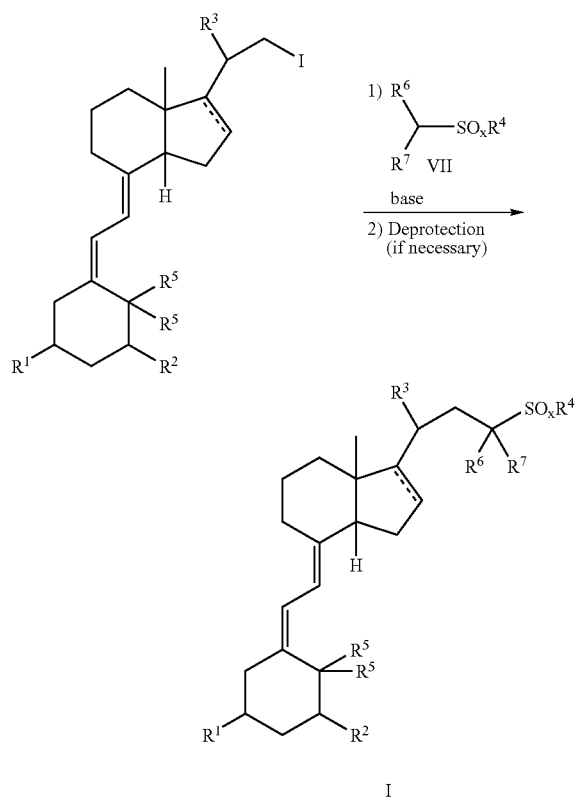

The iodide reactant shown in Scheme 9, may be prepared from the corresponding alcohol as reported by Manchand, S. M. et al. *J. Org. Chem.* 1995, 60. 6574–6581).

The formation of a desired compound salt is achieved using standard techniques. For example, the neutral compound is treated with an acid or base in a suitable solvent and the formed salt is isolated by filtration, extraction or any other suitable method.

The formation of solvates of the compounds of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Prodrugs of the compounds of the invention may be conventional esters formed with available hydroxy, thiol, amino or carboxyl group. For example, when $R^1$ and/or $R^2$ is OH and/or $R^4$ is substituted with one or more OH or $NH_2$ in a compound of the invention, it may be acylated using an activated acid in the presence of a base, and optionally, in inert solvent (e.g. an acid chloride in pyridine). Also, when $R^4$ is substituted with one or more C(O)OH in a compound of the invention, an ester may be formed by activation of the hydroxyl group of the acid and treatment with the appropriate alcohol in the presence of a base in an inert solvent. Some common esters which have been utilized as prodrugs are phenyl esters, aliphatic ($C_8$–$C_{24}$) esters, acyloxymethyl esters, carbamates and amino acid esters.

A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50–100 C.

IV. Uses

As hereinbefore mentioned, novel compounds of the Formula I have been prepared. Accordingly, the present invention includes all uses of the compounds of the invention including their use in therapeutic methods and compositions for modulating CYP24 activity, their use in diagnostic assays and their use as research tools.

Selectively inhibiting the cytochrome P450 enzymatic pathway, through which 1α,25-dihydroxy vitamin $D_3$ is catabolized (mainly via C-24 hydroxylation), is one important way to prolong the lifetime of this hormone, or analogs thereof. Therefore, the compounds of Formula I were tested in vitro, using a standard protocol, for their ability to inhibit specifically CYP24, an enzyme responsible for 24-hydroxylation of 1α,25-dihydroxy vitamin $D_3$. Antimycotic ketoconazole, a drug used clinically for chemotherapy of human prostate cancer (Trachtenberg, J. et al. J. Urol. 1984, J32, 61–63), was used as a control standard for inhibition of CYP24. Compounds I(a), I(e), I(g), I(i), I(v), I(w), I(y) and I(gg) have been shown to selectively inhibit the CYP24.

By selectively modulating CYP24, the enzyme that metabolizes 1α,25-dihydroxy vitamin $D_3$, the levels of 1α,25-dihydroxy vitamin $D_3$ (either endogenous or administered as part of a chemotherapeutic regimen), or analogs thereof, may also be modulated. Diseases that benefit from a modulation, in particular an increase, of the levels of 1α,25-dihydroxy vitamin $D_3$ can therefore be treated using a modulator of CYP24. By acting preferentially on CYP24, side effects caused by interaction with other enzymes and receptors may be reduced. Accordingly, the present invention provides a method for treating diseases which benefit from a modulation, preferably an increase, of the levels of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from a modulation, preferably an increase, of the levels of 1α,25-dihydroxy vitamin $D_3$, or an analog of 1α,25-dihydroxy vitamin $D_3$. Further, the invention includes a use of a compound of the invention to prepare a medicament to treat diseases which benefit from a modulation, preferably an increase, of the levels of 1α,25-dihydroxy vitamin $D_3$, or an analog of 1α, 25-dihydroxy vitamin $D_3$.

Inhibition of CYP24 will inhibit the catabolism of 1α,25-dihydroxy vitamin $D_3$, or its analogs, which is expected to lengthen the biological lifetime of these compounds and thus allow smaller amounts of them to be used for effective disease treatment. Such smaller dosing is expected to avoid, or at least minimize, the hypercalcemic toxicity associated with medicinal use of 1α,25-dihydroxy vitamin $D_3$ and its analogs. Further, by inhibiting the catabolism of 1α,25-dihydroxy vitamin $D_3$, the compounds of the invention will increase the endogenous levels of this hormone, which will have similar beneficial therapeutic effects. Therefore, in an embodiment, the present invention provides a method for treating diseases which benefit from inhibiting the catabolism of 1α,25-dihydroxy vitamin $D_3$, or an analog of 1α,25-dihydroxy vitamin $D_3$, comprising administering an effective amount of a compound of the invention to a cell or animal in need thereof. The invention also includes the use of a compound of the invention to treat diseases which benefit from inhibiting the catabolism of 1α,25-dihydroxy vitamin $D_3$, or an analog of 1α,25-dihydroxy vitamin $D_3$. Further, the invention includes a use of a compound of the invention to prepare a medicament to treat diseases which benefit from inhibiting the catabolism of 1α,25-dihydroxy vitamin $D_3$, or an analog of 1α,25-dihydroxy vitamin $D_3$.

Diseases which will benefit for a modulation in the levels of 1α,25-dihydroxy vitamin $D_3$ include, but are not limited to:
  i. in the parathyroid—hyper- and hypo-parathyroidism, Osudohypo-parathyroidism, Secondary hyperparathyroidism;
  ii. in the pancreas—diabetes;
  iii. in the thyroid—medullary carcinoma;
  iv. in the skin psoriasis, wound healing;
  v. in the lung—sarcoidosis and tuberculosis;
  vi. in the kidney—chronic renal disease, hypophosphtatemic VDRR, vitamin D dependent rickets;
  vii. in the bone—anticonvulsant treatment, fibrogenisis imperfecta ossium, osteitits fibrosa cystica, osteomalacia, osteoporosis, osteopenia, osteosclerosis, renal osteodytrophy, rickets;
  viii. in the intestine—glucocorticoid antagonism, idopathic hypercalcemia, malabsorption syndrome, steatorrhea, tropical sprue; and
  ix. autoimmune disorders.

In embodiments of the invention, the disease that benefits from a modulation in the levels of 1α,25-dihydroxy vitamin $D_3$, or an analog of 1α,25-dihydroxy vitamin $D_3$, are selected from cancer, dermatological disorders (for example psoriasis), parathyroid disorders (for example hyperparathyroidism and secondary hyperparathyroidism), bone disorders (for example osteoporosis) and autoimmune disorders.

In accordance with a further aspect of the present invention, the disease that benefits from a modulation, in particular an increase, in the levels of 1α,25-dihydroxy vitamin $D_3$, or an analog of 1α,25-dihydroxy vitamin $D_3$, is a cell proliferative disorder. Accordingly, there is provided a method for modulating cell proliferation (preferably inhibiting cell proliferation) and/or promoting cell differentiation, comprising administering an effective amount of a compound of the invention to a cell or animal in need thereof. The invention also includes a use of a compound of the invention to modulate cell proliferation (preferably to inhibit cell proliferation) and/or to promote cell differentiation. The invention further includes a use of a compound of the invention to prepare a medicament to modulate cell proliferation (preferably to inhibit cell proliferation) and/or to promote cell differentiation.

In particular, the method of the invention is useful in inhibiting the proliferation of abnormal but not normal cells. Abnormal cells include any type of cell that is causative of or involved in a disease or condition and wherein it is desirable to modulate or to inhibit the proliferation of the abnormal cell, or to promote its differentiation, in order to treat the disease or condition. Examples of abnormal cells include malignant or cancerous cells as well as cells that over-proliferate in inflammatory conditions such as psoriasis.

In another embodiment of the present invention, the disease that benefits from a modulation, in particular an increase, in the levels of 1α,25-dihydroxy vitamin $D_3$, or an analog of 1α,25-dihydroxy vitamin $D_3$, is cancer. Accordingly, the present invention provides a method of treating cancer comprising administering an effective amount of a compound of the invention to a cell or animal in need thereof. The invention also includes a use of a compound of the invention to treat cancer. The invention further includes a use of a compound of the invention to prepare a medicament to treat cancer. In embodiments of the invention, the cancer is selected from the group consisting of breast cancer, lung cancer, prostate cancer, colon and colorectal cancer, kidney cancer, head and neck cancer, pancreatic cancer, skin cancer, Kaposi's sarcoma and leukemia.

In another aspect, the invention provides a method of modulating CYP24 activity in a cell by administering an effective amount of a compound of the invention. In a further aspect, the invention provides a method of inhibiting CYP24 activity in a cell by administering an effective amount of a compound of the invention. The present invention also provides a use of a compound of the invention to modulate, preferably to inhibit, CYP24 activity. The present invention further provides a use of a compound of the invention to prepare a medicament to modulate CYP24 activity, preferably to inhibit, CYP24 activity.

The compounds of the invention can be used alone or in combination with other agents that modulate CYP24 activity, or in combination with other types of treatment (which may or may not modulate CYP24) for diseases that benefit from a modulation, preferably an increase, in the levels of 1α,25-dihydroxy vitamin $D_3$, or analogs thereof, and/or an inhibition of the catabolism of 1α,25-dihydroxy vitamin $D_3$, or an analog thereof. Preferably the compounds of the invention are administered in combination with 1α,25-dihydroxy vitamin $D_3$ (calcitriol), an analog of 1α,25-dihydroxy vitamin $D_3$ or other vitamin D receptor agonists. Inhibiting catabolism of vitamin D receptor agonists such as 1α,25-dihydroxy vitamin $D_3$, or analogs thereof, will lengthen the biological lifetime or efficacy of these therapies and thus allow smaller amounts of the drug to be used for effective human chemotherapy; such smaller dosing will avoid, or at least minimize, the side effects, for example the hypercalcemic toxicity, associated with medicinal use of these compounds. The present invention therefore provides a method of increasing the efficacy of a vitamin D receptor agonist comprising co-administering an effective amount of a compound of the invention and an effective amount of the vitamin D receptor agonist. Further the invention includes the use of a compound of the invention to increase the efficacy of a vitamin D receptor agonist and a use of a compound of the invention to prepare a medicament to increase the efficacy of a vitamin D receptor agonist. In embodiments of the invention, the vitamin D receptor agonist is 1α,25-dihydroxy vitamin $D_3$, or an analog thereof. By analog of 1α,25-dihydroxy vitamin $D_3$, it is meant a chemically modified analog of 1α,25-dihydroxy vitamin $D_3$ which is a vitamin D receptor agonist and therefore exhibits a therapeutic profile similar to 1α,25-dihydroxy vitamin $D_3$. Examples of such compounds can be found in the following review articles, the contents of which are incorporated herein by reference: Pinette, K. V et al. "Vitamin D Receptor as a Drug Discovery Target", Mini Reviews in Med. Chem. 2003, 3:193–204; Mathieu, C. and Adorini, L. "The Coming of Age of 1,25-Dihydroxy Vitamin $D_3$ Analogs as Immunomodulatory Agents", Trends in Mol. Med. 2002, 8:174–179; Carlberg, C. "Molecular Basis of the Selective Activity of Vitamin D Analogues", J. Cell. Bio. 2003, 88:274–281; Stein, M. S. and Wark, J. D. "An update on the therapeutic potential of vitamin D analogues", Expert Opin. Invest. Drugs 2003, 12:825–840; Bouillon, R. et al. "Structure-Function Relationships in the Vitamin D Endocrine System" Endocr. Rev. 1995, 16:200–257; and Nagpal, S. et al. "Vitamin D Analogs: Mechanism of Action and Therapeutic Applications", Current Med. Chem. 2001, 8:1661–1679.

Treatments used in combination with the compounds of the present invention may be based on the disease type and do not have to specifically target CYP24, activity or the VDR. In a particular aspect of the present invention, the compounds of the invention are used in combination with other therapies and therapeutics to treat dermatological disorders, bone disorders, cancer and autoimmune disorders. Such therapies include, but are not limited to the following: for cancer: surgery, radiation, chemotherapies and biotherapies; for psoriasis: ultraviolet B radiation, chemotherapy and biotherapies.

One skilled in the art can determine which compounds of the invention would have therapeutic utility, for example, in inhibiting cell proliferation in any type of cancer or cell proliferative disorder. Compounds may be examined for their potency in inhibiting cell growth in cell proliferation assays such as inhibition of growth of murine keratinocyte cells (cell line PE) and for the inhibition of TPA-induced ornithine decarboxylase (ODC) activity as described in U.S. Pat. No. 5,830,885, the contents of which are incorporated herein by reference.

In addition to cancer, the compounds of the invention are useful in treating other conditions involving aberrant or abnormal cell proliferation. Other cell proliferative disorders that may be treated by the present invention include inflammatory diseases, allergies, autoimmune disease, graft rejection, psoriasis, restenosis, artherosclerosis, and any other disorder wherein it is desirable to inhibit, prevent or suppress cell growth. Compounds of the invention may be tested for their potency in a particular cell proliferation disorder using assays and techniques known to those of skill in the art. For example, the following references provide assays for various conditions: Rheumatoid Arthritis: "Regulation of IL-15—Simulated TNF-alpha Production by Rolipram", Journal of Immunology (1999) volume 163 page 8236 by C. S. Kasyapa et al.; Allergy: "A novel Lyn-Binding Peptide Inhibitor Blocks Eosinophil Differentiation, Survival, and Airway eosinophilic inflammation". Journal of Immunology (1999) volume 163 page 939 by T. Adachi et al.; Psoriasis: Journal of Immunology (2000) volume 165 page 224 "Inhibition of Keratinocyte apoptosis by IL-15: a new parameter in the pathegenosis of psoriasis" by R. Üchert; and Psoriasis: International Archives of allergy and Immunology (2000) Volume 123 page 275. "T-cell receptor mimic peptides and their potential application in T-cell mediated disease" by A. H. Enk.

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier. The present invention further comprises a pharmaceutical composition comprising a compound of the invention and a vitamin D receptor agonist in admixture with a suitable diluent or carrier. In embodiments of the invention, the vitamin D receptor agonist is 1α,25-dihydroxy vitamin $D_3$, or an analog thereof.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the invention may be used in the form of the free base, in the form of solvates and as hydrates. All forms are within the scope of the invention.

In accordance with the methods of the invention, the described compounds or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention thereof may be orally administered, for example, with an inert diluent or with an assimilable edible carder, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (1990—18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including anti-oxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The compounds of the invention may be administered to an animal alone or in combination with pharmaceutically acceptable carriers, as noted above, the proportion of which is determined by the solubility and chemical nature of the compound, chosen route of administration and standard pharmaceutical practice.

The dosage of the compounds and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. For example, in the topical treatment, ointments, creams, or lotions containing from 1–1000 µg/g of a compound of the invention may be administered. Oral preparations may be formulated, preferably as tablets, capsules, or drops, containing from 0.5–1000 µg of a compound of the invention, per dosage unit. The compounds of the invention may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

In addition to the above-mentioned therapeutic uses, the compounds of the invention are also useful in diagnostic assays, screening assays and as research tools.

In diagnostic assays the compounds of the invention may be useful in identifying or detecting a cell proliferative disorder. In such an embodiment, the compounds of the invention may be radiolabelled (as hereinbefore described) and contacted with a population of cells. The presence of the radiolabel on the cells may indicate a cell proliferative disorder.

In screening assays, the compounds of the invention may be used to identify other compounds that modulate cell proliferation or CYP24 activity. As research tools, the compounds of the invention may be used in receptor binding assays and assays to study the localization of CYP24. In such assays, the compounds may also be radiolabelled.

The following non-limiting examples are illustrative of the present invention:

EXAMPLES

Materials and Methods

Unless otherwise noted, all reactions were performed in oven-dried glassware stirred under an atmosphere of ultra-high-purity argon. THF was distilled from Na/benzophenone ketyl and $CH_2Cl_2$ distilled from $CaH_2$ immediately prior to use. Organolithiums were titrated prior to use following known methods (Suffert, J. *J. Org. Chem.* 1989, 54, 509–510). All other reagents were used as received from commercial suppliers. Analytical TLC analysis was conducted on precoated glass-backed silica gel plates (Merck Kieselgel 60 $F_{254}$, 250 mm thickness) and visualized with p-anisaldehyde or $KMnO_4$ stains. Column chromatography was performed using short path silica gel (particle size <230 mesh) or flash silica gel (particle size 230–400 mesh). Preparative-plate chromatography was performed using silica-gel-coated glass preparative plates (500–1000 µm) from Analtech and analyzed by UV. HPLC was carried out using a Rainin HPLX™ system equipped with two 25-mL/min preparative pump heads using (1) a Chiral Technologies CHIRALCEL® OJ 10-mm×250-mm (semipreparative) column packed with cellulose tris(4-methylbenzoate) on a 10 µm silica-gel substrate or (2) a Phenomenex LUNA™ 10-mm×250-mm (semipreparative) column packed with 110 Å silica gel (5 µm pore size) as C-18-bonded silica and a Rainin Dynamax™ UV-C dual-beam variable-wavelength detector set at 254 nm. Yields are reported for pure products (>95% based on their chromatographic and spectroscopic homogeneity) and are unoptimized. Melting points were determined in open capillaries using a Mel-Temp metal-block apparatus and are uncorrected. Optical rotations were measured at the Na line using a Perkin-Elmer 141 Polarimeter. NMR spectra were obtained on a Varian XL-400 spectrometer operating at 400 MHz for $^1$H, 376 MHz for $^{19}$F, and 100 MHz for $^{13}$C and a Bruker 300 AMX spectrometer operating at 300 MHz for $^1$H. Chemical shifts are reported in ppm (δ) and are referenced to CDCl$_3$ (7.26 ppm for $^1$H and 77.0 ppm for $^{13}$C), tetramethylsilane (TMS, 0.00 ppm for $^1$H), and CFCl$_3$ (0.00 ppm for $^{19}$F). IR spectra were obtained using a Perkin Elmer 1600 Series FT-IR instrument. HRMS were obtained at the mass spectrometry facility at the Ohio State University on a Micromass QTOF Electrospray mass spectrometer. Elemental analyses were performed by Atlantic Microlab Inc., Norcross, Ga.

Example 1

General Procedure for the Preparation of Aryl Methyl Sulfones VII

To an ice-cold solution containing the appropriate aryl methyl sulfide (6.00 mmol) in MeOH (24.0 mL) was added oxone® (9.00 mmol) as a solution in H$_2$O (20.0 mL) dropwise via addition funnel. The resulting cloudy slurry was stirred at room temperature overnight, diluted with water, and extracted with CHCl$_3$ (3×). The combined organics were washed with water and brine, dried over Na$_2$SO$_4$, and concentrated under reduced pressure to give essentially quantitative recovery of the aryl methyl sulfones VII (a–c) as crystalline solids.

a) Methyl-(4-methoxyphenyl) sulfone. According to the general procedure for the preparation of aryl methyl sulfones described above, 1-methanesulfanyl-4-methoxy-benzene (1.00 g, 6.48 mmol) gave 1.20 g (99%) of the title compound as a white solid: mp 114–115° C. (lit. mp 115° C., Helv. Chim. Acta. 1999, 82, 372–388); $^1$H NMR (400 MHz, CDCl$_3$) δ 7.89–7.83 (dt, J=9.5, 2.8, 2.2 Hz, 2H), 7.04–6.99 (dt, J=9.5, 2.8, 2.2 Hz, 2H), 3.88 (s, 3H), 3.02 (s, 3H); $^{13}$C NMR (100 MHz, CDCl$_3$) δ 163.6, 132.3, 129.5, 114.5, 55.7, 44.8; IR (neat) 3020, 3010, 2982, 1575, 1412, 1323, 1293, 1142, 1092, 1023, 835, 766, 544, 528 cm$^{-1}$; Anal. Calcd for C$_8$H$_{10}$O$_3$S: C, 51.60; H, 5.41. Found: C, 51.64; H, 5.43.

b) Methyl-(4-nitrophenyl) sulfone. According to the general procedure for the preparation of aryl methyl sulfones described above, 1-methanesulfanyl-4-nitrobenzene (1.00 g, 5.41 mmol) gave 1.19 g (100%) of the title compound as a yellow solid: mp 137–139° C.; $^1$H NMR (400 MHz, CDCl$_3$) δ 8.45–8.40 (dt, J=9.0, 2.5 Hz, 2H), 8.19–8.14 (dt, J=9.0, 2.5Hz, 2H), 3.12 (s, 3H).

c) Methyl-(4-trifluoromethylphenyl) sulfone. According to the general procedure for the preparation of aryl methyl sulfones described above, 1-methanesulfanyl-4-trifluoromethylbenzene, synthesized from 4-chloro-1-trifluoromethyl benzene and sodium methanethiolate as described in Cabiddu, M. G. et al., J. Organometallic Chem. 1997, 531, 125–140. (1.07 g, 5.57 mmol) gave 1.21 g (97%) of the title compound as a white solid: mp 100–101° C.; $^1$H NMR (300 MHz, CDCl$_3$) δ 8.13–8.07 (d, J=11.1 Hz, 2H), 7.89–7.83 (d, J=11.1 Hz, 2H), 3.09 (s, 3H); $^{13}$C NMR (100 MHz, CDCl$_3$) δ 143.9, 135.4 (d, J=32.6 Hz), 128.1, 126.5 (d, J=0.8 Hz), 123.0 (d, J=123.0 Hz), 44.3; $^{19}$F NMR (375 MHz, CDCl$_3$, CFCl$_3$) δ –69.4 (m).

Example 2

Preparation of Methyl (p-acetalphenyl) Sulfone

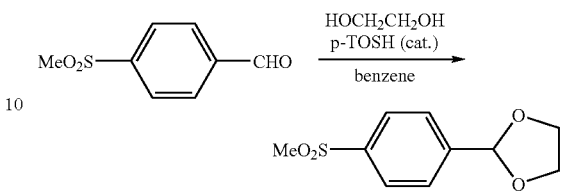

A mixture of 4-methylsulphonyl benzaldehyde (750 mg, 3.87 mmol, 95% purity) and ethylene glycol (0.9 mL, 16.0 mmol) in benzene (10 mL) in the presence of catalytic amount of p-TsOH was refluxed for 6.5 h. After benzene was distilled off, the residue was dissolved into EtOAc. The organic layer was washed with brine, saturated aq. NaHCO$_3$, and brine again, dried over MgSO$_4$, filtered, concentrated to afford 781.9 mg (88%) of a crude product which was directly used for the next reaction without further purification. R$_f$ 0.37 (1:1-EtOAc:Hex); $^1$H NMR (400 MHz, CDCl$_3$) δ 7.95–7.98 (m, 2H), 7.68–7.71 (m, 2H), 5.89 (s, 1H), 4.05–4.15 (m, 4H), 3.05 (s, 3H).

Example 3

(Triethylsilyl)-oxy-aryl Sulfones V (a) (Triethylsilyl)-oxy-phenyl Sulfone

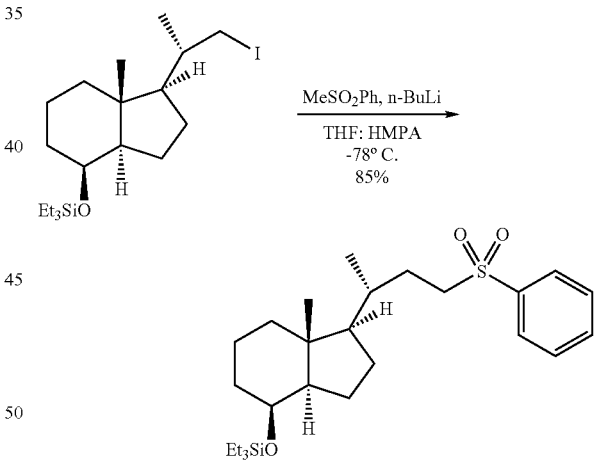

To a cold (–78° C.) solution of methyl phenyl sulfone (125 mg, 0.802 mmol) in THF (2.25 mL) was added a solution of n-BuLi (556 μL, 0.802 mmol, 1.44 M in hexanes) dropwise via syringe. After 15 min, HMPA (0.1–0.2 mL) was added and the solution was stirred for an additional 15 min at –78° C. A precooled (–78° C.) solution of the (+)-triethylsilyl iodide (Posner, G. H.; Crawford, K. R. unpublished results, 100 mg, 0.229 mmol) in THF (0.75 mL) was added slowly via cannula. The reaction mixture was then warmed to room temperature. The reaction was quenched with H$_2$O, extracted with Et$_2$O (3×), washed with brine, dried over MgSO$_4$, and concentrated to a crude solid that was purified by chromatography (5→20% EtOAc/hexanes) to give 91 mg (85%) of the title compound as a colorless oil: $[\alpha]_D^{25}$+36.7 (c 4.3, CHCl$_3$); $^1$H NMR (400 MHz, CDCl$_3$) δ 7.92–7.85 (m, 2H), 7.67–7.59 (tt, J=7.4, 1.5 Hz, 1H), 7.59–7.50 (m, 2H), 4.04–3.96 (m, 1H), 3.16–3.04 (m, 1H), 3.02–2.91 (m, 1H), 0.92 (t, J=8.0 Hz, 9H), 0.84 (s, 3H), 0.83 (d, J=6.8 Hz,3H), 0.52 (q, J=8.0 Hz, 6H); $^{13}$C NMR (100 MHz, CDCl$_3$) δ 139.2, 133.5, 129.1, 128.0, 69.2, 55.9, 53.6, 52.9, 42.1, 40.6, 34.4, 34.2, 28.2, 26.9, 22.8, 18.2, 17.5, 13.4, 6.9, 4.9; IR (neat) 2949, 2912, 2873, 1446, 1317, 1306, 1234, 1148, 1087, 1021, 803, 740, 724, 689 cm$^{-1}$; HRMS: calcd for C$_{26}$H$_{44}$O$_5$SSi+Na, 487.2678, found 487.2672.

In a like manner, the following additional compounds were prepared:

(b) (+)-(Triethylsilyl)-oxy-(4-fluorophenyl) Sulfone: By replacing methyl phenyl sulfone with methyl (4-fluorophenyl) sulfone. The crude mixture was purified by flash chromatography (EtOAc:Hex=1:15 to 1:13) to afford 78 mg (85%) of C24-p-fluorophenyl sulfone. R$_f$ 0.37 (1:9-EtOAc:Hex); $[\alpha]D^{26}$+36.0 (c 1.11, CHCl$_3$); $^1$H NMR (400 MHz, CDCl$_3$) δ 7.90–7.94 (m, 2H), 7.23–7.27 (m, 2H), 4.01 (d, J=2.4 Hz, 1H), 3.12 (ddd, J=4.0, 12.0, 13.6 Hz, 1H), 2.98 (ddd, J=4.8, 11.6, 14.0 Hz, 1H), 1.70–1.88 (m, 2H), 1.61–1.68 (m, 2H), 1.40–1.57 (m, 3H), 1.02–1.38 (m, 8H), 0.93 (t, J=7.6 Hz, 9H), 0.86 (s, 3H), 0.85 (d, J=7.2 Hz, 3H), 0.54 (q, J=8.0 Hz, 6H); $^{13}$C NMR (100 MHz, CDCl$_3$) δ 165.7 (d, J=255.1), 135.2 (d, J=3.2), 130.9 (d, J=9.6), 116.5 (d, J=22.3), 69.2, 55.9, 53.8, 52.9, 42.1, 40.6, 34.5, 34.2, 28.3, 27.0, 22.8, 18.3, 17.6, 13.5, 6.9, 4.9; IR (thin film) 2950, 2876, 1592, 1494, 1321, 1289, 1236, 1148, 1087 cm$^{-1}$; HRMS calc'd for [M+Na]: 505.2578 for C$_{26}$H$_{43}$FO$_3$SSiNa. found: 505.2561.

(c) (+)-Triethylsilyl)-oxy-(4-chlorophenyl) Sulfone: By replacing methyl phenyl sulfone with methyl (4-chlorophenyl) sulfone. The crude mixture was purified by flash chromatography (EtOAc:Hex=1:12 to 1:7) to afford 87.5 mg (96%) of C24-p-chlorophenyl sulfone. R$_f$ 0.35 (1:9-EtOAc:Hex); $[\alpha]D^{26}$+37.8 (c 0.91, CHCl$_3$); $^1$H NMR (400 MHz, CDCl$_3$) δ 7.82–7.86 (m, 2H), 7.53–7.56 (m, 2H), 4.01 (m, 1H), 3.11 (ddd, J=4.8, 12.0, 13.6 Hz, 1H), 2.97 (ddd, J=4.8, 11.6, 14.0 Hz, 1H), 1.76–1.90 (m, 2H), 1.60–1.69 (m, 2H), 1.40–1.58 (m, 3H), 1.02–1.36 (m, 8H), 0.93 (t, J=8.0 Hz, 9H), 0.86 (s, 3H), 0.85 (d, J=6.4 Hz, 3H), 0.54 (q, J=8.0 Hz, 6H); $^{13}$C NMR (100 MHz, CDCl$_3$) δ 140.3, 137.6, 129.5, 69.1, 55.9, 53.7, 52.9, 42.1, 40.6, 34.4, 34.2, 28.2, 27.0, 22.8, 18.2, 17.6, 13.4, 6.9, 4.9; IR (thin film) 2950, 2875, 1312, 1150, 1088 cm$^{-1}$; HRMS calc'd for [M+Na]: 521.2288 for C$_{26}$H$_{43}$ClO$_3$SSiNa. found: 521.2275.

(d) (+)-(Triethylsilyl)-oxy-(4-methylphenyl) Sulfone: By replacing methyl phenyl sulfone with methyl (4-methylphenyl) sulfone. The crude mixture was purified by flash chromatography (EtOAc:Hex=1:12 to 1:10) to afford 84.6 mg (93%) of C24-p-tolyl sulfone. R$_f$ 0.23 (1:9-EtOAc:Hex); $[\alpha]D^{26}$+36.9 (c 0.96, CHCl$_3$); $^1$H NMR (400 MHz, CDCl$_3$) δ 7.76–7.78 (m, 2H), 7.33–7.36 (m, 2H), 3.99 (d, J=2.4 Hz, 1H), 3.09 (ddd, J=4.0, 12.0, 13.6 Hz, 1H), 2.95 (ddd, J=4.8, 11.6, 14.0 Hz, 1H), 2.44 (s, 3H), 1.72–1.87 (m, 3H), 1.62–1.68 (m, 2H), 1.38–1.60 (m, 3H), 1.00–1.35 (m, 7H), 0.92 (t, J=7.6 Hz, 9H), 0.84 (s, 3H), 0.82 (d, J=6.4 Hz, 3H), 0.52 (q, J=7.6 Hz, 6H); $^{13}$C NMR (100 MHz, CDCl$_3$) δ 144.4, 136.2, 129.8, 128.0, 69.2, 55.9, 53.7, 52.9, 42.1, 40.6, 34.5, 34.2, 28.3, 27.0, 22.8, 21.6, 18.2, 17.6, 13.4, 6.9, 4.9; IR (thin film) 2950, 2875, 1598, 1456, 1316, 1148, 1088 cm$^{-1}$; HRMS [M+Na] calc'd 501.2829 for C$_{27}$H$_{46}$O$_3$SSiNa. found: 501.2810.

(e) (+)-(Triethylsilyl)-oxy-(3,4-dichlorophenyl) Sulfone: By replacing methyl phenyl sulfone with methyl (3,4-dichlorophenyl) sulfone. The crude mixture was purified by flash chromatography (EtOAc:Hex=1:12) to afford 65.6 mg (66%) of C24-3,4-dichlorophenyl sulfone. R$_f$ 0.38 (1:9-EtOAc:Hex); $[\alpha]D^{26}$+32.2 (c 1.03, CHCl$_3$); $^1$H NMR (400 MHz, CDCl$_3$) δ 8.00 (d, J=2.0 Hz, 1H), 7.73 (dd, J=2.0, 8.4 Hz, 1H), 7.66 (d, J=8.4 Hz, 1H), 4.02 (d, J=2.4 Hz, 1H), 3.13 (ddd, J=4.8, 12.0, 14.0 Hz, 1H), 2.99 (ddd, J=4.8, 11.6, 14.0 Hz, 1H), 1.76–1.90 (m, 3H), 1.62–1.73 (m, 2H), 1.42–1.59 (m, 4H), 1.28–1.38 (m, 3H), 1.14–1.26 (m, 2H), 1.06 (dt, J=3.2, 13.2 Hz, 1H), 0.94 (t, J=8.0 Hz, 9H), 0.87 (s, 3H), 0.86 (d, J=6.0 Hz, 3H), 0.54 (q, J=8.0 Hz, 6H); $^{13}$C NMR (100 MHz, CDCl$_3$) δ 139.0, 138.6, 134.0, 131.3, 130.0, 127.1, 69.1, 55.8, 53.7, 52.9, 42.1, 40.6, 34.4, 34.2, 28.1, 27.0, 22.8, 18.2, 17.5, 13.4, 6.9, 4.8; IR (thin film) 2950, 2875, 1455, 1370, 1322, 1156, 1091 cm$^{-1}$; HRMS [M+Na] calc'd 555.1893 for C$_{26}$H$_{42}$Cl$_2$O$_3$SSiNa. found: 555.1886.

(f) (+)-(Triethylsilyl)-oxy-p-[3-(tert-Butyldimethylsiloxy)isopentyl]phenyl sulfone: By replacing methyl phenyl sulfone with p-(3-(tert-Butyldimethyl-siloxy)isopentyl)phenyl methyl sulfone. The crude mixture was purified by flash chromatography (EtOAc:Hex=1:19 to 1:15) to afford 107.7 mg (94%) of C24-p-[3-(tert-Butyldimethylsiloxy)isopentyl] phenyl sulfone. R$_f$ 0.39 (1:9-EtOAc:Hex); $[\alpha]D^{26}$+21.3 (c 0.97, CHCl$_3$); $^1$H NMR (400 MHz, CDCl$_3$) δ 7.82–7.85 (m, 2H), 7.54–7.57 (m, 2H), 4.00 (m, 1H), 3.11 (ddd, J=4.0, 12.0, 13.6 Hz, 1H), 2.98 (ddd, J=4.8, 11.2, 13.6 Hz, 1H), 1.75–1.96 (m, 7H), 1.43–1.66 (m, 5H), 1.24–1.35 (m, 5H), 1.00–1.20 (m, 2H), 1.00 (s, 9H), 0.93 (s, 9H), 0.84 (d, J=6.0 Hz, 3H), 0.84 (s, 3H), 0.63 (t, J=7.2 Hz, 6H), 0.53 (q, J=8.0 Hz, 6H), 0.16 (s, 6H); $^{13}$C NMR (100 MHz, CDCl$_3$) δ 152.6, 136.5, 127.6, 126.8, 81.5, 69.2, 55.8, 53.6, 52.9, 42.1, 40.6, 35.65, 35.62, 34.5, 34.2, 28.3, 26.9, 26.2, 22.8, 18.9, 18.3, 17.6, 13.5, 8.2, 6.9, 4.9, –2.1; IR (thin film) 2952, 2877, 1462, 1318, 1256, 1151, 1025, 836, 800, 771 cm$^{-1}$; HRMS [M+Na] calc'd 687.4269 for C$_{37}$H$_{68}$O$_4$SSi$_2$Na. found: 687.4293.

(g) (+)-(Triethylsilyl)-oxy-p-Acetalphenyl sulfone: By replacing methyl phenyl sulfone with p-acetalphenyl methyl sulfone (Example 2). The crude mixture was purified by flash chromatography (EtOAc:Hex=1:4) to afford 83.5 mg (74%) of C24-p-acetalphenyl sulfone. R$_f$ 0.26 (1:4-EtOAc:Hex); $[\alpha]D^{26}$+33.2 (c 1.10, CHCl$_3$); $^1$H NMR (400 MHz, CDCl$_3$) δ 7.91–7.93 (m, 2H), 7.67–7.69 (m, 2H), 5.89 (s, 1H), 4.05–4.15 (m, 4H), 4.01 (m, 1H), 3.14 (ddd, J=4.0, 12.0, 13.6 Hz, 1H), 2.97 (ddd, J=4.8, 11.6, 13.6 Hz, 1H), 1.75–1.89 (m, 3H), 1.60–1.70 (m, 2H), 1.40–1.58 (m, 3H), 1.28–1.36 (m, 3H), 1.02–1.21 (m, 4H), 0.93 (t, J=8.4 Hz, 9H), 0.86 (s, 3H), 0.83 (d, J=6.0 Hz, 3H), 0.54 (q, J=8.4 Hz, 6H); $^{13}$C NMR (100 MHz, CDCl$_3$) δ 143.8, 139.7, 128.1, 127.2, 102.4, 69.1, 65.4, 55.9, 53.6, 52.9, 42.1, 40.6, 34.4, 34.2, 28.1, 26.9, 22.8, 18.2, 17.5, 13.4, 6.8, 4.8; IR (thin film) 2950, 2876, 1316, 1149, 1085, 1018, 973, 948, 744, 725, 547 cm$^{-1}$; HRMS [M+Na] calc'd 559.2884 for C$_{29}$H$_{48}$O$_5$SSiNa. found: 559.2930.

In a like manner, the following additional compounds can be prepared:

(h) (Triethylsilyl)-oxy-(4-methoxyphenyl) sulfone: By replacing methyl phenyl sulfone with methyl (4-methoxyphenyl) sulfone (Example 1a);

(i) (Triethylsilyl)-oxy-(4-nitrophenyl) sulfone: By replacing methyl phenyl sulfone with methyl (4-nitrophenyl) sulfone (Example 1b); and (j) (Triethylsilyl)-oxy-(4-trifluoromethyl phenyl) sulfone: By replacing methylpheny sulfone with methyl (4-trifluoromethyl phenyl) sulfone (Example 1c).

Example 4

C,D-Ring Ketones III (a) (+)-Ketophenyl sulfone

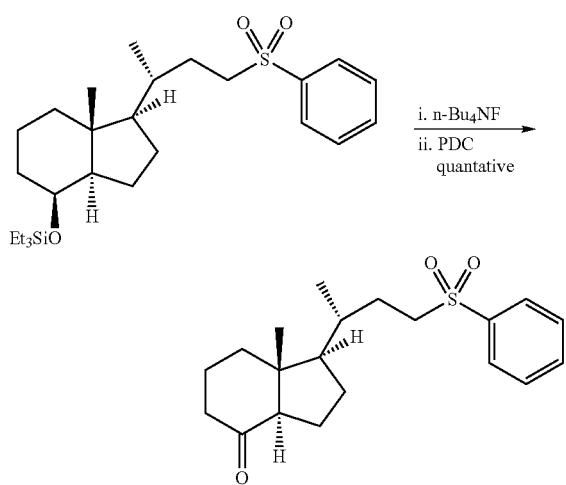

To a solution of (triethylsilyl)-oxyphenyl sulfone (Example 3a, 86 mg, 0.185 mmol) in THF (~0.7 M) was added a solution of tetrabutylammonium fluoride (TBAF, 740 μL, 0.740 mmol, 1.0 M in THF). The reaction mixture was stirred for 18 h and concentrated under reduced pressure to a brown syrup. This brown syrup was then dissolved in $CH_2Cl_2$ and treated with pyridinium dichromate (PDC, 290 mg, 0.555 mmol) and celite® (109 mg) for 12 h. The contents of the flask were then passed through a 1" plug of silica gel, rinsed with EtOAc (3×), concentrated, and purified by flash chromatography (35→40% EtOAc/hexanes) or preparative-plate chromatography (50% EtOAc/hexanes) to afford pure C,D-ring ketone (67 mg) in quantitative yield as a colorless oil: $[\alpha]_D^{25}$+17.7 (c 4.3, $CHCl_3$); $^1H$ NMR (400 MHz, $CDCl_3$) δ 7.92–7.84 (m, 2H), 7.67–7.60 (tt, J=7.6, 1.7 Hz, 1H), 7.59–7.51 (m, 2H), 3.16–3.04 (m, 1H), 3.03–2.91 (m, 1H), 2.45–2.33 (dd, J=11.4, 7.4 Hz, 1H), 2.29–2.11 (m, 2H), 2.07–1.91 (m, 2H), 0.89 (d, J=6.4 Hz, 3H), 0.52 (s, 3H); $^{13}C$ NMR (100 MHz, $CDCl_3$) δ 139.0, 133.6, 129.2, 127.9, 61.6, 55.7, 53.4, 49.6, 40.7, 38.7, 34.3, 28.1, 27.1, 23.8, 18.9, 18.3, 12.4; IR (neat) 2956, 2875, 1709, 1446, 1306, 1145, 1086, 747, 690 $cm^{-1}$; HRMS: calcd for $C_{20}H_{28}O_5S$+Na, 371.1657, found 371.1664.

In a like manner, the following additional compounds were prepared:

(b) (+)-Keto-(4-fluorophenyl) Sulfone: By replacing (triethylsilyl)-oxyphenyl sulfone with (triethylsilyl)-oxy-(4-fluorophenyl) sulfone (Example 3b). The reaction mixture was directly purified by short path flash chromatography ($CH_2Cl_2$ then EtOAc:Hex=1:2) to give 50.5 mg (85% for 2 steps) of keto-p-fluorophenyl sulfone. $R_f$ 0.30 (1:2-EtOAc:Hex); $[\alpha]D^{26}$+11.5 (c 0.96, $CHCl_3$); $^1H$ NMR (400 MHz, $CDCl_3$) δ 7.90–7.95 (m, 2H), 7.24–7.28 (m, 2H), 3.13 (ddd, J=4.4, 12.0, 13.6 Hz, 1H), 3.00 (ddd, J=4.8, 11.2, 14.0 Hz, 1H), 2.43 (dd, J=7.6, 11.6 Hz, 1H), 2.17–2.32 (m, 2H), 1.97–2.08 (m, 2H), 1.67–1.94 (m, 4H), 1.45–1.60 (m, 4H), 1.39 (q, J=9.2 Hz, 1H), 1.27 (m, 1H), 0.93 (d, J=6.0 Hz, 3H), 0.61 (s, 3H); $^{13}C$ NMR (100 MHz, $CDCl_3$) δ 211.4, 165.7 (d, J=255.1), 135.1 (d, J=3.0), 130.8 (d, J=9.9), 116.6 (d, J=22.8), 61.6, 55.8, 53.6, 49.7, 40.8, 38.7, 34.4, 28.2, 27.2, 23.8, 18.9, 18.3, 12.4; IR (thin film) 2957, 2876, 1710, 1591, 1494, 1316, 1289, 1232, 1144, 1086 $cm^{-1}$; HRMS [M+Na] calc'd 389.1557 for $C_{20}H_{27}FO_3SNa$. found: 389.1547.

(c) (+)-Keto-(4-chlorophenyl) Sulfone: By replacing (triethylsilyl)-oxyphenyl sulfone with (triethylsilyl)-oxy-(4-chlorophenyl) sulfone (Example 3c). The reaction mixture was directly purified by short path flash chromatography ($CH_2Cl2$ then EtOAc:Hex=1:2) to give 56.2 mg (82% for 2 steps) of keto-p-chlorophenyl sulfone. $R_f$ 0.34 (1:2-EtOAc:Hex); $[\alpha]D^{26}$+12.5 (c 0.97, $CHCl_3$); $^1H$ NMR (400 MHz, $CDCl_3$) δ 7.83–7.86 (m, 2H), 7.54–7.58 (m, 2H), 3.13 (ddd, J=4.8, 12.0, 14.0 Hz, 1H), 3.00 (ddd, J=4.8, 11.2, 14.0 Hz, 1H), 2.43 (m, 1H), 2.17–2.31 (m, 2H), 1.97–2.08 (m, 2H), 1.68–1.94 (m, 4H), 1.22–1.59 (m, 4H), 0.93 (d, J=6.4 Hz, 3H), 0.61 (s, 3H); $^{13}C$ NMR (100 MHz, $CDCl_3$) δ 211.4, 140.4, 137.5, 129.6, 129.5, 61.7, 55.8, 53.6, 49.7, 40.8, 38.8, 34.4, 28.2, 27.2, 23.8, 18.9, 18.3, 12.4; IR (thin film) 2957, 2876, 1710, 1315, 1149, 1088 $cm^{-1}$; HRMS [M+Na] calc'd 405.1267 for $C_{20}H_{27}ClO_3SNa$. found: 405.1263.

(d) (+)-Keto-(4-methylphenyl) Sulfone: By replacing (triethylsilyl)-oxyphenyl sulfone with (triethylsilyl)-oxy-(4-methylphenyl) sulfone (Example 3d). The reaction mixture was directly purified by short path flash chromatography ($CH_2Cl_2$ then EtOAc:Hex=1:2) to give 57.4 mg (89% for 2 steps) of keto-p-fluorophenyl. $R_f$ 0.26 (1:2-EtOAc:Hex); $[\alpha]D^{26}$+9.4 (c 1.15, $CHCl_3$); $^1H$NMR (400 MHz, $CDCl_3$) δ 7.77–7.79 (m, 2H), 7.36–7.38 (m, 2H), 3.11 (ddd, J=4.4, 12.0, 13.6 Hz, 1H), 2.98 (ddd, J=4.8, 11.2, 13.6 Hz, 1H), 2.46 (s, 3H), 2.42 (dd, J=8.0, 12.0 Hz, 1H), 2.16–2.31 (m, 2H), 1.96–2.08 (m, 2H), 1.66–1.94 (m, 4H), 1.44–1.58 (m, 4H), 1.38 (q, J=9.2 Hz, 1H), 1.25 (m, 1H), 0.92 (d, J=6.4 Hz, 3H), 0.60 (s, 3H); $^{13}C$ NMR (100 MHz, $CDCl_3$) δ 211.5, 144.6, 136.0, 129.8, 127.9, 61.6, 55.8, 53.5, 49.6, 40.7, 38.7, 34.3, 28.2, 27.1, 23.8, 21.6, 18.9, 18.3, 12.4; IR (thin film) 2956, 2875, 1710, 1314, 1143, 1087 $cm^{-1}$; HRMS [M+Na] calc'd 385.1808 for $C_{21}H_{30}O_3SNa$. found: 385.1825.

(e) (+)-Keto-(3,4-dichlorophenyl) Sulfone: By replacing (triethylsilyl)-oxyphenyl sulfone with (triethylsilyl)-oxy-(3,4-dichlorophenyl) sulfone (Example 3e). The reaction mixture was directly purified by short path flash chromatography ($CH_2Cl_2$ then EtOAc:Hex=1:2) to give 47.3 mg (94% for 2 steps) of keto-3,4-dichlororophenyl sulfone. $R_f$ 0.39 (1:2-EtOAc:Hex); $[\alpha]D^{26}$+10.9 (c 0.99, $CHCl_3$); $^1H$ NMR (400 MHz, $CDCl_3$) δ 8.00 (dd, J=0.4, 2.0 Hz, 1H), 7.73 (dd, J=2.0, 8.4 Hz, 1H), 7.67 (dd, J=0.4, 8.4 Hz, 1H), 3.14 (ddd, J=4.8, 11.6, 14.0 Hz, 1H), 3.01 (ddd, J=4.8, 11.2, 14.0 Hz, 1H), 2.44 (dd, J=7.6, 12.0 Hz, 1H), 2.17–2.32 (m, 2H), 1.98–2.09 (m, 2H), 1.69–1.95 (m, 4H), 1.46–1.60 (m, 4H), 1.40 (q, J=9.2 Hz, 1H), 1.29 (m, 1H), 0.94 (d, J=6.4 Hz, 3H), 0.62 (s, 3H); $^{13}C$ NMR (100 MHz, $CDCl_3$) δ 211.4, 138.85, 138.81, 134.0, 131.4, 130.0, 127.0, 61.7, 55.8, 53.6, 49.7, 40.8, 38.8, 34.5, 28.0, 27.3, 23.8, 18.9, 18.3, 12.4; IR (thin film) 3086, 2957, 2876, 1710, 1455, 1370, 1317, 1150, 1094, 1034, 824, 753, 676, 634 $cm^{-1}$; HRMS [M+Na] calc'd 439.0872 for $C_{20}H_{26}Cl_2O_3SNa$. found: 439.0832.

(f) (+)-Keto-p-[3-(tert-Butyldimethylsiloxy)isopentyl] phenyl Sulfone: By replacing (triethylsilyl)-oxyphenyl sulfone with p-[3-(tert-butyldimethylsiloxy)isopentyl]phenyl sulfone (Example 3f). The reaction mixture was directly purified by short path flash chromatography ($CH_2Cl_2$ then EtOAc:Hex=1:2) to give 75.8 mg (97% for 2 steps) of keto-p-(3-(tert-Butyldimethylsiloxy)isopentyl)phenyl sulfone. $R_f$ 0.53 (1:2-EtOAc:Hex); $[\alpha]D^{26}$+3.6 (c 1.64, $CHCl_3$); $^1H$ NMR (400 MHz, $CDCl_3$) δ 7.83–7.85 (m, 2H), 7.55–7.58 (m, 2H), 3.12 (ddd, J=4.0, 12.0, 14.0 Hz, 1H), 3.00 (ddd, J=4.8, 10.8, 13.6 Hz, 1H), 2.41 (dd, J=7.6, 11.2, 1H), 2.16–2.30 (m, 2H), 1.79–2.07 (m, 8H), 1.63–1.74 (m, 2H), 1.45–1.57 (m, 3H), 1.34–1.42 (m, 1H), 1.14–1.28 (m, 2H), 1.00 (s, 9H), 0.92 (d, J=6.8 Hz, 3H), 0.62 (t, J=7.2 Hz, 6H), 0.58 (s, 3H), 0.17 (s, 6H); $^{13}$C NMR (100 MHz, CDCl$_3$) δ 211.4, 152.8, 136.3, 127.5, 126.8, 81.4, 61.6, 55.7, 53.4, 49.6, 40.8, 38.7, 35.59, 35.56, 27.1, 26.2, 23.8, 18.9, 18.8, 18.3, 12.4, 8.2, -2.2; IR (thin film) 2956, 1713, 1458, 1315, 1256, 1147, 1062, 836, 798, 771 cm$^{-1}$; HRMS [M+Na] calc'd 571.3248 for C$_{31}$H$_{52}$O$_4$SSiNa. found: 571.3284

(g) (+)-Keto-p-Acetalphenyl Sulfone: By replacing (triethylsilyl)-oxyphenyl sulfone with (+)-(triethylsilyl)-oxy-p-Acetalphenyl sulfone (Example 3g). The reaction mixture was directly purified by short path flash chromatography (CH$_2$Cl$_2$ then EtOAc:Hex=1:1) to give 66 mg (100% for 2 steps) of keto-p-acetalphenyl sulfone. R$_f$ 0.38 (1:1-EtOAc: Hex); [α]D$^{26}$+11.1 (c 0.97, CHCl$_3$); $^1$H NMR (400 MHz, CDCl$_3$) δ 7.91–7.93 (m, 2H), 7.68–7.70 (m, 2H), 5.88 (s, 1H), 4.06–4.15 (m, 4H), 3.12 (ddd, J=4.4, 11.6, 14.0 Hz, 1H), 2.99 (ddd, J=4.8, 11.2, 14.0 Hz, 1H), 2.42 (dd, J=7.6, 12.0 Hz, 1H), 2.17–2.31 (m, 2H), 1.97–2.06 (m, 2H), 1.66–1.94 (m, 4H), 1.44–1.58 (m, 3H), 1.37 (q, J=9.6 Hz, 1H), 0.92 (d, J=6.4 Hz, 3H), 0.60 (s, 3H); $^{13}$C NMR (100 MHz, CDCl$_3$) δ 211.4, 143.9, 139.6, 128.0, 127.3, 102.3, 65.4, 61.6, 55.8, 53.5, 49.6, 40.7, 38.7, 34.4, 28.1, 27.1, 23.8, 18.9, 18.2, 12.4; IR (thin film) 2957, 2879, 1709, 1381, 1145, 1086, 943, 754, 549 cm$^{-1}$; HRMS [M+Na] calc'd 443.1863 for C$_{23}$H$_{32}$O$_5$Na. found: 443.1843.

In a like manner, the following additional compounds can be prepared:

(h) Keto-(4-methoxyphenyl) sulfone: By replacing (triethylsilyl)-oxyphenyl sulfone with (triethylsilyl)-oxy-(4-methoxyphenyl) sulfone (Example 3h);

(i) Keto-(4-nitrophenyl) sulfone: By replacing (triethylsilyl)-oxyphenyl sulfone with (triethylsilyl)-oxy-(4-nitrophenyl) sulfone (Example 3i); and (j) Keto-(4-trifluoromethylphenyl) sulfone: By replacing (triethylsilyl)-oxyphenyl sulfone with (triethylsilyl)-oxy-(4-trifluoromethylphenyl) sulfone (Example 3j).

Example 5

24-Phenyl Sulfone Vitamin-D$_3$ Analogs (I)

(a)

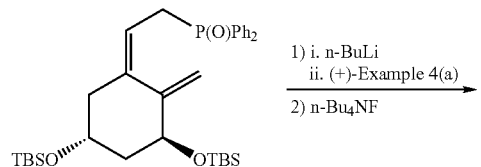

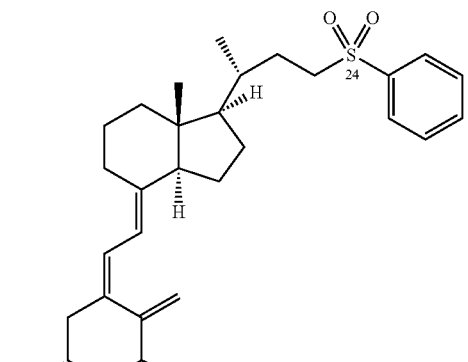

I(a)

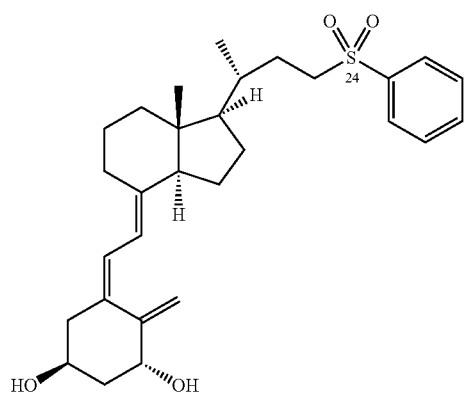

I(b)

Prior to reaction, the phosphine oxide (Posner, G. H. et al. *J. Med. Chem.* 1992, 35, 3280–3287) and C,D-ring ketone of Example 3a were azeotrophically dried with benzene and left under vacuum for 48 h. A solution of n-BuLi in hexanes (58 μL, 0.086 mmol, 1.48 M in hexanes) was added dropwise to a cold (−78° C.) solution of phosphine oxide (50 mg, 0.086 mmol) in THF (1.30 mL) under dry argon. The resulting deep red solution was stirred for 1 h, at which time a cold (−78° C.) solution of C,D-ring ketone (Example 3a, 15 mg, 0.043 mmol) in THF (1.2 mL) was added dropwise via cannula. The resulting solution was stirred at −78° C. in the dark for approximately 3 h, then slowly warmed to −40° C. over 2 h. The reaction mixture was quenched with H$_2$O (1 mL), warmed to rt, extracted with Et$_2$O (3×10 mL), washed with brine, dried over MgSO$_4$, filtered, concentrated, and purified by silica gel column chromatography (20→50% EtOAc/hexanes) to afford the coupled products as a clear oil. This oil was immediately dissolved in THF (5.0 mL) and treated with TBAF (215 μL, 0.215 mmol, 1.0 M in THF) in the dark for 16 h. Concentration of the reaction mixture and column chromatography (EtOAc) yielded a mixture of diastereomers. This diastereomeric mixture was separated by HPLC (CHIRALCEL® OJ semipreparative column, 15% EtOH/hexanes, 3 mL/min) giving enantiomerically pure, hybrid vitamin-$D_3$ analogs I(a) (9 mg, 43%, 1α,3β, $R_f$ 37.2 min) and I(b) (4 mg, 19%, 1β,3α, $R_f$ 31.7 min). I(a) (1α,3β): $[α]_D^{25}$+31.8 (c 8.3, $CHCl_3$); $^1H$ NMR (400 MHz, $CDCl_3$) δ 7.95–7.88 (m, 2H), 7.70–7.62 (tt, J=7.6, 1.7 Hz, 1H), 7.62–7.53 (m, 2H), 6.35 (d, J=11.2 Hz, 1H), 5.99 (d, J=11.2 Hz, 1H), 5.32 (m, 1H), 4.98 (m, 1H), 4.47–4.38 (m, 1H), 4.27–4.17 (m, 1H), 3.18–3.06 (m, 1H), 3.06–2.92 (m, 1H), 2.86–2.75 (dd, J=12.6, 4.2 Hz, 1H), 2.64–2.53 (dd, J=13.6, 3.2 Hz, 1H), 2.36–2.25 (dd, J=13.4, 6.6 Hz, 1H), 0.88 (d, J=6.0 Hz, 3H), 0.49 (s, 3H); $^{13}C$ NMR (100 MHz, $CDCl_3$) δ 147.6, 142.5, 139.2, 133.6, 133.2, 129.2, 128.0, 124.8, 117.2, 111.8, 70.8, 66.8, 56.1, 55.7, 53.6, 45.8, 45.2, 42.8, 40.3, 35.0, 28.9, 28.2, 27.3, 23.4, 22.1, 18.5, 12.0; IR (neat) 3647–3119, 3020, 2943, 2871, 1446, 1304, 1216, 1143, 1086, 1055, 753, 688, 534 $cm^{-1}$; HRMS: calcd for $C_{29}H_{40}O_4$+Na, 507.2545, found 507.2507; UV pending. I(b) (1β,3α): $[α]_D^{25}$+11.4 (c 2.7, $CHCl_3$); $^1H$ NMR (400 MHz, $CDCl_3$) δ 7.95–7.87 (m, 2H), 7.70–7.62 (tt, J=7.6, 1.7 Hz, 1H), 7.61–7.53 (m, 2H), 6.37 (d, J=11.2 Hz, 1H), 5.99 (d, J=11.2 Hz, 1H), 5.31 (m, 1H), 4.98 (m, 1H), 4.47–4.38 (m, 1H), 4.27–4.16 (m, 1H), 3.18–3.06 (m, 1H), 3.06–2.92 (m, 1H), 2.86–2.75 (dd, J=12.6, 4.2 Hz, 1H), 2.65–2.54 (dd, J=13.6, 3.2 Hz, 1H), 2.35–2.24 (dd, J=13.4, 6.6 Hz, 1H), 0.88 (d, J=6.4 Hz, 3H), 0.50 (s, 3H); 13C NMR (100 MHz, $CDCl_3$) δ 147.2, 142.6, 139.2, 133.6, 133.0, 129.2, 128.0, 124.8, 117.2, 112.5, 71.3, 66.8, 56.1, 55.7, 53.6, 45.8, 45.4, 42.8, 40.3, 35.0, 28.9, 28.2, 27.3, 23.4, 22.1, 18.5, 12.0; IR (neat) 3636–3125, 3066, 3019, 2936, 2866, 1447, 1379, 1306, 1215, 1144, 1085, 1053, 956, 917, 800, 753, 689, 667, 601, 534 $cm^{-1}$; HRMS: calcd for $C_{29}H_{40}O_4$+Na, 507.2545, found 507.2533.

In a like manner, the following additional compounds were prepared:

(b)

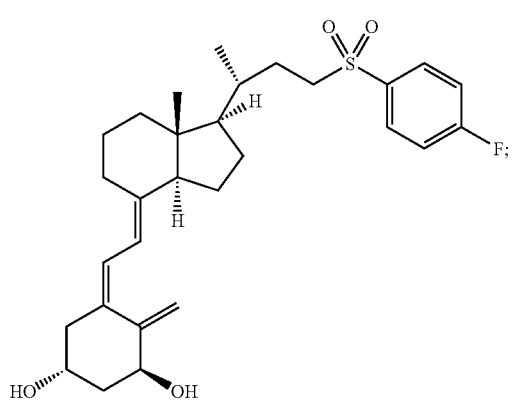

I(c)

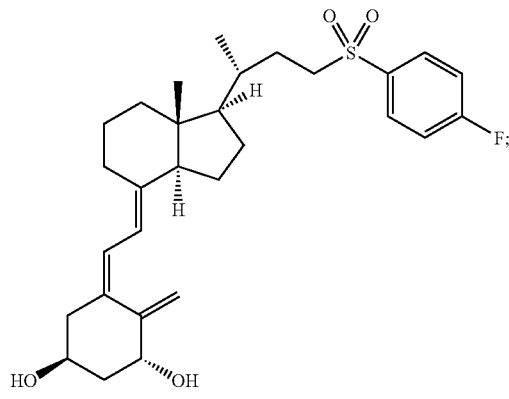

I(d)

by replacing the compound from Example 4a with the compound of Example 4b. The diastereomers were purified by HPLC (Chiralcel OJ column, 25% EtOH in Hexanes, 2.5 mL/min, 254 nm) to afford 14 mg (55%) of (+)-I(c) (1α,3β, $t_R$ 34.2 min) as a viscous oil and 5.3 mg (21%) of (+)-I(d) (1β,3α, $t_R$ 27.0 min) as a viscous oil. (+)-I(c): $R_f$ 0.61 (EtOAc); $[α]D^{26}$+32.3 (c 1.68, $CHCl_3$); $^1H$ NMR (400 MHz, $CDCl_3$) δ 7.91–7.94 (m, 2H), 7.23–7.27 (m, 2H), 6.36 (d, J=11.2 Hz, 1H), 6.00 (d, J=11.2 Hz, 1H), 5.32 (m, 1H), 4.98 (m, 1H), 4.43 (m, 1H), 4.23 (m, 1H), 3.13 (ddd, J=4.8, 11.6, 14.0 Hz, 1H), 2.99 (ddd, J=4.8, 11.2, 14.0 Hz, 1H), 2.81 (dd, J=4.0 12.4 Hz, 1H), 2.59 (dd, J=2.8, 13.2 Hz, 1H), 2.31 (dd, J=6.4, 13.2 Hz, 1H), 1.89–2.04 (m, 4H), 1.74–1.87 (m, 2H), 1.62–1.73 (m, 4H), 1.44–1.57 (m, 5H), 1.15–1.30 (m, 3H), 0.89 (d, J=6.4 Hz, 3H), 0.51 (s, 3H); $^{13}C$ NMR (100 MHz, $CDCl_3$) δ 165.8 (d, 255.1 Hz), 147.6, 142.4, 135.2 (d, 3.0 Hz), 133.2, 130.9 (d, 9.1 Hz), 124.8, 117.3, 116.6 (d, 22.0 Hz), 111.8, 70.8, 66.8, 56.2, 55.7, 53.8, 45.8, 45.2, 42.8, 40.3, 35.0, 28.9, 28.3, 27.3, 23.4, 22.1, 18.5, 12.0; IR (thin film) 3380, 2946, 2874, 1591, 1494, 1315, 1288, 1231, 1143, 1086, 1054, 840, 754, 668 $cm^{-1}$; HRMS [M+Na] calc'd 525.2445 for $C_{29}H_{39}FO_4SNa$. found: 525.2462; UV (MeOH) $λ_{max}$ 264 nm (ε 14000). (+)-I(d): $R_f$ 0.61 (EtOAc); $[α]D^{26}$+21.5 (c 0.57, $CHCl_3$); $^1H$ NMR (400 MHz, $CDCl_3$) δ 7.90–7.95 (m, 2H), 7.25–7.28 (m, 2H), 6.37 (d, J=11.6 Hz, 1H), 6.00 (d, J=11.2 Hz, 1H), 5.31 (dd, J=1.2, 2.0 Hz, 1H), 4.99 (d, J=1.2 Hz, 1H), 4.44 (m, 1H), 4.22 (m, 1H), 3.13 (ddd, J=4.4, 12.0, 14.0 Hz, 1H), 2.99 (ddd, J=4.8, 11.6, 14.0 Hz, 1H), 2.82 (dd, J=4.4 12.8 Hz, 1H), 2.61 (dd, J=4.0, 13.6 Hz, 1H), 2.29 (dd, J=7.6, 13.2 Hz, 1H), 1.90–2.03 (m, 4H), 1.74–1.87 (m, 2H), 1.44–1.73 (m, 9H), 1.15–1.30 (m, 3H), 0.89 (d, J=6.4 Hz, 3H), 0.51 (s, 3H); $^{13}C$ NMR (100 MHz, $CDCl_3$) δ 165.8 (d, 255.9 Hz), 147.3, 142.5, 135.3 (d, 3.0 Hz), 133.1, 130.9 (d, 9.9 Hz), 124.8, 117.3, 116.6 (d, 22.8 Hz), 112.5, 71.3, 66.8, 56.1, 55.7, 53.8, 45.8, 45.4, 42.8, 40.3, 35.0, 28.9, 28.3, 27.3, 23.4, 22.2, 18.5, 12.0; IR (thin film) 3382, 2929, 2873, 1591, 1494, 1315, 1288, 1232, 1143, 1086, 1053, 840, 754, 569 $cm^{-1}$; HRMS [M+Na] calc'd 525.2445 for $C_{29}H_{39}FO_4SNa$. found: 525.2474; UV (MeOH) $I_{max}$ 258 nm (ε 12000).

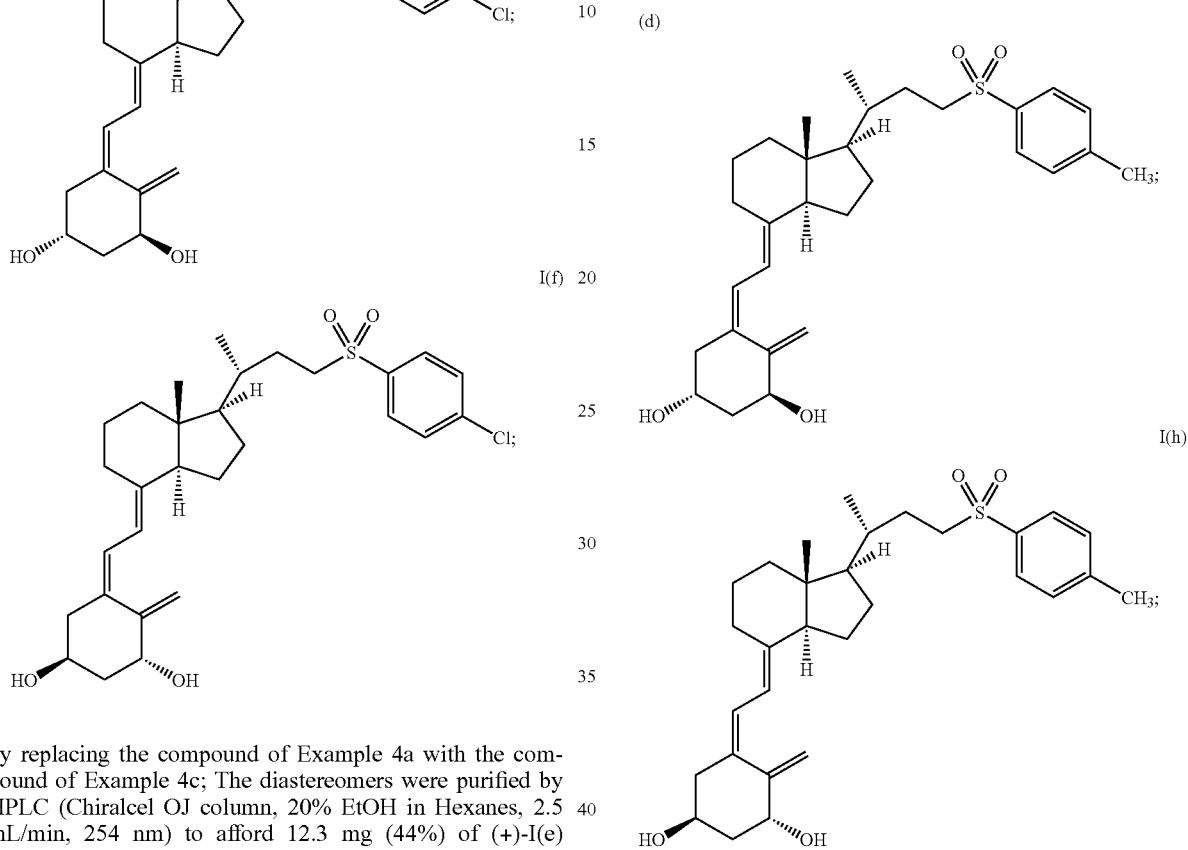

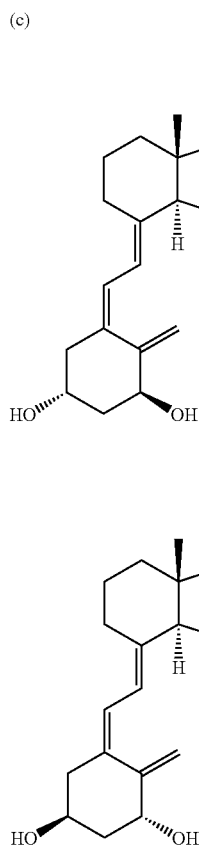

by replacing the compound of Example 4a with the compound of Example 4c; The diastereomers were purified by HPLC (Chiralcel OJ column, 20% EtOH in Hexanes, 2.5 mL/min, 254 nm) to afford 12.3 mg (44%) of (+)-I(e) (1α,3β, $t_R$ 29.6 min) as a viscous oil and 3.9 mg (14%) of (+)-I(f) (1β,3α, $t_R$ 25.8 min) as a viscous oil. (+)-I(e): $R_f$ 0.58 (EtOAc); $[α]D^{26}$+33.5 (c 0.88, CHCl$_3$); $^1$HNMR (400 MHz, CDCl$_3$) δ 7.83–7.86 (m, 2H), 7.54–7.57 (m, 2H), 6.36 (d, J=11.2, 1H), 6.00 (d, J=11.2 Hz, 1H), 5.33 (s, 1H), 4.99 (s, 1H), 4.43 (m, 1H), 4.23 (m, 1H), 3.13 (ddd, J=4.4, 12.0, 14.0 Hz, 1H), 2.99 (ddd, J=4.8, 11.6, 14.0 Hz, 1H), 2.82 (dd, J=4.0 12.4, 1H), 2.59 (dd, J=3.6, 13.6 Hz, 1H), 2.31 (dd, J=6.8, 13.6 Hz, 1H), 1.44–2.05 (m, 15H), 1.16–1.30 (m, 3H), 0.89 (d, J=6.4 Hz, 3H), 0.51 (s, 3H); $^{13}$C NMR (100 MHz, CDCl$_3$) δ 147.6, 142.5, 140.4, 137.7, 133.2, 129.6, 129.5, 124.8, 117.3, 111.8, 70.8, 66.8, 56.2, 55.7, 53.7, 45.8, 45.2, 42.8, 40.3, 35.0, 28.9, 28.3, 27.4, 23.4, 22.2, 18.5, 12.0; IR (thin film) 3382, 2926, 1583, 1313, 1148, 1088, 756 cm$^{-1}$; HRMS [M+Na] calc'd 541.2150 for C$_{29}$H$_{39}$ClO$_4$SNa. found: 541.2139; UV (MeOH) $λ_{max}$ 264 nm (ε 14000). (+)-I(f): $R_f$ 0.58 (EtOAc); $[α]D^{26}$+18.4 (c 0.42, CHCl$_3$); $^1$HNMR (400 MHz, CDCl$_3$) δ 7.83–7.86 (m, 2H), 7.54–7.57 (m, 2H), 6.37 (d, J=11.2, 1H), 6.00 (d, J=11.2 Hz, 1H), 5.32 (m, 1H), 4.99 (m, 1H), 4.44 (m, 1H), 4.22 (m, 1H), 3.13 (ddd, J=4.4, 11.6, 14.0 Hz, 1H), 2.99 (ddd, J=4.8, 11.2, 14.0 Hz, 1H), 2.82 (dd, J=4.0, 12.4, 1H), 2.61 (dd, J=4.0, 12.8 Hz, 1H), 2.30 (dd, J=7.2, 13.2 Hz, 1H), 1.90–2.04 (m, 3H), 1.72–1.88 (m, 3H), 1.44–1.67 (m, 9H), 1.20–1.30 (m, 3H), 0.89 (d, J=6.4 Hz, 3H), 0.51 (s, 3H); $^{13}$C NMR (100 MHz, CDCl$_3$) δ 147.3, 142.5, 140.4, 137.7, 133.1, 129.6, 129.5, 124.8, 117.3, 112.5, 71.3, 66.8, 56.1, 55.7, 53.7, 45.8, 45.4, 42.8, 40.3, 35.0, 28.9, 28.3, 27.3, 23.4, 22.2, 18.5, 12.0; IR (thin film) 3366, 2926, 1583, 1475, 1314, 1148, 1089, 758, 668, 630 cm$^{-1}$; HRMS [M+Na] calc'd 541.2150 for C$_{29}$H$_{39}$ClO$_4$SNa. found: 541.2112; UV (MeOH) $λ_{max}$ 253 nm (ε 8700).

by replacing the compound of Example 4a with the compound of Example 4d. The diastereomers were purified by HPLC (Chiralcel OJ column, 17% EtOH in Hexanes, 2.5 mL/min, 254 nm) to afford 6.2 mg (53%) of (+)-I(g) (1α,3β, $t_R$ 37.7 min) as a viscous oil and 2.0 mg (17%) of (+)-I(h) (1β,3α, $t_R$ 31.4 min) as a viscous oil. (+)-I(g): $R_f$ 0.61 (EtOAc); $[α]D^{26}$+38.6 (c 0.70, CHCl$_3$); $^1$H NMR (400 MHz, CDCl$_3$) δ 7.77–7.80 (m, 2H), 7.35–7.37 (m, 2H), 6.36 (d, J=11.2 Hz, 1H), 6.00 (d, J=11.6 Hz, 1H), 5.32 (dd, J=1.6, 1.6 Hz, 1H), 4.99 (dd, J=1.2, 1.2 Hz, 1H), 4.43 (m, 1H), 4.23 (m, 1H), 3.11 (ddd, J=4.8, 12.0, 14.0 Hz, 1H), 2.97 (ddd, J=4.8, 11.2, 13.6 Hz, 1H), 2.81 (dd, J=4.4, 12.4 Hz, 1H), 2.59 (dd, J=4.0, 13.2 Hz, 1H), 2.46 (s, 3H), 2.31 (dd, J=6.4, 13.2 Hz, 1H), 1.89–2.03 (m, 4H), 1.74–1.86 (m, 2H), 1.43–1.72 (m, 8H), 1.17–1.30 (m, 4H), 0.88 (d, J=6.0 Hz, 3H), 0.50 (s, 3H); $^{13}$C NMR (100 MHz, CDCl$_3$) δ 147.6, 144.5, 142.6, 136.3, 133.2, 129.8, 128.0, 124.8, 117.2, 111.8, 70.8, 66.8, 56.2, 55.7, 53.7, 45.8, 45.2, 42.8, 40.3, 35.0, 28.9, 28.3, 27.3, 23.4, 22.1, 21.6, 18.5, 12.0; IR (thin film) 3392, 2926, 2873, 1597, 1448, 1313, 1302, 1285, 1142, 1087, 1054, 754, 668 cm$^{-1}$; HRMS [M+Na] calc'd 521.2696 for C$_{30}$OH$_{42}$O$_4$SNa. found: 521.2662; UV (MeOH) $λ_{max}$ 262 nm (ε 18000). (+)-I(h): $R_f$ 0.61 (EtOAc); $[α]D^{26}$+22.8 (c 0.20, CHCl$_3$); $^1$H NMR (400 MHz, CDCl$_3$) δ 7.77–7.79 (m, 2H), 7.35–7.37 (m, 2H), 6.37 (d, J=11.6 Hz, 1H), 5.99 (d, J=10.8 Hz, 1H), 5.31 (dd, J=1.2, 1.2 Hz, 1H), 4.99 (m, 1H), 4.44 (m, 1H), 4.22 (m, 1H), 3.11 (ddd, J=4.0, 12.0, 14.0 Hz, 1H), 2.97 (ddd, J=4.8, 11.2, 14.0 Hz, 1H), 2.81 (dd, J=4.8, 12.8 Hz, 1H), 2.61 (dd, J=4.0, 13.6 Hz, 1H), 2.46 (s, 3H), 2.29 (dd, J=7.6, 13.2 Hz, 1H), 1.90–2.04 (m, 3H), 1.74–1.87 (m, 2H), 1.43–1.70 (m, 9H), 1.17–1.29 (m, 4H), 0.88 (d, J=6.4 Hz, 3H), 0.50 (s, 3H); $^{13}$C NMR (100 MHz, CDCl$_3$) δ 147.3, 144.5, 142.6, 136.3, 133.0, 129.8, 128.0, 124.8, 117.2, 112.5, 71.3, 66.8, 56.2, 55.7, 53.7, 45.8, 45.4, 42.8, 40.3, 35.0, 28.9, 28.4, 27.3, 23.4, 22.2, 21.6, 18.5, 12.0; IR (thin film) 3400, 2926, 2872, 1597, 1449, 1313, 1302, 1286, 1142, 1087, 1053, 754, 668 cm$^{-1}$; HRMS [M+Na] calc'd 521.2696 for C$_{30}$H$_{42}$O$_4$SNa. found: 521.2707; UV (MeOH) λ$_{max}$ 264 nm (ε 8700).

I(i)

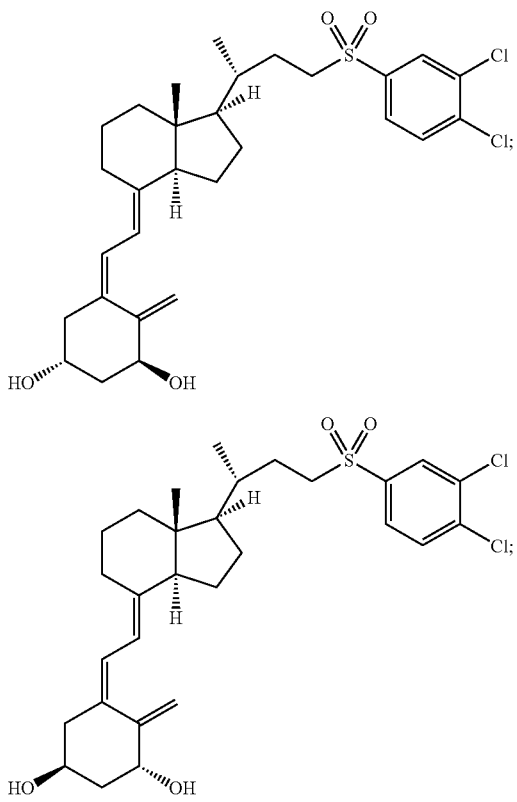

(e)

I(j)

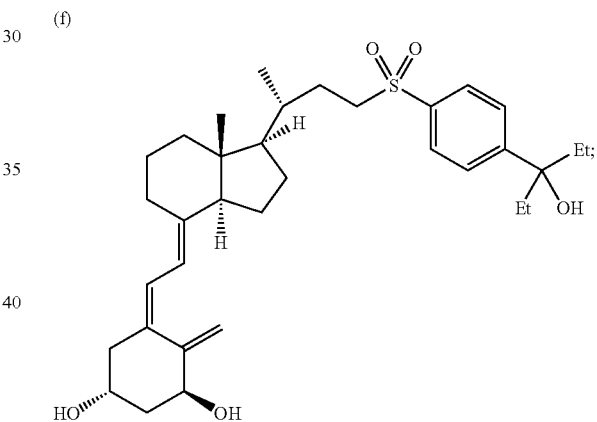

by replacing the compound of Example 4a with the compound of example 4e;

The diastereomers were purified by HPLC (Chiralcel OJ column, 22% EtOH in Hexanes, 2.5 mL/min, 254 nm) to afford 17.7 mg (52%) of (+)-I(i) (1α,3β, t$_R$ 36.4 min) as a viscous oil and 5.3 mg (16%) of (+)-I(j) (1β,3α, t$_R$ 29.0 min) as a viscous oil. (+)-I(i): R$_f$ 0.73 (EtOAc); [α]D$^{26}$+28.3 (c 2.10, CHCl$_3$); $^1$H NMR (400 MHz, CDCl$_3$) δ 8.00 (d, J=2.0 Hz, 1H), 7.73 (dd, J=2.4, 8.4 Hz, 2H), 7.66 (d, J=8.4 Hz, 1H), 6.36 (d, J=11.6 Hz, 1H), 6.01 (d, J=11.2 Hz, 1H), 5.33 (dd, J=1.2, 1.6 Hz, 1H), 4.99 (m, 1H), 4.43 (dd, J=4.4, 7.6 Hz, 1H), 4.23 (m, 1H), 3.14 (ddd, J=4.4, 12.0, 14.0 Hz, 1H), 3.00 (ddd, J=4.8, 11.2, 14.0 Hz, 1H), 2.82 (dd, J=4.4, 12.0 Hz, 1H), 2.59 (dd, J=3.6, 13.6 Hz, 1H), 2.31 (dd, J=6.4, 13.6 Hz, 1H), 1.92–2.04 (m, 4H), 1.76–1.90 (m, 2H), 1.64–1.71 (m, 4H), 1.45–1.58 (m, 5H), 1.20–1.31 (m, 3H), 0.90 (d, J=6.0 Hz, 3H), 0.52 (s, 3H); $^{13}$C NMR (100 MHz, CDCl$_3$) δ 147.6, 142.4, 139.0, 138.8, 134.1, 133.3, 131.4, 130.0, 127.1, 124.8, 117.3, 111.8, 70.8, 66.8, 56.1, 55.7, 53.7, 45.8, 45.2, 42.8, 40.3, 35.0, 28.9, 28.2, 27.4, 23.4, 22.1, 18.4, 12.0; IR (thin film) 3375, 2945, 1454, 1370, 1316, 1149, 1093, 1053, 1034, 824, 754, 676, 633 cm$^{-1}$; HRMS [M+Na] calc'd 575.1760 for C$_{29}$H$_{38}$Cl$_2$O$_4$SNa. found: 575.1764; UV (MeOH) λ$_{max}$ 262 nm (ε 12000). (+)-I(j): R$_f$ 0.73 (EtOAc); [α]D$^{26}$+22.6 (c 0.54, CHCl$_3$); $^1$H NMR (400 MHz, CDCl$_3$) δ 8.00 (d, J=2.0 Hz, 1H), 7.73 (dd, J=2.0, 8.4 Hz, 2H), 7.66 (d, J=8.4 Hz, 1H), 6.37 (d, J=11.2 Hz, 1H), 6.00 (d, J=11.2 Hz, 1H), 5.32 (m, 1H), 4.99 (m, 1H), 4.44 (m, 1H), 4.22 (m, 1H), 3.14 (ddd, J=4.4, 12.0, 14.0 Hz, 1H), 3.00 (ddd, J=4.4, 11.6, 14.0 Hz, 1H), 2.82 (dd, J=4.4, 12.4 Hz, 1H), 2.61 (dd, J=4.0, 13.2 Hz, 1H), 2.30 (dd, J=7.6, 13.2 Hz, 1H), 1.90–2.04 (m, 4H), 1.76–1.89 (m, 2H), 1.46–1.72 (m, 9H), 1.20–1.31 (m, 3H), 0.91 (d, J=6.0 Hz, 3H), 0.52 (s, 3H); $^{13}$C NMR (100 MHz, CDCl$_3$) δ 147.2, 142.4, 139.0, 138.8, 134.1, 133.1, 131.4, 130.1, 127.1, 124.8, 117.3, 112.6, 71.3, 66.8, 56.1, 55.7, 53.8, 45.8, 45.4, 42.8, 40.3, 35.0, 28.9, 28.2, 27.4, 23.4, 22.2, 18.5, 12.0; IR (thin film) 3371, 2945, 2872, 1454, 1370, 1316, 1149, 1093, 1053, 1034, 824, 754, 676 cm$^{-1}$; HRMS [M+Na] calc'd 575.1760 for C$_{29}$H$_{38}$Cl$_2$O$_4$SNa. found: 575.1764; UV (MeOH) λ$_{max}$ 264 nm (ε 11000).

I(k)

(f)

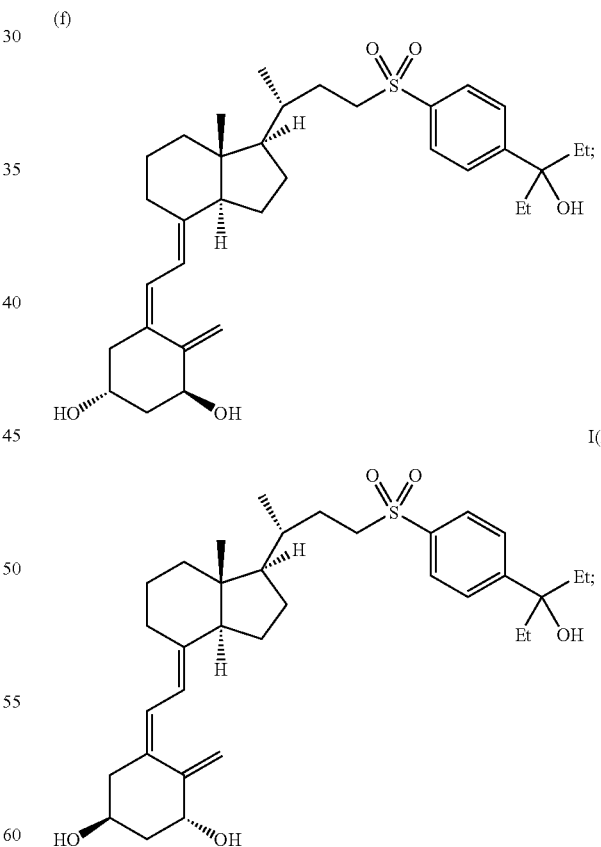

I(l)

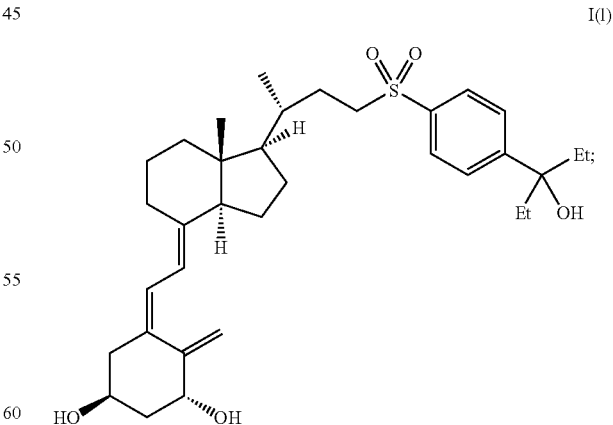

by replacing the compound of Example 4a with the compound of example 4f.

The diastereomers were then purified by HPLC (Chiralcel OJ column, 15% EtOH in Hexanes, 2.5 mL/min, 254 nm) to afford 8.2 mg (47%) of (+)-I(k) (1α,3β, t$_R$ 36.3 min) as a viscous oil and 5.1 mg (29%) of I(l)) (1β,3α, $t_R$ 30.5 min) as a viscous oil. (+)-I(k): $R_f$ 0.56 (EtOAc); $[\alpha]D^{26}$+25.1 (c 2.10, CHCl$_3$); $^1$H NMR (400 MHz, CDCl$_3$) δ 7.85–7.88 (m, 2H), 7.58–7.60 (m, 2H), 6.36 (d, J=10.8 Hz, 1H), 5.99 (d, J=11.2 Hz, 1H), 5.32 (dd, J=1.2, 2.0 Hz, 1H), 4.98 (m, 1H), 4.43 (dd, J=4.4, 7.6 Hz, 1H), 4.22 (tt, J=3.6, 6.4 Hz, 1H), 3.13 (ddd, J=4.4, 12.0, 14.0 Hz, 1H), 3.00 (ddd, J=4.8, 11.2, 13.6 Hz, 1H), 2.81 (dd, J=4.4, 12.4 Hz, 1H), 2.59 (dd, J=3.2, 13.6 Hz, 1H), 2.31 (dd, J=6.4, 13.6 Hz, 1H), 1.79–2.05 (m, 10H), 1.40–1.75 (m, 9H), 1.11–1.29 (m, 4H), 0.89 (d, J=6.4 Hz, 3H), 0.75 (t, J=7.2 Hz, 6H), 0.49 (s, 3H); $^{13}$C NMR (100 MHz, CDCl$_3$) δ 152.2, 147.6, 142.5, 137.0, 133.2, 127.8, 126.5, 124.8, 117.2, 111.8, 77.4, 70.8, 66.8, 56.2, 55.6, 53.6, 45.8, 45.2, 42.8, 40.3, 35.29, 35.26, 35.0, 29.0, 28.3, 27.2, 23.4, 22.1, 18.5, 12.0, 7.6; IR (thin film) 3456, 2937, 1458, 1311, 1144, 1086, 1054, 967, 755 cm$^{-1}$; HRMS [M+Na] calc'd 593.3271 for C$_{34}$H$_{50}$O$_5$SNa. found: 593.3237; UV (MeOH) $\lambda_{max}$ 261 nm (ε 8600). I(l): $R_f$ 0.73 (EtOAc); $^1$H NMR (400 MHz, CDCl$_3$) δ 7.86–7.88 (m, 2H), 7.58–7.61 (m, 2H), 6.37 (d, J=11.2 Hz, 1H), 5.98 (d, J=11.2 Hz, 1H), 5.31 (m, 1H), 4.98 (m, 1H), 4.43 (dd, J=4.4, 6.4 Hz, 1H), 4.21 (tt, J=3.6, 7.2 Hz, 1H), 3.13 (ddd, J=4.4, 12.0, 14.0 Hz, 1H), 3.00 (ddd, J=4.8, 11.2, 14.0 Hz, 1H), 2.81 (dd, J=4.4, 12.8 Hz, 1H), 2.61 (dd, J=4.0, 13.2 Hz, 1H), 2.29 (dd, J=7.2, 13.2 Hz, 1H), 1.80–2.03 (m, 1OH), 1.40–1.75 (m, 9H), 1.13–1.29 (m, 4H), 0.89 (d, J=6.4 Hz, 3H), 0.75 (t, J=7.2 Hz, 6H), 0.49 (s, 3H); The title compound I(l) was decomposed during overnight $^{13}$C NMR.

(g)

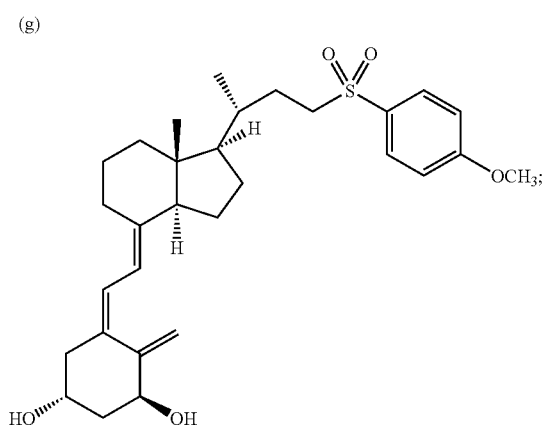

I(m)

(h)

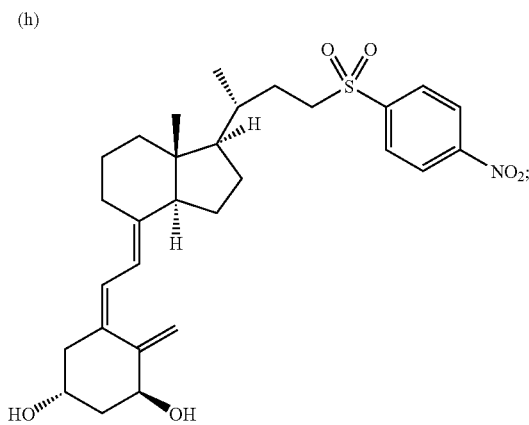

I(n)

by replacing the compound of Example 4a with the compound of example 4h;

I(o)

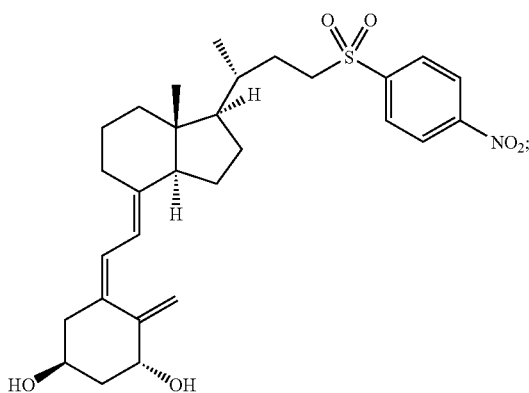

I(p)

by replacing the compound of Example 4a with the compound of example 4i; and (i)

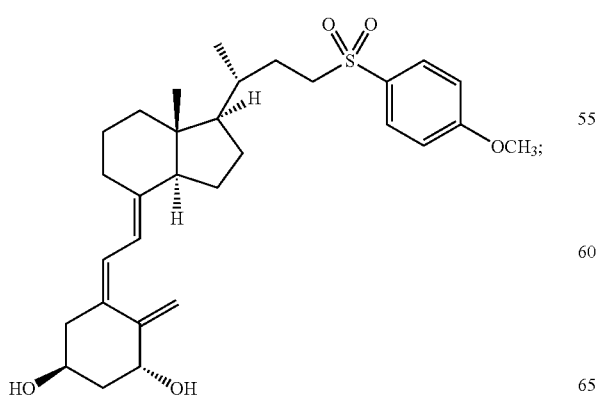

I(q)

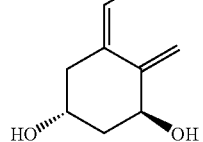

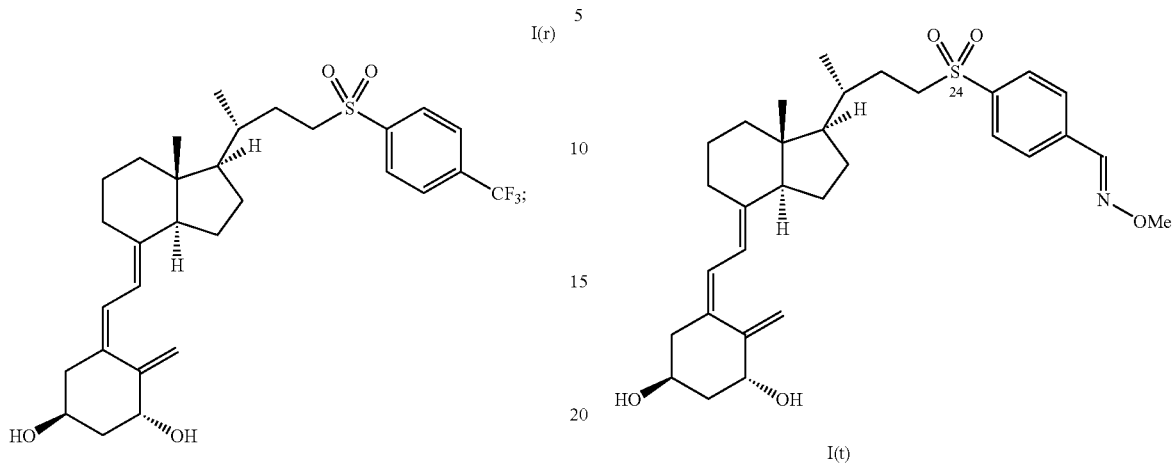

by replacing the compound of Example 3a with the compound of example 4j.

Example 6

Preparation of 24-SO2-PhCH(NOMe) I(s) and I(t)

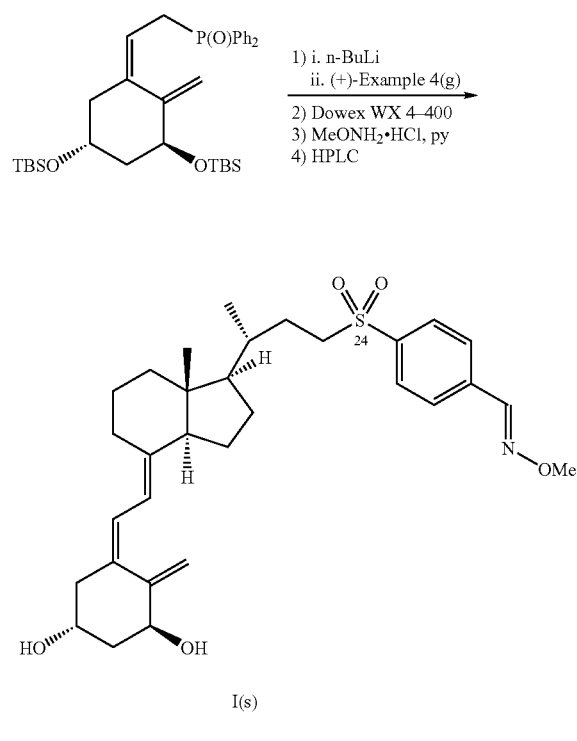

To a solution of (±)-A-ring phosphine oxide (Posner, G. H. et al. *J. Med. Chem.* 1992, 35, 3280–3287) (72.8 mg, 0.125 mmol) in THF (2 mL) was added 0.047 mL of n-BuLi (2.67 M in Hexane, 0.125 mmol) at −78 C., then the reddish solution was stirred for 10 min at the same temperature. A precooled (−78° C.) solution of C24-p-acetalphenyl sulfone C/D ring ketone from Example 4g (32.4 mg, 0.0770 mmol) in THF (2 mL) was added to the above solution at −78° C. via cannula. The resulting reddish orange solution was stirred for 6 hrs at −78° C. The reaction was quenched with 2 mL of pH 7 buffer, then warmed to room temperature, extracted with EtOAc, washed with brine, dried over $MgSO_4$, filtered, concentrated in vacuo, and purified by flash chromatography (EtOAc:Hex=1:4) to give 31.5 mg (52%) of a diastereomeric mixture of bis TBS protected p-acetalphenyl sulfone coupled products. A solution of this latter product (20 mg, 0.0255 mmol) and Dowex 50WX4-400 (794 mg) in $CH_2CL_2$-acetone (2 mL-2 mL) was stirred for 24 h. The reaction mixture was filtered and purified by flash chromatography (EtOAc:Hex=1:1 to 2:1) to afford 5.4 mg of a diastereomeric mixture of the corresponding bishydroxy benzaldehydes along with some unreacted starting material. The latter mixture was treated with $MeONH_2.HCl$ (8.9 mg, 0.104 mmol), several beads of molecular sieves 4A, and pyridine (1.2 mL). The reaction mixture was diluted with EtOAc, washed with 1N aq. HCl and brine, dried over $MgSO_4$, filtered, and concentrated in vacuo to give a crude mixture which was then purified by flash chromatography (EtOAc:Hex=3:1) to afford 3.7 mg (65%) of a diastereomeric mixture of I(s) and I(t). The diastereomers were then purified by HPLC (Chiralcel OJ column, 30% EtOH in Hexanes, 2.5 mL/min, 254 nm) to afford I(s) (1α,3β, $t_R$ 32.7 min) as a viscous oil and I(t) (1β,3α, $t_R$ 25.1 min) as a viscous oil.

Example 7

Preparation of Compound I(u)

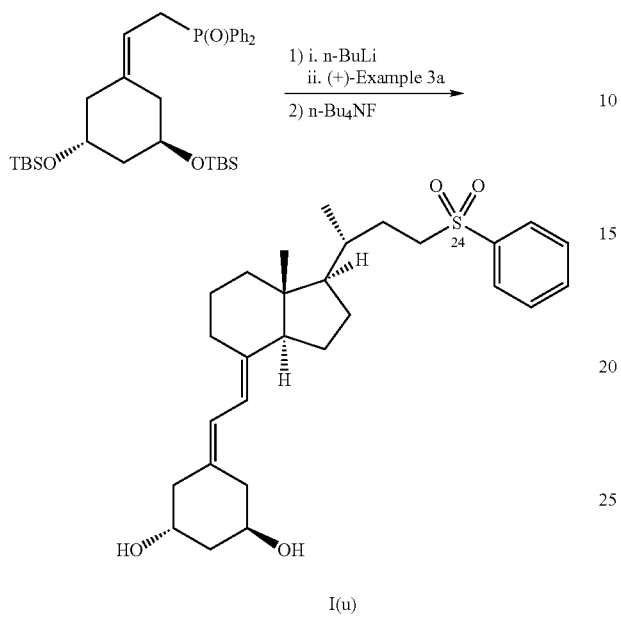

A solution of 58 mg (0.10 mmol) of 19-nor-phosphine oxide (Hilpert, H. and Wirz, B. *Tetrahedron* 2001, 57, 681–694) in 2.0 mL of anhydrous THF was cooled to −78 °C. and treated with 64 μL (0.10 mmol, 1.6 M in hexanes) of n-BuLi under argon atmosphere. The mixture turned deep reddish and was stirred for 15 min at −78° C. To the solution was added dropwise a precooled (−78° C.) solution of 12 mg (0.034 mmol) of the C,D-ring ketone from Example 3a in 1.5 mL of anhydrous THF via cannula. The reaction kept going until the reddish orange color faded to yellow (about 4 hr). The reaction was quenched by adding 1.0 mL of pH 7 buffer at −78° C., then warmed to room temperature, extracted with EtOAc (20 mL×2), washed with brine, dried over MgSO$_4$, concentrated. The residue was subjected to column chromatography with EtOAc/hexanes (1/3) as eluent to afford 19 mg (80%) of the coupled product as a colorless oil.

The coupled product (19 mg, 0.027 mmol) was dissolved in 3 mL of anhydrous THF, and to the solution was added 0.40 mL (0.40 mmol) of a 1.0 M solution of TBAF in THF. The resulting mixture was stirred overnight at room temperature, then quenched with 2 mL of water. The solution was extracted with EtOAc (20 mL×3), washed with brine, dried over MgSO$_4$, concentrated. The residue was subjected to column chromatography with EtOAc as eluent to give 12 mg (94%) of the crude product of (+)-I(u) as a colorless oil. The crude product was purified by HPLC (Chiralcel OJ column, 20% EtOH in Hexanes, 2.5 mL/min, 254 nm) to afford 10.5 mg of (+)-I(u) (1α,3β, $t_R$=29.1 min). $[α]^{24}_D$=+ 91.2 (c=0.19, MeOH). $^1$H NMR (400 MHz, CDCl$_3$) δ 7.90–7.93 (m, 2H), 7.67 (m, 1H), 7.56–7.60 (m, 2H), 6.29 (d, J=11.2 Hz, 1H), 5.83 (d, J=11.2 Hz, 1H), 4.11 (m, 1H), 4.05 (m, 1H), 3.14 (ddd, J=13.6, 12.0, 4.0 Hz, 1H), 3.00 (ddd, J=13.6, 11.2, 4.8 Hz, 1H), 2.78 (dd, J=12.4, 4.0 Hz, 1H), 2.72 (dd, J=13.2, 4.0 Hz, 1H), 2.47 (dd, J=13.2, 3.6 Hz, 1H), 2.17–2.43 (m, 2H), 1.74–1.99 (m, 6H), 1.44–1.68 (m, 9H), 1.17–1.30 (m, 3H), 0.89 (d, J=6.0 Hz, 3H), 0.50 (s, 3H). $^{13}$C NMR (100 MHz, CDCl$_3$) δ 142.4, 139.2, 133.6, 131.4, 129.2, 128.0, 123.7, 115.5, 67.4, 67.2, 56.1, 55.7, 53.6, 45.7, 44.6, 42.1, 40.3, 37.1, 35.0, 28.8, 28.3, 27.3, 23.3, 22.1, 18.5, 12.0. IR (neat, cm$^{-1}$) 3362, 2943, 1447, 1306, 1145, 1086, 1048, 753, 689, 537. HRMS ([M+Na]+) calcd. 495.2539, found 495.2526.

Example 8

Pretaration of Aldehyde (+)-XI

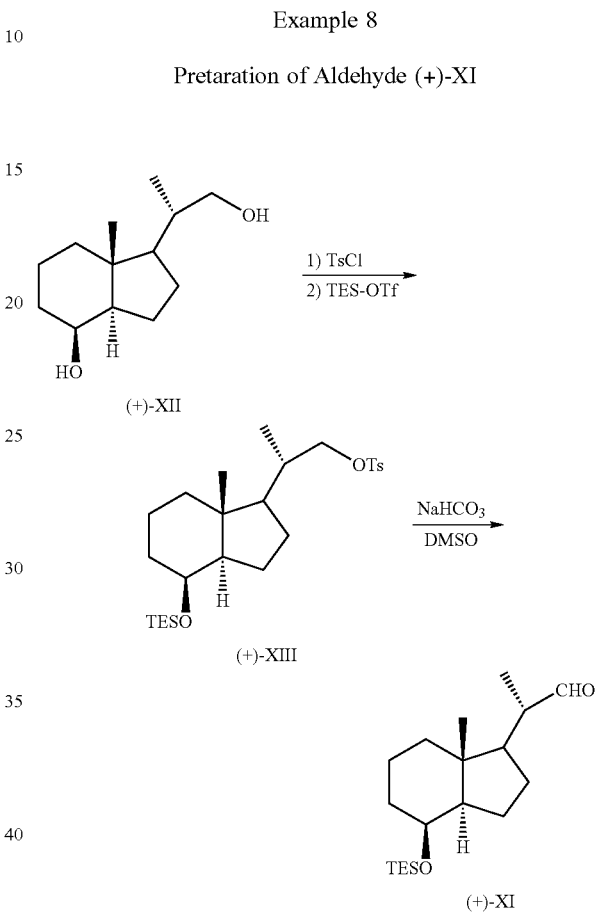

(a) Preparation of Lythgoe diol (+)-XII: As described in Posner G. H. et al. *J. Org. Chem.* 1997,62,3299–3314.

(b) Preparation of TES Tosylate (+)-XIII: To a solution of the diol (+)-XII (364 mg, 1.64 mmol eq) and DMAP (341 mg, 1.7 eq) in 15 mL of CH$_2$Cl$_2$ was slowly added the soluion of p-toluenesulfonyl chloride (360 mg, 1.2 eq) in 5 mL of CH$_2$Cl$_2$ at 0° C. After being stirred for 16 h at 0° C., the reaction mixture was cooled to −78° C. To this was added 2,6-lutidine (0.95 mL) and TESOTf (1.1 mL) successively with monitoring by TLC. Upon the completion of reaction, the mixture was diluted with ether, successively washed with diluted HCl to remove 2,6-lutidine followed by brine. The organic extract was dried over MgSO$_4$, concentrated in vacuo, and then purified by chromatography (25% EtOAc/hexanes) to give 708 mg (90%) of the desired TES tosylate (+)-XIII as a colorless oil. $[α]^{25}_D$ −12° (c 2.3, EtOAc); $^1$H NMR (CDCl$_3$) δ 7.79 (d, J=8.0 Hz, 2H), 7.33 (d, J=8.0 Hz, 2H), 4.17 (m, 2H), 3.84 (dd, J=8.0, 4.8 Hz, 1H), 2.43 (s, 3H), 1.80 (m, 2H), 1.52 (m, 4H), 1.33 (s, 3H), 1.22 (s, 3H), 0.87 (t, J=7.6 Hz, 3H), 0.83 (t, J=7.6 Hz, 3H); $^{13}$C NMR (CDCl$_3$) δ 144.69, 132.94, 129.78, 127.82, 106.81, 83.80, 76.72, 68.33, 29.39, 28.36, 27.15, 26.82, 25.36, 21.6, 8.19, 7.23; IR (CDCl$_3$, cm$^{-1}$) 2941, 2860, 1732, 1592, 1458, 1354; HRMS (CI) m/z (M+H$^+$) calcd. 357.1736 for C$_{18}$H$_{28}$O$_5$S, found 357.1741.

(c) Preparation of Aldehyde (+)-XI: According to the method of Kornblum, et al. *J. Am. Chem. Soc.* 1959, 81, 4113–3116, to a solution of primary tosylate (+)-XIII (708 mg, 0.147 mmol) in DMSO (10 mL) was added NaHCO$_3$ (495 mg, 5.9 mmol) and heated to 150° C. When the evolution of gas had ceased (10–15 min) the reaction mixture was cooled rapidly to rt (water bath), diluted with water (50 mL), and extracted (×2) with ether. The organic fractions were combined, washed repeatedly with brine, dried with Na$_2$SO$_4$, and concentrated to a light oil. Purification by flash silica gel chromatography (2% EtOAc/hexanes) provided 120 mg (80%) of aldehyde (+)-XI as a colorless oil: [α]$^{25}_D$ +40.7° (c 2.3, CHCl$_3$); $^1$H NMR (400 MHz, CDCl$_3$) δ 9.54 (d, J=3.2 Hz, 1H), 4.03 (m, 1H), 2.32 (ddq, J=10.0, 6.8, 3.2 Hz, 1H), 1.73–1.92 (m, 3H), 1.58–1.71 (m, 2H), 1.28–1.44 (m, 5H), 1.10–1.26 (m, 2H), 1.06 (d, J=6.8 Hz, 3H) 0.93 (s, 3H), 0.91 (t, J=8.0 Hz, 9H) 0.52 (q, J=8.0 Hz, 6H); $^{13}$C NMR (100 MHz, CDCl$_3$) δ 205.2, 69.0, 52.3, 51.6, 49.1, 42.6, 40.4, 34.5, 26.2, 23.3, 17.6, 13.9, 13.3, 6.9, 4.9; IR (thin film cm$^{-1}$) 2948, 2872, 1724, 1456, 1164.

Example 9

Preparation of Ketones (+)-III (R$^4$=t-butyl) and (+)-III (R$^4$=isopropyl)

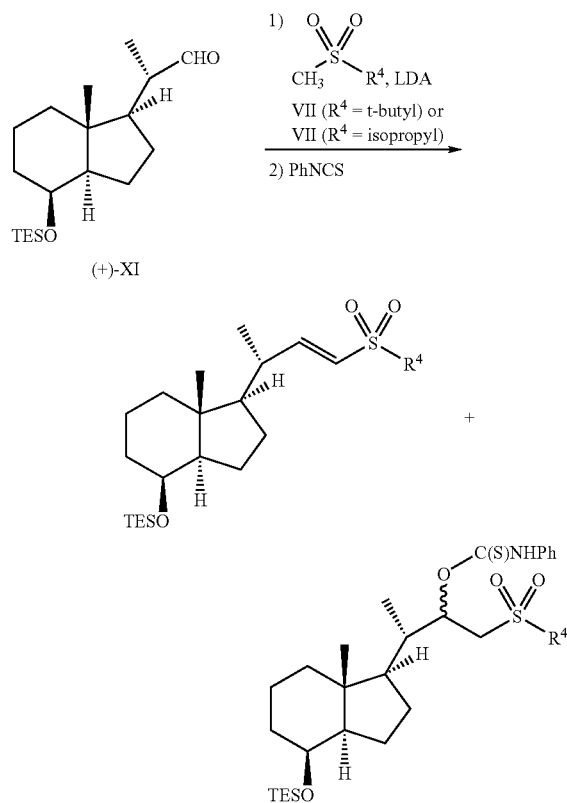

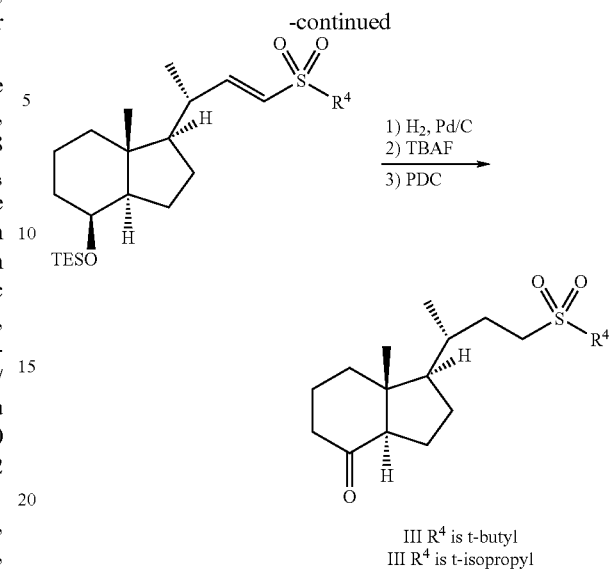

III R$^4$ is t-butyl
III R$^4$ is t-isopropyl (a) Preparation of tert-Butyl methyl sulfone VII (R$^4$=t-butyl) and isopropyl methyl sulfone VII (R$^4$=isopropyl): To a solution of tert-butyl methyl sulfide (5.0 g, 0.048 mol) in methanol (125 ml) was added oxone (21.9 g, 0.144 mol) in H$_2$O (125 ml) at 0 C. The mixture was warmed to ambient temperature and allowed to stir overnight. The mixture was concentrated to constant volume, diluted with water (150 mL), extracted with CH$_2$Cl$_2$ (6×50 mL), dried over MgSO$_4$ and concentrated in vacuo to provide sulfone VII, where R$^4$ is t-butyl (6.20 g, 95%) as a white solid. $^1$H NMR (400 MHz, CDCl3) δ 2.82 (s, 3H), 1.44 (s, 9H); $^{13}$C NMR (100 MHz, CDCl$_3$) δ 59.62, 35.10, 24.37. Isopropyl methyl sulfone VII, where R$^4$ is isopropyl, can be prepared in the same manner by oxidizing isopropyl methyl sulfide, instead of tert-butyl methyl sulfide.

(b) Preparation of α,β-unsaturated sulfone wherein R$^4$ is t-butyl: To a solution of diisopropylamine (91 μL, 1.5 eq) in THF (3 mL) was added 1.6 M solution of n-BuLi hexanes (0.4 mL, 1.5 eq) at −78° C., and then it was stirred for an additional 30 min at −78° C. and another 30 min at −35° C. A solution of t-butylmethyl sulfone VII (R$^4$=t-butyl) (143 mg, 1.5 eq) in THF (1 mL) was added to the LDA solution at −78° C. After being stirred for 1 h, the solution was treated with a solution of the aldehyde (+)-XI (130 mg, 0.44 mmol) in THF (0.5 mL) by dropwise addition. The reaction mixture was stirred for 15 min at the same temperature, quenched with a solution of phenylisothiocyanate (PhNCS) (0.15 mL, 1.6 eq) in THF (1 mL), and then warmed to rt. After being stirred for 30 min at rt, the reaction mixture was extracted with ether (50 mL×2), washed with saturated NaHCO$_3$ solution, brine, dried over MgSO$_4$, concentrated in vacuo, and then purified by chromatography (10% EtOAc/hexanes) to give 95 mg (49%) of the α,β-unsaturated sulfone and 73 mg (31%) of corresponding phenylthianocarbamate as diasteromeric mixtures. [α]$^{25}_D$ +56° (c 9.4, CHCl$_3$); $^1$H NMR (400 MHz, CDCl$_3$) δ 6.73 (dd, J=15.2 Hz, 9.2, 1H), 6.14 (d, J=15.2, 1H), 4.03 (br d, J=2.4, 1H), 1.90–1.94 (dm, J=12.4 Hz, 1H), 1.54–1.84 (m, 4H), 1.34 (s, 9H), 1.12–1.27 (m, 5H), 1.09 (d, J=6.4 Hz, 3H), 0.94 (s, 3H), 0.93 (t, J=8.0 Hz, 9H), 0.54 (q, J=8.0 Hz, 6H); $^{13}$C NMR (100 MHz, CDCl$_3$) δ 156.55, 121.30, 69.09, 58.29, 55.24, 52.78, 42.53, 41.90, 40.57, 39.57, 34.45, 27.66, 23.35, 23.03, 18.96, 17, 13.79, 6.91, 4.90; MS m/z (70 e V, CI) 460 (M+NH$_4^+$); HRMS m/z (M$^+$) Calcd. 460.3281 for C$_{24}$H$_{46}$O$_3$SSi found 460.3292; IR (neat, cm$^{-1}$) 2951, 2875, 1631, 1457, 1304.

(c) Preparation of α,β-unsaturated sulfone wherein R$^4$ is isopropyl: A solution of aldehyde (+)XI (232 mg, 0.78 mmol) in THF (2 mL) was reacted with the anion of isopropyl methyl sulfone VII (R$^4$=isopropyl) (143 mg, 1.5 eq) in THF (3.0 mL) as described in part (b) to give 54 mg (18%) of the α,β-unsaturated isopropyl sulfone and 351 mg (81%) of the corresponding phenylthianocarbamate as diasteromeric mixtures. $^1$H NMR (400 MHz, CDCl$_3$) δ 6.75 (dd, J=9.2, 15.2 Hz, 1H), 6.11 (d, J=15.2, 1H), 4.03 (d, J=2.4, 1H), 3.17 (septet, J=6.8 Hz, 1H), 2.33–2.39 (m, 1H), 2.06–2.17 (m, 2H), 1.76–1.81 (m, 1H), 1.53–1.71 (m, 3H), 1.32–1.39 (m, 4H), 1.16–1.27 (m, 3H), 1.33 (d, J=7.2 Hz, 6H), 1.10 (d, J=6.8 Hz, 3H), 0.95 (s, 3H), 0.94 (t, J=8.0 Hz, 9H), 0.55 (q, J=8.0 Hz, 6H).

(d) Preparation of C/D ring ketone (+)-III, wherein R$^4$ is t-butyl: A solution of α,β unsaturated sulfone from part (b) (94 mg, 0.21 mmol) in benzene (10 mL) was hydrogenated (50 psi) for 2 days in the presence of 10 mg of 10% Pd/C until the absence of starting material was indicated by TLC. The reaction mixture was filtered through a bed of Celite™ with several benzene washes and the filtrate was concentrated to a light oil. The resulting mixture was treated with TBAF in THF followed by normal aqueous work-up, then purified by chromatography (40% EtOAc/hexanes) to give 70 mg (98%) of alcohol as a white solid: mp. 129–131° C.; [α]$^{25}_D$ +37° (c 4.3, CHCl$_3$); $^1$H NMR (400 MHz, CDCl$_3$) δ $^1$H NMR (400 MHz, CDCl$_3$) δ 4.05 (br d, J=2.4, 1H), 2.92 (td, J=12.8, 4.4 Hz, 1H), 2.72–2.79 (m, 1H), 1.73–2.02 (m, 5H), 1.26–1.61 (m, 8H), 1.7 (d, J=7.2 Hz, 6H), 1.27–1.60 (m, 3H), 1.37 (s, 9H), 1.02–1.18 (m, 2H), 0.91 (d, J=6.8 Hz, 3H), 0.90 (s, 3H); $^{13}$C NMR (100 MHz, CDCl$_3$) δ 69.07, 58.89, 56.17, 52.45, 42.96, 41.90, 40.28, 34.72, 33.46, 27.02, 26.00, 23.48, 22.39, 18.23, 17.36, 13.50; MS m/z (70 eV, CI) 348 (M+NH$_4^+$); HRMS m/z (M$^+$) Cald. 330.2229 for C$_{18}$H$_{34}$O$_3$S, found 330.2236; IR (CHCl$_3$, cm$^{-1}$) 3519, 2942, 2872, 1464, 1299, 1281, 1116. To a solution of the alcohol (71 mg, 0.21 mmol) in CH$_2$Cl$_2$ (5 mL), were added 0.24 g of oven dried Celite™ and PDC (0.24 g, 3.0 eq) at rt. After stirring at rt for 16 h, the mixture was passed through 2 cm of flash silica gel pad, washed with EtOAc. The filtrate was concentrated in vacuo, and then chromatographed with 30% EtOAc in hexanes to give 61 mg (86%) of the ketone (+)-III, where R$^4$ is t-butyl, as a white solid: mp. 123–125° C.; [α]$^{25}_D$ +14° (c 4.9, CHCl$_3$); $^1$H NMR (400 MHz, CDCl$_3$) δ 2.90–2.98 (m, 1H), 2.74–2.82 (m, 1H), 2.44 (dd, J=11.6, 7.2 Hz, 1H), 2.15–2.28 (m, 2H), 1.80–2.10 (m, 4H), 1.66–1.77 (m, 1H), 1.35–1.64 (m, 7H), 1.39 (s, 9H), 0.97 (d, J=6.4 Hz, 3H), 0.62 (s, 3H); $^{13}$C NMR (100 MHz, CDCl$_3$) δ 211.47, 61.67, 58.91, 49.75, 42.83, 40.78, 38.78, 34.91, 27.33, 26.09, 23.88, 23.42, 18.96, 18.37, 12.45; MS m/z (70 eV, CI) 346 (M+NH$_4$); HRMS m/z (M$^+$) Calcd. 328.2072 for C$_{18}$H$_{32}$O$_3$S, found 328.2076; IR (CHCl$_3$, cm$^{-1}$) 3020, 2964, 2877, 1707, 1464,1298, 1280,1116.

(e) Preparation of C/D ring ketone (+)-III, wherein R$^4$ is isopropyl: A solution of α,β unsaturated sulfone from part (c) (54 mg, 0.13 mmol) in benzene (5 mL) was hydrogenated (50 psi) for 2 days in the presence of 10 mg of 10% Pd/C until the absence of starting material was indicated by TLC. The reaction mixture was filtered through a bed of Celite™ with several benzene washes and the filtrate was concentrated to a light oil. The resulting mixture was treated with TBAF in THF followed by normal aqueous work-up, then purified by chromatography (40% EtOAc/hexanes) to give 33 mg (78%) of alcohol as a colorless oil. [α]$^{25}_D$ +37° (c 3.3, CHCl$_3$); $^1$H NMR (400 MHz, CDCl$_3$) δ 4.05 (br, dJ=2.4, 1H), 3.17 (septet, J=6.8 Hz, 1H) 2.92–3.00 (m, 1H), 2.76–2.83 (m, 1H), 1.73–1.97 (m, 5H), 1.26–1.61 (m, 8H), 1.37 (d, J=6.8 Hz, 6H), 1.03–1.17 (m, 2H), 0.93 (d, J=6.0 Hz, 3H) 0.92 (s, 3H); $^{13}$C NMR (100 MHz, CDCl$_3$) δ 69.04, 55.93, 52.49, 52.46, 46.56, 41.90, 40.28, 34.56, 33.47, 27.06, 26.93, 22.40, 18.24, 17.36, 15.36, 15.20, 13.51; MS m/z (70 eV, CI) 348 (M+NH$_4^+$); HRMS m/z (M$^+$) Calcd. 330.2229 for C$_{18}$H$_{34}$O$_3$S, found 330.2236; IR (neat cm$^{-1}$) 3519, 2942, 2872, 1464, 1299, 1281, 1116. The alcohol was oxidized with PDC in the same manner as described in part (d) to give 28 mg (86%)of the desired ketone III, where R$^4$ is isopropyl, as a colorless oil. [α]$^{25}_D$ +17° (c 2.8, CHCl$_3$); $^1$H NMR (400 MHz, CDCl$_3$) δ; 3.08 (septet, J=6.8 Hz, 1H), 2.93–3.00 (m, 1H), 2.78–2.85 (m, 1H), 2.45 (dd, J=11.6, 7.6 Hz, 1H), 2.16–2.30 (m, 2H), 1.68–2.10 (m, 6H), 1.52–1.63 (m, 5H), 1.37 (d, J=6.8 Hz, 6H), 1.32–1.45 (m, 2H), 0.99 (d, J=6.0 Hz, 3H), 0.63 (s, 3H); $^{13}$C NMR (100 MHz, CDCl$_3$) δ 210.40, 61.70, 56.00, 52.66, 49.75, 46.44, 40.81, 38.81, 34.79, 27.39, 26.94, 28.90, 18.99, 18.40, 15.34, 15.21, 12.48; MS m/z (70 eV, CI) 348 (M+NH$_4^+$); HRMS m/z (M$^+$) Calcd. 330.2229 for C$_{18}$H$_{34}$O$_3$S, found 330.2236; IR (neat, cm$^{-1}$) 2957, 2877, 1710, 1467, 1306, 1262, 1130.

Example 10

Preparation of Compounds of Formula I(v) and I(w)

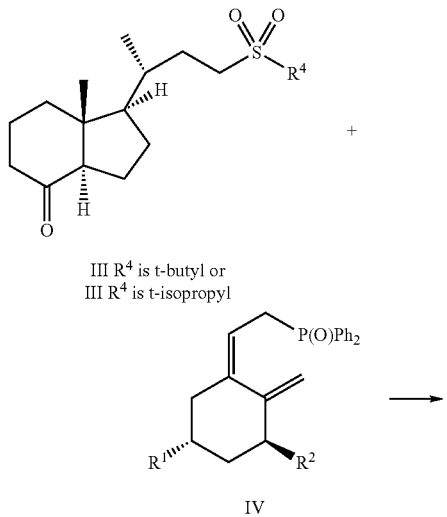

III R$^4$ is t-butyl or
III R$^4$ is t-isopropyl

IV

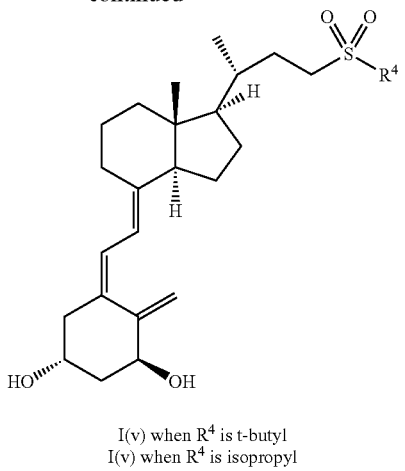

I(v) when R⁴ is t-butyl
I(v) when R⁴ is isopropyl (a) Preparation of a Compound of Formula I(v): A solution of 79 mg (0.13 mmol, 1.0 eq) of phosphine oxide (−)-IV in 1.5 mL of anhydrous THF was cooled to −78° C. and treated with 85 μL (0.15 mmol, 1.0 eq) of 1.7 M solution of phenyllithium in THF. The solution was stirred for 30 min at −78° C. To the solution, was added dropwise a solution of 45 mg (0.13 mmol, 1 eq) of the C,D-ring ketone (+) III (R⁴=t-butyl) in 1 mL of anhydrous THF. After being stirred for 2 hr at the same temperature, the reaction was quenched with 2 mL of a 1:1 mixture of 2N sodium potassium tartrate and 2 NK$_2$CO$_3$, extracted with EtOAc (50 mL×2) and washed with brine. The combined organic portions were dried with anhydrous MgSO$_4$, concentrated in vacuo, and then purified by chromatography (20% Et$_2$O/hexanes) to afford 30 mg of the coupled product as a colorless oil. The silyl ether was dissolved in 3 mL of anhydrous THF. To the solution, were added 0.17 mL (0.17 mmol, 4 eq) 1 M solution of TBAF in THF, and 23 μL (4 eq of triethylamine). After being stirred for 16 h at rt, the mixture was extracted with EtOAc (50 mL×2) and washed with brine. The combined organic proportions were dried with anhydrous MgSO$_4$, concentrated in vacuo, and then purified by chromatography (90% EtOAc/hexanes) to afford 20 mg (32%) of enantiomerically rich I(v) as a white solid. The solid was purified by the reverse phase HPLC (C-18 semipreparative column, 50% MeCN/H$_2$O), 3 ml/min, 262 nm) to afford 11.2 mg of (+)-IIa (1α,3β, ret. time 36 min): (+)-I(v) (1α,3β): mp. 89–93° C.; [α]$^{25}_D$ +63° (c 1.2, EtOH); $^1$H NMR (400 Mhz, CDCl$_3$) δ 6.36 (d, J=11.2 Hz, 1H), 6.01 (d, J=11.2 Hz, 1H), 5.32 (br s, 1H), 4.99 (br s, 1H), 4.41–4.44–4.05 (m, 1H), 4.22 (septet, J=3.2 Hz, 1H), 2.97 (tb, J=12.0, 4.4 Hz, 1H), 2.76–2.85 (m, 2H), 2.56–2.61 (m, 1H), 2.31 (dd, J=13.6, 6.8 Hz, 1H), 1.90–2.06 (m, 7H), 1.47–1.71 (m, 5H), 1.42 (s, 9H), 1.25–1.36 (m, 4H), 0.97 (d, J=6.0, 3H), 0.55 (s, 3H); $^{13}$C NMR (100 MHz, CDCl$_3$ δ 147.49, 142.54, 133.12, 124.76, 117.21, 111.86, 70.79, 66.79, 58.98, 56.18, 56.07, 45.91, 45.23, 42.96, 42.78, 40.38, 35.52, 28.98, 27.49, 26.18, 23.55, 23.48, 22.20, 18.54, 12.04; UV (MeOH) λ$_{max}$ 264 nm (ε 17,000); MS m/z (70 eV, Cl) 482 (M+NH$_4^+$); HRMS m/z (M$^+$) Calcd. 464.2960 for C$_{27}$H$_{44}$O$_4$S, found 464.2971; IR (neat, cm$^{-1}$) 3391, 2944, 2874, 1275, 1113.

(b) Preparation of a Compound of Formula I(w): The C/D-ring ketone (+)-III (R⁴=isopropyl) in 1 mL of anhydrous THF was reacted with a solution of 56 mg (0.10 mmol, 1.1 eq) of phosphine oxide (−)-IV in 1.0 mL of anhydrous THF followed by desilylation as described for I(v) above to afford 7.4 mg (19%) of enantiomerically rich (+)-I(w) as a white solid. The solid was purified by reverse phase HPLC (C-18 semipreparative column, 45% MeCN/H$_2$O, 3 ml/min, 262 nm) to afford 11.2 mg of (+)-I(w) (1α,3β, ret. time 28 min): (+)-I(w) (1α,3β): mp.54–56° C.; [α]$^{25}_D$ +59°) (c 0.5, EtOH); $^1$H NMR (400 MHz, CDCl$_3$) δ 6.37 (d, J=11.2 Hz, 1H), 6.01 (d, J=11.2 Hz, 1H), 5.33 (ts, J=1.6 Hz, 1H), 4.99 (br s, 1H), 4.41–4.44 (m, 1H), 4.23 (septet, J=3.2 Hz, 1H), 3.11 (septet, J=6.6 Hz, 1H), 2.97 (tb, J=12.0, 4.4 Hz, 1H), 2.79–2.86 (m, 2H), 2.60 (dd, J=13.6, 3.2 Hz, 1H), 2.31 (dd, J=13.6, 6.8 Hz, 1H), 1.90–2.05 (m, 6H), 1.48–1.72 (m, 6H), 1.39 (d, J=6.8, 3H), 1.24–1.36 (m, 4H), 0.97 (d, J=6.4, 3H), 0.56 (s, 3H); $^{13}$C NMR (100 MHz, CDCl$_3$) δ 147.53, 142.52, 133.15, 124.80, 117.25, 111.86, 70.83, 66.84, 56.20, 55.88, 52.60, 46.60, 45.91, 45.26, 42.83, 40.39, 35.39, 28.99, 27.53, 27.12, 23.49, 22.22, 18.57, 15.46, 15.26, 12.05; UV (MeOH) λ$_{max}$ 263 nm (ε 16,700); MS m/z (70 eV, Cl) 470 (M+NH$_4^+$); HRMS m/z (M$^+$) Calcd. 450 for C$_{26}$H$_{42}$O$_4$S, found 450.; IR (neat, cm$^{-1}$) 3432, 2943, 2862, 1467, 1304, 1121.

Example 11

Preparation of Compounds I(x), I(v) ad I(z)

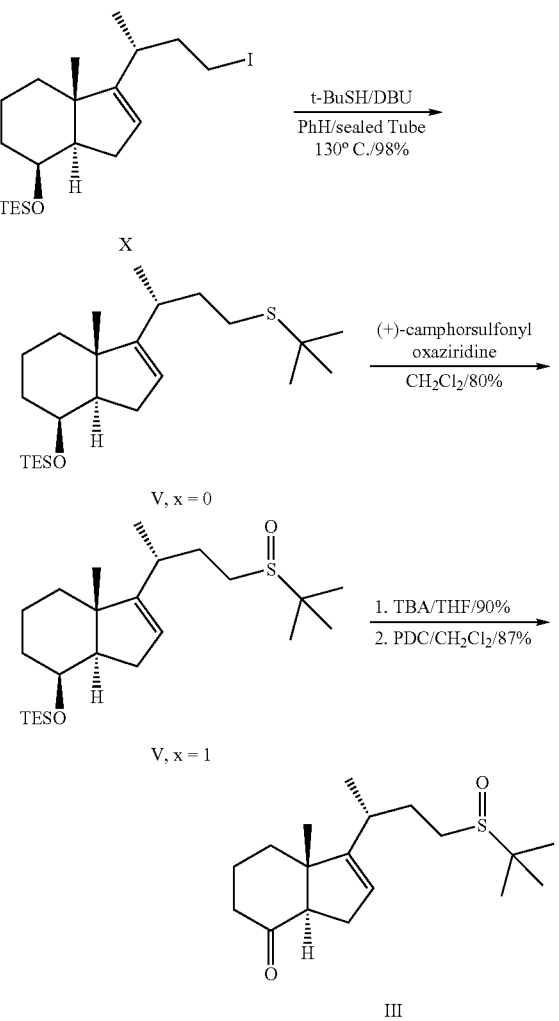

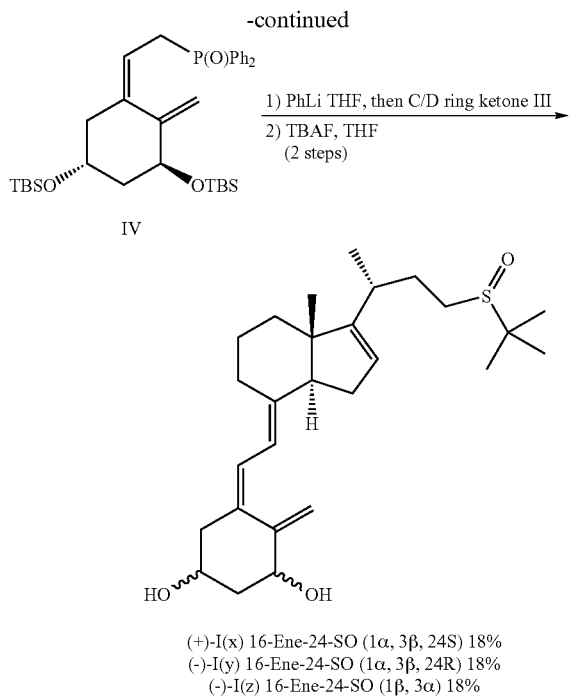

1) PhLi THF, then C/D ring ketone III
2) TBAF, THF
(2 steps)

(+)-I(x) 16-Ene-24-SO (1α, 3β, 24S) 18%
(−)-I(y) 16-Ene-24-SO (1α, 3β, 24R) 18%
(−)-I(z) 16-Ene-24-SO (1β, 3α) 18%

(a) 16-Ene-24-Sulfide (+)-V, x=0. To a solution of the known iodide (Jaekyoo, PhD Thesis, 1997, Johns Hopkins University) X (50 mg, 0.11 mmol) in 1.5 mL of benzene were added 0.025 mL of t-butanethiol (0.19 mmol) and 1,8-diazabicyclo[5.4.0]undec-7-ene (0.025 mL, 0.17 mmol) in hydrolysis tube. The reaction mixture was degased by freeze/thaw cycles (3 times). After 20 h at 130° C., the reaction mixture was cooled to rt, quenched with 3% HCl solution (10 mL) and extracted with ethyl acetate (50 mL×3). The combined organic extract was washed with brine (30 mL), dried over $MgSO_4$ and concentrated. The crude product was purified by flash column chromatography (6% ethyl acetate/hexanes) to give sulfide (+)-V (x=0) as a colorless oil (44 mg, 98%): $[\alpha]^{25}_D$ +18.0 (c 2.0, $CHCl_3$); $^1H$ NMR (400 MHz, $CDCl_3$) δ 5.29 (t, J=1.6 Hz, 1H), 4.12 (d, J=2.4 Hz, 1H), 2.41–2.54 (m, 2H), 2.26 (ddt, J=14.4, 12.0, 1.2 Hz, 1 H), 2.13–2.20 (m, 1H), 1.85–1.93 (m, 2H), 1.57–1.81 (m, 5H), 1.26–1.51 (m, 3H), 1.31 (s, 9H), 1.02 (s, 3H), 1.00 (d, J=6.8 Hz, 3H), 0.96 (t, J=8.0 Hz, 9H), 0.57 (q, J=8.0 Hz, 6H); $^{13}C$ NMR (100 MHz, $CDCl_3$) δ 159.66, 120.00, 68.96, 55.11, 46.70, 41.86, 36.58, 35.75, 34.96, 31.06, 30.78, 26.50, 22.28, 18.76, 18.09, 6.98, 4.65; IR (neat, $cm^{-1}$) 2956, 2928, 2875, 1457, 1029; HRMS m/z (M+H$^+$) calcd 411.3117 for $C_{24}H_{46}OSSi$, found 411.3109.

(b) 16-Ene-24-Sulfoxdes V (x=1). To a solution of sulfide (+)-V (x=0) (15 mg, 0.036 mmol) in 5.0 mL of $CH_2Cl_2$ was added (1S)-(+)-camphorsulfonyl oxaziridine (12 mg, 0.052 mmol) at room temperature. The reaction mixture was stirred for 6 h and concentrated. The crude product was purified by flash column chromatography (50% ethyl acetate/hexanes) to give diastereomeric sulfoxides V (x=1) as colorless oil (12 mg, 80%): $^1H$ NMR (400 MHz, $CDCl_3$) δ 5.30 (s, 1H), 4.10 (s, 1H), 2.45–1.60 (m, 13H), 1.48–1.33 (m, 3H), 1.21 and 1.20 (two s, 9H), 1.03 and 1.02 (two d, J=6.8 Hz, 3H), 0.97 and 0.96 (two s, 3H), 0.93 and 0.92 (two t, J=8.0 Hz, 9H), 0.54 (q, J=8.0 Hz, 6H); IR (neat, $cm^{-1}$) 2930, 2875, 1459, 1030.

(c) 16-Ene-8-Keto-24-Sulfoxides III (x=1). To a solution of triethylsilyl-ethers V (x=1) (45 mg, 0.11 mmol) in 5 mL of THF was added tetrabutylammonium fluoride (1 M in THF, 0.13 mL, 0.13 mmol). After 6 h at rt, the reaction mixture was concentrated in reduced pressure. The residue was purified by flashy chromatography (ethyl acetate) to give the corresponding alcohols as coloress oil (31 mg, 90%): $^1H$ NMR (400 MHz/$CDCl_3$) δ 5.36 (s, 1H), 4.17 (s, 1H), 2.49–2.16 (m, 4H), 2.04–1.72 (m, 6H), 1.56–1.37 (m, 4H), 1.203 and 1.196 (two s, 9H), 1.05 and 1.04 (two d, J=7.0 Hz, 3H), 1.02 and 1.01 (s, 3H); IR (neat, $cm^{-1}$) 3404, 2927, 2867, 1455, 1126; HRMS m/z (M$^+$) Calcd for $C_{18}H_{32}O_2S$ 313.2201, found 313.2209. To a solution of these alcohols (32 mg, 0.10 mmol) in 7 mL of dry $CH_2Cl_2$ was added 60 mg of oven dried celite and pyridinium dichlomate (65 mg, 0.17 mmol) at rt. After 4 h, the reaction mixture filtered through flashy silica pad, and then eluted with ethyl acetate. The filtrate was concentrated and purified by flash chromatography (ethyl acetate) to give ketones III as colorless oil (27 mg, 87%): $^1H$ NMR (400 MHz/$CDCl_3$) δ 5.33 (s, 1H), 2.85 (m, 1H), 2.47–2.25 (m, 7H), 2.11–1.75 (m, 8H), 1.20 and 1.19 (two s, 9H), 1.11 and 1.10 (two d, J=6.8 Hz, 3H), 0.80 and 0.77 (two s, 3H); IR (neat, $cm^{-1}$) 2959, 1720, 1458, 1363; HRMS m/z (M$^+$) Calcd for $C_{18}H_{30}O_2S$ 311.2045, found 311.2050.

(d) 16-Ene-24-Sulfoxides I(x), I(y) and I(z). To a solution of phosphine oxide (±:)-IV (105 mg, 0.18 mmol) in 1 mL of anhydrous THF was treated dropwise with phenyl lithium (1.46 M in cyclohexane-ether, 0.12 mL, 0.18 mmol) at −78° C. The resulting reddish orange solution was stirred at −78° C. for 30 min and then a solution of ketones (+)-IV (x=1) (27 mg, 0.087 mmol) in 1 mL of anhydrous THF was added dropwise. The reaction mixture was stirred until reddish color turned to pale yellow, and then quenched with 3 mL of a 1/1 mixture of 2 N sodium potassium tartrate solution and 2 N $K_2CO_3$ solution. The aqueous layer was extracted with ethyl acetate (50 mL×3). The combined organic extract was with brine (50 mL), dried over $MgSO_4$, and concentrated. The residue was purified by preparative TLC (ethyl acetate) to give coupled protected products (38 mg, 64%) and unreacted CD-ring ketones IV (9 mg, 33%). To a solution of the above silyl ethers in 10 mL of THF was tetrabutylammonium floride (1 M in THF, 0.16 mL, 0.16 mmol) and 25 L of TEA. The solution was stirred at rt for 16 h in dark. The reaction mixture was concentrated in reduced pressure. The residue was purified by preparative TLC (ethyl acetate) to give a mixture of diastereomeric diols I(x), I(y) and I(z) as colorless oil (21 mg, $^{76}$%). The diastereomers were separated by reverse phase HPLC (C-18 semi preparative column, 35% MeCN/65% $H_2O$, 3 mL/min) to give (−)-I(y) as a colorless oil (7 mg, 18% from III, $t_R$ 91.5 min), (+)-I(x) as a colorless oil (7 mg, 18% from III, $t_R$ 97.2 min) and (−)-I(z) as a colorless oil (7 mg, 18% from III, $t_R$.84.0 min). (−)-I(y): $[\alpha]^{25}_D$ −15.4 (c 0.68, $CHCl_3$); 1H NMR (400 MHz/$CDCl_3$) δ 6.37 (d, J=10.8 Hz, 1H), 6.10 (d, J=11.6 Hz, 1H), 5.36 (s, 1H), 5.32 (s, 1H), 5.01 (s, 1H), 4.45 (m, 1H), 4.23 (m, 1H), 2.83 (d, J=12.0 Hz, 1H), 2.60 (d, J=13.6 Hz, 1H), 2.46–2.18 (m, 8H), 2.05–1.54 (m, 16H), 1.22 (s, 9H), 1.10 (d, J=6.8 Hz, 3H), 0.67 (s, 3H); $^{13}C$ NMR (100 MHz, $CDCl_3$) δ 158.02, 147.56, 142.16, 133.20, 124.82, 121.59, 117.00, 111.83, 70.81, 66.82, 58.30, 52.78, 50.04, 45.22, 43.43, 42.84, 35.20, 29.69, 29.41, 28.71, 23.53, 22.92, 22.00, 17.07; IR (neat, $cm^{-1}$) 3364, 2926, 1640, 1461, 1367, 1012; UV (EtOH) $\lambda_{max}$ 262 nm (ε 17,206); HRMS m/z (M$^+$) calcd for $C_{27}H_{42}O_3S$ 447.2933, found 447.2927. (+)-I(x): $[\alpha]^{25}_D$+ 0.002 (c 0.80, $CHCl_3$); $^1H$ NMR (400 MHz/$CDCl_3$) δ 6.37 (d, J=10.8 Hz, 1H), 6.11 (d, J=11.6 Hz, 1H), 5.36 (s, 1H), 5.34 (s, 1H), 5.01 (s, 1H), 4.44 (m, 1H), 4.24 (m, 1H), 2.83 (d, J=12.4 Hz, 1H), 2.60 (d, J=13.6, 1H), 2.50–2.18 (m, 8H), 2.05–1.69 (m, 16H), 1.23 (s, 9H), 1.10 (d, J=6.8 Hz, 3H), 0.69 (s, 3H); $^{13}$C NMR (100 MHz, CDCl$_3$) δ 158.63, 147.58, 142.20, 133.15, 124.85, 121.25, 116.98, 111.75, 70.77, 66.83, 58.35, 50.18, 45.20, 43.75, 42.87, 35.12, 32.50, 30.14, 29.68, 29.42, 28.73, 23.51, 22.89, 21.6, 16.93; IR (neat, cm$^{-1}$) 3304, 2926, 1640, 1462, 1368, 1057; UV (EtOH) $\lambda_{max}$ 262 nm (ε 12,550); HRMS m/z (M$^+$) calcd for C$_{27}$H$_{42}$O$_3$S 447.2933, found 447.2923. I(z) [α]$^{25}$D –15.9 (c 0.68, CHCl$_3$); $^1$H NMR (400 MHz/CDCl$_3$) δ 6.38 (d, J=11.6 Hz, 1H), 6.10 (d, J=11.6 Hz, 1H), 5.36 (s, 1H), 5.32 (s, 1H), 5.01 (s, 1H), 4.45 (m, 1H), 4.22 (m, 1H), 2.82 (m, 1H), 2.61 (dd, J=13.4, 3.8, 1H), 2.45–2.18 (m, 8H), 2.08–1.51 (m, 16H), 1.22 (s, 9H), 1.10 (d, J=7.2 Hz, 3H), 0.67 (s, 3H); $^{13}$C NMR (100 MHz, CDCl$_3$) δ 158.02, 147.26, 142.22, 133.05, 124.82, 121.59, 116.97, 112.49, 71.28, 66.77, 58.29, 52.77, 50.06, 45.43, 43.46, 42.84, 35.18, 29.69, 29.44, 28.69, 23.51, 22.92, 21.97, 17.09; IR (neat, cm$^{-1}$) 3304, 2916,1640, 1462, 1367, 1265, 1012; UV (EtOH) $\lambda_{max}$ 262 nm (ε 12,131); HRMS m/z (M$^+$) calcd for C$_{27}$H$_{42}$O$_3$S 447.2933, found 447.2933.

Example 12

Preparation of Isopropyl Phenyl Sulfone (VII, R$^4$=Ph, R$^6$,R$^7$=Me)

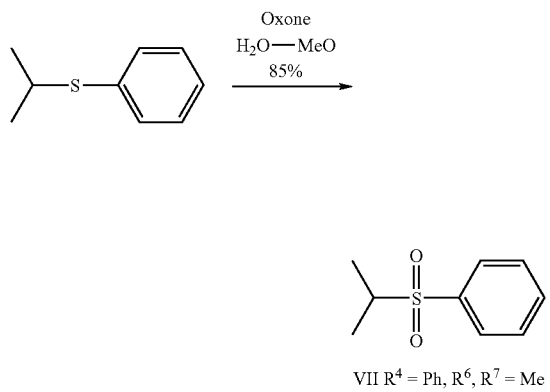

To a solution of isopropyl phenyl sulphide (500 mg, 3.28 mmol) in MeOH (20 mL) was added a solution of potassium peroxymonosulfate (2KHSO$_5$ KHSO$_4$ K$_2$SO$_4$, Oxone®) (3.03 g, 9.85 mmol) in water (20 mL) at 0 ° C. The resulting white suspension was warmed to room temperature and then stirred for 5 h. The mixture was diluted with water (10 mL), extracted with EtOAc (80 mL×2), washed with brine, dried over MgSO$_4$, concentrated in vacuo, and then purified by column chromatography (25% EtOAc/hexanes) to give 512 mg (85%) of isopropyl phenyl sulfone VII (R$^4$=Ph, R$^6$,R$^7$=Me) as a colorless oil: $^1$H NMR (400 MHz, CDCl$_3$) δ 7.74–7.64 (m, 2H), 7.55–7.51 (m, 1H), 7.46–7.42 (m, 2H), 3.08 (septet, J=6.8 Hz, 1H), 1.50 (d, J=6.8 Hz, 6H); $^{13}$NMR (100 MHz, CDCl$_3$) δ 136.54, 133.31, 128.73, 128.55, 55.05, 15.26.

Example 13

Preparation of Cyclopropyl Phenyl Sulfone VII (R$^4$=Ph, R$^6$,R$^7$=cyclopropyl)

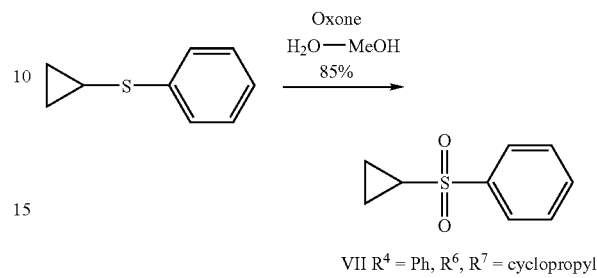

To a solution of cyclopropyl phenyl sulphide (450 mg, 3.00 mmol) in MeOH (15 mL) was added a solution of potassium peroxymonosulfate (2KHSO$_5$KHSO$_4$K$_2$SO$_4$, Oxone®) (5.52 g, 8.99 mmol) in water (15 mL) at 0 ° C. The resulting white suspension was warmed to room temperature and then stirred for 5 h. The mixture was diluted with water (10 mL), extracted with EtOAc (60 mL×2), washed with brine, dried over MgSO$_4$, concentrated in vacuo, and then purified by column chromatography (25% EtOAc/hexanes) to give 494 mg (91%) of cyclopropyl phenyl sulfone VII (R$^4$=Ph, R$^6$,R$^7$=cyclopropyl) as a colorless oil: $^1$H NMR (400 MHz, CDCl$_3$) δ 7.92–7.90 (m, 2H). 7.66–7.62 (m, 1H), 7.58–7.54 (m, 2H), 3.08 (m, 1H), 1.38–1.33 (m, 2H), 1.06–1.00 (m, 2H); $^{13}$NMR (100 MHz, CDCl$_3$) δ 140.67, 133.33, 129.19, 127.53, 32.89, 5.94.

Example 14

Preparation of 22-Iodo Silyl Ether VI

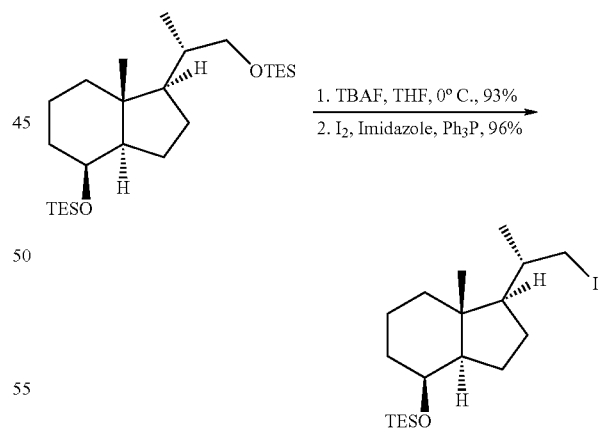

To a solution of bis-silylated diol (508 mg, 1.15 mmol) in 10 mL of anhydrous THF was added 1.15 mL of TBAF (1M in THF) dropwise at 0 ° C. After being stirred for 1 h at 0° C., the reaction mixture was extracted with EtOAc (30 mL×2), washed with brine, dried over MgSO$_4$, concentrated in vacuo, and then purified by column chromatography (20% EtOAc/hexanes) to give 351 mg (93%) of monosilylated alcohol as a colorless oil. To a solution of triphenylphosphine (986 mg, 3.76 mmol), imidazole (578 mg, 8.49 mmol) in 20 mL of $CH_2Cl_2$ was slowly added a solution of iodine (954 mg, 3.76 mmol) in 30 mL of $CH_2Cl_2$ at 0° C. After 15 min, a solution of mono-silylated alcohol (351 mg, 1.07 mmol) in 10 mL of $CH_2Cl_2$ was added into the mixture. After being stirred for 6 h at room temperature, the reaction mixture was extracted with EtOAc (100 mL×2), washed with brine, dried over $MgSO_4$, concentrated in vacuo, and then purified by column chromatography (100% Hexanes) to give 448 mg (96%) of 22-iodo silyl ether VI (-----=single bond) as a colorless oil: $^1$H NMR (400 MHz, $CDCl_3$) δ 4.03 (m, 1H), 3.33 (dd, J=9.6, 2.8 Hz, 1H), 3.18 (dd, J=9.6, 5.2 Hz, 1H), 1.92–1.75 (m, 3H), 1.70–1.55 (m, 2H), 1.43–1.06 (m, 8H), 0.99 (d, J=6.0 Hz, 3H), 0.94 (t, J=8.0 Hz, 9H), 0.94 (s, 3H), 0.55 (q, J=8.0 Hz, 6H).

Example 15

Preparation of Compounds I(aa) and I(bb)

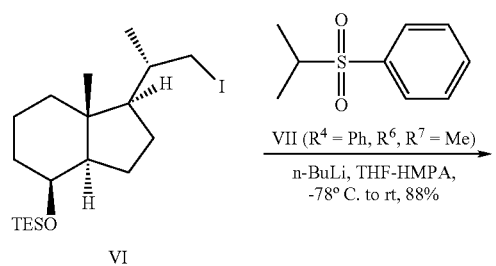

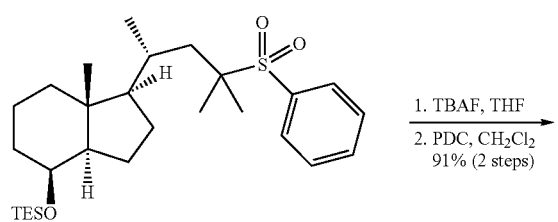

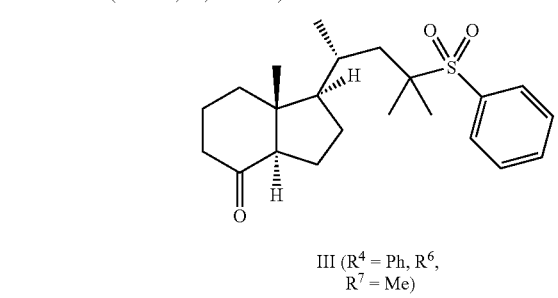

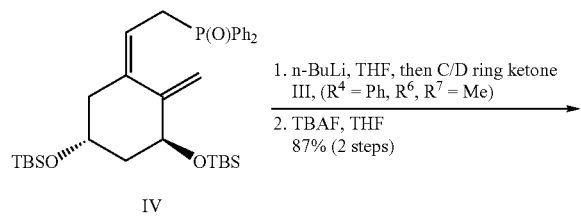

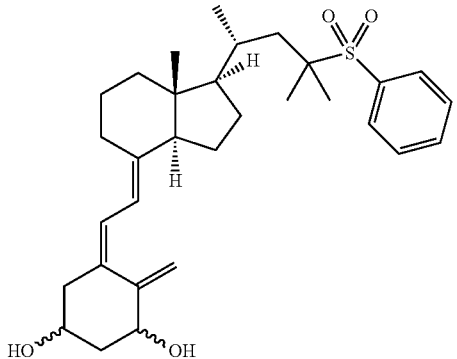

(+)-I(aa) 23-Dimethyl-24-SO2Ph (1α, 3β)
(-)-I(bb) 23-Dimethyl-24-SO2Ph (1β, 3α)

(a) 23-Dimethyl Silyl Ether V ($R^4$=Ph, $R^6$,$R^7$=Me): To a solution of isopropyl phenyl sulfone VII ($R^4$=Ph, $R^6$,$R^7$=Me, Example 12) (38mg, 0.21 mmol) in THF (3mL) at –78° C. was added 0.13 mL (0.21 mmol) of n-BuLi (1.6 M in hexanes). After 15 min stirring, 0.3 mL of HMPA was added at –78° C. After another 15 min stirring, a precooled (–78° C.) solution of iodide VI (-----=single bond, Example 14) (30 mg, 0.069 mmol) in THF (1 mL) was added at –78° C. The reaction mixture was slowly warmed to room temperature and stirred for 2 h, and then quenched with water, extracted with ether (50 mL×2), washed with brine, dried over $MgSO_4$, concentrated in vacuo, and then purified by column chromatography (20% EtOAc/hexanes) to give 30 mg (88%) of 23-dimethyl silyl ether V ($R^4$=Ph, $R^6$,$R^7$=Me) as a colorless oil: $[α]^{24.4}_D$ +27.7 (c 0.57, $CHCl_3$); $^1$H NMR (400 MHz, $CDCl_3$) δ 7.88–7.85 (m, 2H), 7.66–7.62 (m, 1H), 7.57–7.53 (m, 2H), 4.00 (m, 1H), 1.94–1.84 (m, 2H), 1.81–1.60 (m, 6H), 1.57–1.40 (m, 4H), 0.91(t, J=8.0 Hz, 9H), 0.54 (q, J=8.0 Hz, 6H), 1.34 (s, 3H), 1.30 (s, 3H), 1.26 (s, 3H), 1.14–1.04 (m, 4H), 0.95 (d, J=6.0 Hz, 3H); $^{13}$NMR (100 MHz, $CDCl_3$) δ 135.45, 133.39, 130.67, 128.58, 69.32, 64.10, 57.77, 53.08, 42.23, 40.71, 39.40, 34.50, 32.12, 29.70, 27.90, 22.82, 21.10, 17.59, 14.13. 13.28, 6.94, 4.92; IR (neat, $cm^{-1}$) 2949, 2925, 2872, 1463, 1448, 1378, 1366, 1294, 1282, 1164, 1121, 1075, 1002, 730; HRMS m/z ($M^+$+$Na^+$) calcd 515.2986 for $C_{28}H_{48}O_3SSiNa^+$, found 515.2966.

(b) 23-Dimethyl C,D-ring Ketone III ($R^4$=Ph, $R^6$,$R^7$=Me). To a solution of silyl ether V ($R^4$=Ph, $R^6$,$R^7$=Me) (40 mg, 0.080 mmol) in THF (3 mL) was added 0.24 mL (0.24 mmol) of a 1.0 M solution of TBAF in THF, and then it was stirred at 0° C. for 1 h and stirred overnight at room temperature. The reaction mixture was quenched with water (5 mL), extracted with EtOAc (10 mL×2), washed with brine, dried over $MgSO_4$, concentrated in vacuo, and then purified by column chromatography (25% EtOAc/hexanes) to give 30 mg (99%) of alcohol as a white solid. To a solution of the C,D-ring alcohol (30 mg, 0.080 mmol) in $CH_2Cl_2$ (6 mL) was added 80 mg of oven-dried Celite and PDC (84 mg, 0.22 mmol) at room temperature. The reaction mixture was stirred overnight and then passed through a 2 cm pad of flash silica gel and washed with EtOAc. The filtrate was concentrated and purified by column chromatography (33% EtOAc/hexanes) to give 28 mg (91%)

of the desired C,D-ring ketone III (R⁴=Ph, R⁶,R⁷=Me) as a white solid: mp 149–151° C.; $[\alpha]^{24.7}_D$ +22.3 (c 0.96, CHCl₃); ¹H NMR (400 MHz, CDCl₃) δ 7.85–7.82 (m, 2H), 7.65–7.61 (m, 1H), 7.55–7.51 (m, 2H), 2.41 (dd, J=12.4, 11.2 Hz, 1H), 2.28–2.15 (m, 2H), 2.11–2.06 (m, 1H), 1.96 (m, 1H), 1.91–1.79 (m, 3H), 1.73–1.62 (m, 2H), 1.60–1.43 (m, 6H), 1.32 (s, 3H), 1.27 (s, 3H), 1.00 (d, J=5.6 Hz, 2H), 0.61 (s, 3H); ¹³NMR (100 MHz, CDCl₃) δ 211.67, 135.29, 133.52, 130.63, 128.66, 63.81, 61.92, 57.62, 49.74, 40.87, 39.48, 38.89, 32.31, 28.03, 23.91, 22.34, 21.26, 21.24, 18.90, 12.31; IR (neat, cm⁻¹) 2959, 1715, 1442, 1378, 1305, 1140, 1084, 730, 695; HRMS m/z (M⁺+Na⁺) calcd 399.1964 for $C_{22}H_{32}O_3SNa+$, found 399.1968.

(c) 23-Dimethyl-24-SO₂Ph analogues (+)-I(aa) and (−)-I(bb). A solution of 63 mg (0.11 mmol) of racemic phosphine oxide (±)-IV in 2.0 mL of anhydrous THF was cooled to −78° C. and treated with 67.6 μL (0.11 mmol, 1.6 M in hexanes) of n-BuLi under argon atmosphere. The mixture turned reddish orange and was stirred for 10 min at −78° C. To the solution was added dropwise a solution of 33 mg (0.088 mmol) of the C,D-ring ketone III (R⁴=Ph, R⁶,R⁷=Me) in 1.0 mL of anhydrous THF. The reaction kept going until the reddish orange color faded to yellow (about 4 h). The reaction was quenched by adding 3.0 mL of pH 7 buffer, then warmed to room temperature, extracted with EtOAc (30 mL×2), washed with brine, dried over MgSO₄, concentrated in vacuo, and then purified by column chromatography (10% EtOAc/hexanes) to afford 30 mg (54%) of the coupled product as a colorless oil.

The coupled product (30 mg, 0.040 mmol) was dissolved in 3 mL of anhydrous THF, and to this solution was added 0.16 mL (0.16 mmol) of a 1.0 M solution of TBAF in THF. The reaction was run in darkness overnight, then extracted with EtOAc (30 mL×2), washed with brine, dried over MgSO₄, concentrated in vacuo, and then purified by column chromatography (80% EtOAc/hexanes) to give 14 mg (67%) of a mixture of two diastereomers as a white solid. The diastereomers were separated by reverse-phase HPLC (C-18 semipreparative column, 49% MeCN/H₂O, 3.0 mL/min) to afford 2.5 mg (12%) of (+)-I(aa) (1α,3β, $t_R$ 116 min) and trace amount of (−)-I(bb) (1α,3β, $t_R$ 111 min) as foaming solids. (+)-I(aa): $[\alpha]^{24.2}_D$ +25.1 (c 0.12, CHCl₃); ¹H NMR (400 MHz, CDCl₃) δ 7.88–7.85 (m, 2H), 7.67–7.63 (m, 1H), 7.57–7.54 (m, 2H), 6.36 (d, J=11.2 Hz, 1H), 6.00 (d, J=11.2 Hz, 1H), 5.32 (s, 1H), 4.98 (s, 1H), 4.43 (m, 1H), 4.23 (m, 1H), 2.82 (m, 1H), 2.60 (m, 1H), 2.31 (m, 1H), 2.03–1.82 (m, 8H), 1.70–1.44 (m, 1OH), 1.34 (s, 3H), 1.30 (s, 3H), 1.00 (d, J=5.6 Hz, 3H), 0.54 (s, 3H); ¹³NMR (100 MHz, CDCl₃) δ 147.58, 142.66, 135.38, 133.45, 133.09, 130.66, 128.62, 124.84, 117.21, 111.75, 70.75, 66.81, 63.99, 57.52, 56.31, 45.84, 45.11, 42.79, 40.42, 39.53, 32.85, 28.96, 28.11, 23.46, 22.43, 22.10, 21.30, 21.05, 11.86; IR (neat, cm⁻¹) 3436, 2931, 2861, 1719, 1649, 1443, 1296, 1155, 1126, 1073, 756, 568; UV (MeOH) $\lambda_{max}$ 264 nm (ε 5774); HRMS m/z (M⁺+Na⁺) calcd 535.2853 for $C_{31}H_{44}O_4SNa+$, found 535.2898.

Example 16

Preparation of Compounds I(cc) and I(dd)

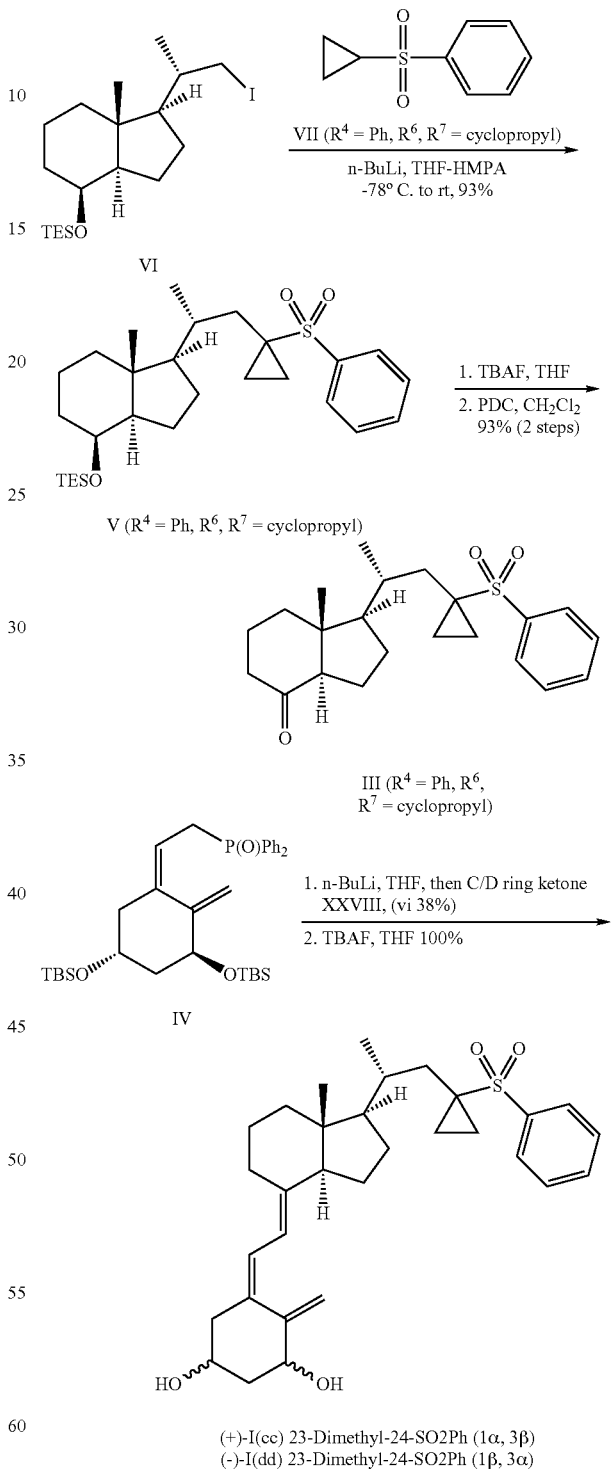

(a) 23-Cyclopropyl Silyl Ether V (R⁴=Ph, R⁶,R⁷=cyclopropyl): To a solution of cyclopropyl phenyl sulfone VII (R⁴=Ph, R⁶,R⁷=cyclopropyl) (Example 13, 50 mg, 0.27 mmol) in THF (3mL) at −78° C. was added 0.17 mL (0.27 mmol) of nBuLi (1.6 M in hexanes). After 15 min stirring, 0.3 mL of HMPA was added at −78° C. After another 15 min stirring, a precooled (−78° C.) solution of iodide VI (Example 14, 40 mg, 0.091 mmol) in THF (1 mL) was added at −78° C. The reaction mixture was slowly warmed to room temperature and stirred for 3 h, and then quenched with water, extracted with ether (50 mL×2), washed with brine, dried over MgSO$_4$, concentrated in vacuo, and then purified by column chromatography (15% EtOAc/hexanes) to give 41 mg (93%) of 23-cyclopropyl silyl ether V (R$^4$=Ph, R$^6$,R$^7$=cyclopropyl) as a colorless oil: $[\alpha]^{23.8}_D$ +22.2 (c 1.85, CHCl$_3$); $^1$H NMR (400 MHz, CDCl$_3$) δ 7.90–7.87 (m, 2H), 7.66–7.61 (m, 1H), 7.58–7.53 (m, 2H), 3.98 (m, 1H), 2.10–2.06 (m, 1H), 1.90–1.85 (m, 1H), 1.83–1.71 (m, 2H), 1.66–1.43 (m, 5H), 1.34–1.22 (m, 3H), 1.15–1.01 (m, 2H), 0.94(t, J=8.0 Hz, 9H), 0.96–0.80 (m, 2H), 0.85 (s, 3H), 0.78 (d, J=6.4 Hz, 3H), 0.74–0.69 (m, 3H), 0.54 (q, J=8.0 Hz, 6H); $^{13}$NMR (100 MHz, CDCl$_3$) δ 139.18, 133.26, 128.88, 128.73, 69.22, 57.38, 52.93, 42.29, 40.65, 39.29, 37.43, 34.50, 33.56, 27.28, 22.88, 18.81, 17.57, 13.52. 12.57, 12.08, 6.93, 4.90; IR (neat, cm$^{-1}$) 2949, 2875, 1446, 1304, 1142, 1084, 1021, 974, 807, 727, 690; HRMS m/z (M$^+$+Na$^+$) calcd 513.2829 for C$_{28}$H$_{46}$O$_3$SSiNa$^+$, found 513.2863.

(b) 23-Cycolpropyl C,D-ring Ketone III (R$^4$=Ph, R$^6$,R$^7$=cyclpropyl) To a solution of silyl ether V (R$^4$=Ph, R$^6$,R$^7$=cyclopropyl) (36 mg, 0.073 mmol) in THF (3.0 mL) was added 0.22 mL (0.22 mmol) of a 1.0 M solution of TBAF in THF, and then it was stirred at 0° C. for 1 h and stirred overnight at room temperature. The reaction mixture was quenched with water (4 mL), extracted with EtOAc (10 mL×2), washed with brine, dried over MgSO$_4$, concentrated in vacuo, and then purified by column chromatography (30% EtOAc/hexanes) to give 27 mg (99%) of alcohol as a colorless oil.

To a solution of the C,D-ring alcohol (27 mg, 0.073 mmol) in CH$_2$Cl$_2$ (5 mL) was added 70 mg of oven-dried Celite and PDC (77 mg, 0.21 mmol) at room temperature. The reaction mixture was stirred overnight and then passed through a 2 cm pad of flash silica gel and washed with EtOAc. The filtrate was concentrated and purified by column chromatography (33% EtOAc/hexanes) to give 26 mg (93%) of the desired C,D-ring ketone III (R$^4$=Ph, R$^6$,R$^7$=cyclopropyl) as a white solid: mp 125–127° C.; $[\alpha]^{24.5}_D$ +3.62 (c 1.20, CHCl$_3$); $^1$HNMR (400 MHz, CDCl$_3$) δ 7.88–7.86 (m, 2H), 7.66–7.62 (m, 1H), 7.57–7.53 (m, 2H), 2.35 (dd, J=11.6, 11.2 Hz, 1H), 2.29–2.14 (m, 2H), 2.08–2.04 (m, 2H), 2.00–1.95 (m, 1H), 1.89–1.78 (m, 2H), 1.72–1.41 (m, 6H), 1.23 (m, 1H), 1.00–0.95 (m, 2H), 0.90 (d, J=6.4 Hz, 3H), 0.85 (m, 1H), 0.73–0.69 (m, 1H), 0.59 (s, 3H); $^{13}$NMR (100 MHz, CDCl$_3$) δ 211.62, 139.02, 133.43, 128.98, 128.60, 61.74, 57.19, 49.87, 40.85, 39.16, 38.85, 37.85, 33.96, 27.34, 23.90, 18.98, 18.82, 12.76, 12.53, 12.31; IR (neat, cm$^{-1}$) 2958, 1710, 1446, 1379, 1302, 1141, 1083, 728, 692, 643; HRMS m/z (M$^+$+Na$^+$) calcd 397.1808 for C$_{22}$H$_{30}$O$_3$SNa$^+$, found 397.1807.

(c) 23-Cyclopropyl-24-SO$_2$Ph analogues (+)-I(cc) and (−)-I(dd). A solution of 57 mg (0.098 mmol) of racemic phosphine oxide (±)-IV in 2.0 mL of anhydrous THF was cooled to −78° C. and treated with 61.1 μL (0.098 mmol; 1.6 M in hexanes) of n-BuLi under argon atmosphere. The mixture turned reddish orange and was stirred for 10 min at −78° C. To the solution was added dropwise a solution of 17 mg (0.046 mmol) of the C,D-ring ketone III (R$^4$=Ph, R$^6$,R$^7$=cyclopropyl) in 1.0 mL of anhydrous THF. The reaction kept going until the reddish orange color faded to yellow (about 2.5 h). The reaction was quenched by adding 2.0 mL of pH 7 buffer, then warmed to room temperature, extracted with EtOAc (20 mL×2), washed with brine, dried over MgSO$_4$, concentrated in vacuo, and then purified by column chromatography (30% EtOAc/hexanes) to afford 13 mg (38%) of the coupled product as a colorless oil.

The coupled product (13 mg, 0.018 mmol) was dissolved in 3 mL of anhydrous THF, and to this solution was added 0.07 mL (0.07 mmol) of a 1.0 M solution of TBAF in THF. The reaction was run in darkness overnight, then extracted with EtOAc (20 mL×2), washed with brine, dried over MgSO$_4$, concentrated in vacuo, and then purified by column chromatography (80% EtOAc/hexanes) to give 10 mg (100%) of a mixture of two diastereomers as a white solid. The diastereomers were separated by reverse-phase HPLC (C-18 semipreparative column, 50% MeCN/H$_2$O, 3.0 mL/min) to afford 2.6 mg (26%) of (+)-I(cc) (1α,3β, t$_R$ 74 min) and trace amount of (−)-I(dd) (1β,3α, t$_R$ 71 min) as foaming solids. (+)-I(cc): $[\alpha]^{24.1}_D$ +18.6 (c 0.22, CHCl$_3$); $^1$H NMR (400 MHz, CDCl$_3$) δ 7.90–7.87 (m, 2H), 7.67–7.62 (m, 1H), 7.58–7.54(m, 2H), 6.36 (d, J=11.2 Hz, 1H), 5.99 (d, J=11.2 Hz, 1H), 5.33 (s, 1H), 4.99 (s, 1H), 4.43 (m, 1H), 4.23 (m, 1H), 2.79 (m, 1H), 2.59 (m, 1H), 2.30 (m, 1H), 2.10–1.87 (m, 4H), 1.82–1.74 (m, 2H), 1.28–1.19 (m, 2H), 1.11–1.07 (m, 2H), 1.67–1.53 (m, 8H), 1.00–0.93 (m, 2H), 0.86 (d, J=6.4 Hz, 3H), 0.74–0.68 (m, 2H), 0.50 (s, 3H); $^{13}$NMR (100 MHz, CDCl$_3$) δ 147.61, 142.71, 139.14, 133.34, 133.06, 128.94, 128.68, 124.88, 117.18, 111.78, 70.83, 57.13, 56.17, 45.96, 45.23, 42.86, 40.36, 39.26, 37.78, 34.45, 28.97, 27.54, 23.45, 22.21, 18.99, 12.64, 12.23, 12.04; IR (neat, cm$^{-1}$l) 3401, 2944, 2861, 1647, 1445, 1303, 1142, 1077, 1053, 721, 691, 573.

Example 17

Preparation of Compounds I(ee) and I(ff)

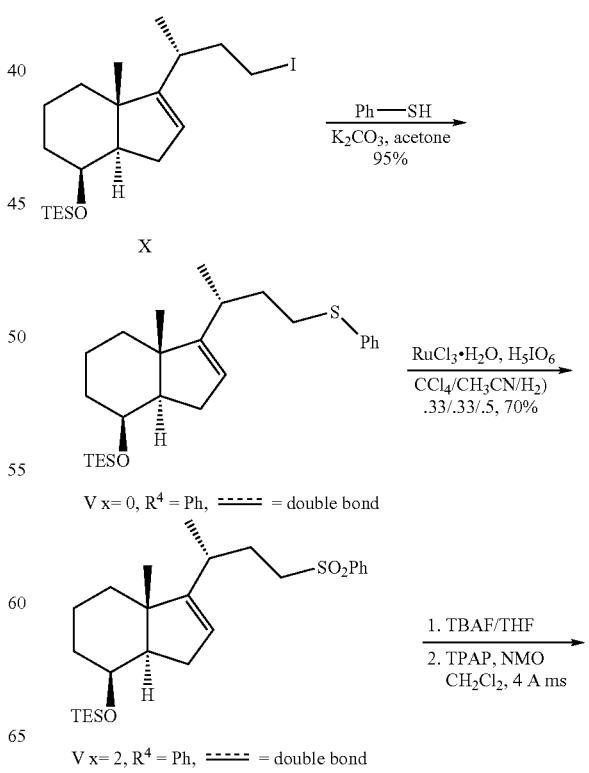

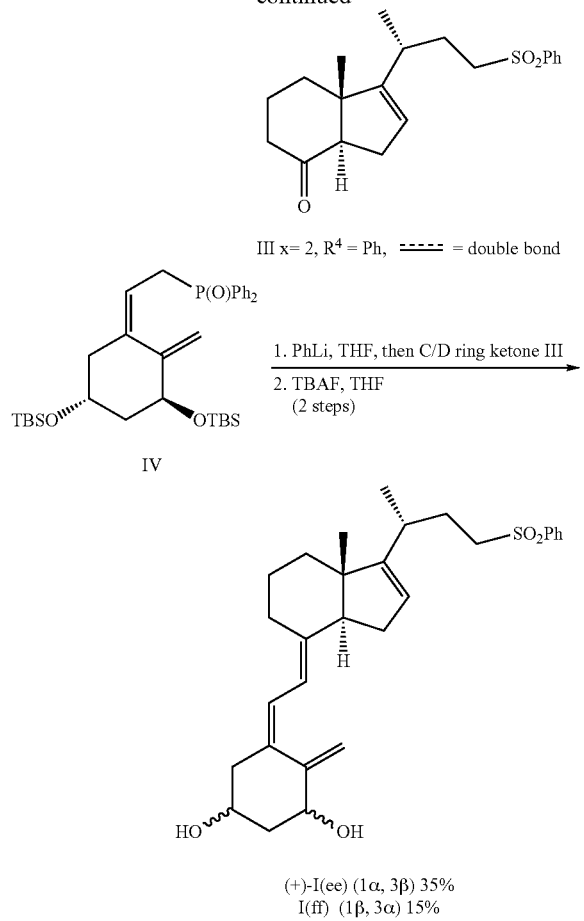

III x=2, R⁴ = Ph, ----- = double bond (+)-I(ee) (1α, 3β) 35%
I(ff) (1β, 3α) 15%

(a) Compound V (x=0, -----double bond, R⁴=Ph). To a flask, 25 mL, containing iodide X (-----=double bond) (45 mg, 0.100 mmol) was added acetone (2 mL), $K_2CO_3$ (70 mg, 0.502 mmol) and finally thiophenol (52 μL, 0.502 mmol) via a syringe. This mixture was stirred at rt. for 1.5 h and quenched with pH 7.0 phosphate buffer (2 mL). The reaction was extracted with $Et_2O$ (3×, 20 mL), dried over $MgSO_4$, reduced under pressure and purified by silica gel chromatography (100% petroleum ether) to give 45 mg of product as an oil (95%): $[\alpha]^{25}_D$ +18.02 (c 0.3925, $CHCl_3$); ¹H NMR (400 MHz, $CDCl_3$) δ 7.27 (m, 4H), 7.14 (m, 1H), 5.25 (m, 1H), 4.10 (d, J=2.4 Hz, 1H), 2.91 (ddd, J=12.8, 9.6, 5.6 Hz, 1H), 2.80 (ddd, J=12.8, 9.2, 6.0 Hz, 1H), 2.21 (m, 2H), 1.93–1.77 (m, 3H), 1.72–1.58 (m, 4H), 1.50–1.39 (m, 2H), 1.33 (dt, J=12.8, 3.6 Hz 1H), 0.99 (s, 3H), 0.96 (d, J=6.8 Hz, 3H), 0.94 (t, J=8.0 Hz, 9H), 0.55 (q, J=8.0 Hz, 6H); ¹³C NMR (100 MHz, $CDCl_3$) δ 159.30, 136.93, 128.84, 128.76, 125.58, 120.22, 68.91, 55.07, 48.77, 46.65, 35.68, 34.91, 31.69, 31.05, 30.74, 22.36, 18.72, 18.04, 6.94, 4.91; IR ($CHCl_3$, cm⁻¹) 3025, 2954, 1586, 1456, 1028; HRMS m/z (M⁺) calcd 453.261780 for $C_{26}H_{42}OSSiNa^+$ found 453.26329.

(b) Compound (+)-V (x=2, -----=double bond, R⁴=Ph). To a flask, 10 mL, was sequentially added sulfide V (x=0, -----=double bond, R⁴=Ph) (40 mg, 0.093 mmol), $CCl_4$ (0.5 mL), $CH_3CN$ (0.5 mL), $H_2O$ (1 mL) and $H_5IO_6$ (45 mg, 0.195 mmol). This mixture was stirred vigorously for 5 min at rt., after which was added $RuCl_3 \cdot H_2O$ (0.4 mg, 0.0018 mmol) turning the reaction a dark green color. The reaction was stirred until all starting material and intermediate sulfoxide had disappeared by TLC (~2 h) and then passed over a plug of silica gel. The organics were reduced under pressure and purified by silica gel chromatography (85% petroleum ether, 15% ethyl acetate) to give 30 mg of product as an oil (70%): $[\alpha]^{25}_D$ +21.5 (c 0.893, $CHCl_3$); ¹H NMR (400 MHz, $CDCl_3$) δ 7.90 (m, 2H), 7.65 (m, 1H), 7.57 (m, 2H), 5.11 (m, 1H), 4.09 (d, J=2.4 Hz, 1H), 3.12 (ddd, J=14.0, 10.8, 4.8 Hz, 1H), 2.97 (ddd, J=14.0, 11.2, 5.6 Hz, 1H), 2.20 (tt, J=12.8, 1.2 Hz, 1H), 2.07 (m, 1H), 1.89–1.72 (m, 4H), 1.69–1.54 (m, 2H), 1.48–1.37 (m, 2H), 1.25 (m, 2H), 0.96 (d, J=6.8 Hz, 3H), 0.94 (t, J=8.0 Hz, 9H), 0.92 (s, 3H), 0.55 (q, J=8.0 Hz, 6H); ¹³C NMR (100 MHz, $CDCl_3$) δ 157.76, 139.07, 133.54, 129.18, 128.05, 121.13, 68.74, 54.98, 54.69, 46.47, 35.52, 34.75, 30.92, 30.68, 28.66, 22.35, 18.70, 17.93, 6.91, 4.87; IR ($CHCl_3$, cm⁻¹) 3015, 2933, 1448, 1317, 1149, 1083; HRMS m/z (M⁺) calcd 485.251610 for $C_{26}H_{42}O_3SSiNa^+$ found 485.25125.

(c) Compound (+)-III (x=2, -----=double bond, R⁴=Ph). In a flask, 25 mL, was dissolved the sulfone V (x=2, -----=double bond, R⁴=Ph) (28 mg, 0.060 mmol) in THF (1.5 mL). To this was added TBAF (195 μL, 0.195 mmol, 1.0 M in THF) via syringe and the reaction was stirred at rt. for 6 h. The reaction was quenched with water, extracted with $Et_2O$ (3×, 25 mL) and reduced under pressure to give 24 mg of crude product, which was used in the next reaction without further purification.

The crude alcohol was dissolved in $CH_2Cl_2$ (1.5 mL), to which 4 Å ms (~20 mg), NMO (15 mg, 0.130 mmol) and finally TPAP (1.1 mg, 0.0033 mnmol) were added. The reaction was vigorously stirred at rt. for 5 h. The crude reaction mixture was passed over a plug of silica and reduced under pressure. The product was then purified by silica gel chromatography (60% hexanes, 40% ethyl acetate) to give 19.1 mg of product (91%): $[\alpha]^{25}_D$ +22.8 (c 0.955, $CHCl_3$); ¹H NMR (400 MHz, $CDCl_3$) δ 7.89 (m, 2H), 7.64 (m, 1H), 7.57 (m, 2H), 5.16 (m, 1H), 4.09 (d, J=2.4 Hz, 1H), 3.06 (ddd, J=14.0, 10.4, 5.2 Hz, 1H), 2.98 (ddd, J=14.0, 10.4, 5.6 Hz, 1H), 2.80 (m, 1H), 2.40 (ddt, J=15.6, 10.8, 1.6 Hz, 1H), 2.27–2.19 (m, 3H), 2.10–2.01 (m, 2H), 1.99–1.90 (m, 1H), 1.89–1.78 (m, 3H), 1.69 (m, 1H), 1.04 (d, J=7.2 Hz, 3H), 0.73 (s, 3H); ¹³C NMR (100 MHz, $CDCl_3$) δ 210.41, 155.62, 139.04, 133.68, 129.28, 127.99, 121.82, 62.94, 54.39, 53.51, 40.37, 34.16, 31.81, 28.41, 2707, 23.87, 21.57, 17.18; IR ($CHCl_3$, cm⁻¹) 3018, 2935, 1716, 1450, 1337, 1149, 1096; HRMS m/z (M⁺) calcd 369.149483 for $C_{20}H_{26}O_3SNa^+$ found 369.14909.

(d) Preparation of Compounds I(ee) and I(ff): Prior to reaction, phosphine oxide (±)-IV and C,D-ring ketone III (x=2, -----=double bond, R⁴=Ph) were azeotrophically dried with benzene and left under vacuum for 24 h. A solution of n-BuLi in hexanes (67 μL, 0.110 mmol) was added dropwise to a cold (−78° C.) solution of phosphine oxide (i)-IV (64 mg, 0.110 mmol) in THF (1.20 mL) under dry argon. The resulting deep red solution was stirred for 40 min, at which time a cold (−78° C.) solution of C,D-ring ketone III (x=2, -----=double bond, R⁴=Ph) (19.1 mg, 0.0551 mmol) in THF (1.0 mL) was added dropwise via cannula. The resulting solution was stirred at −78° C. in the dark for approximately 4 h, after which the dark red color had faded to a light orange color. The reaction mixture was quenched with pH 7.0 phosphate buffer (1 mL), warmed to rt, extracted with $Et_2O$ (3×20 mL), washed with brine, dried over $MgSO_4$, filtered, concentrated, and purified by silica gel column chromatography (80% hexanes, 20% ethyl acetate) to afford the coupled products as a clear oil (31.5 mg). This oil was immediately dissolved in THF (1.5 mL)

and treated with triethylamine (31 μL, 0.221 mmol) and TBAF (221 μL, 0.221 mmol, 1.0 M in THF) and stirred in the dark for 16 h. The reaction mixture was quenched with H$_2$) (1 mL), extracted with EtOAc (3×15 mL), dried over MgSO$_4$, filtered, concentrated, and purified by silica gel column chromatography (85% ethyl acetate, 15% hexanes) to afford the diol (21 mg) as a mixture of diastereomers. This diastereomeric mixture was separated by HPLC (CHIRAL-CEL OJ) giving enantiomerically pure, vitamin-D$_3$ analogs I(ee) and I(ff) in 35% and 15% yield respectively. I(ee): [α]$^{25}_D$ +14.7 (c 0.230, CHCl$_3$); $^1$H NMR (400 MHz, CDCl$_3$) δ 7.90 (m, 2H), 7.66 (m, 1H), 7.58 (m, 2H), 6.35 (d, J=11.2 Hz, 1H), 6.08 (d, J=11.2 Hz, 1H), 5.34 (m, 1H), 5.18 (m, 1H) 5.00 (m, 1H), 4.44 (m, 1H), 4.24 (m, 1H), 3.08 (ddd, J=14, 10.8, 4.8 Hz, 1H), 2.97 (ddd, J=14.0, 10.8,4.8 Hz, 1H), 2.79 (m, 1H), 2.59 (dd, J=13.6, 3.2 Hz, 1H), 2.32 (m, 2H), 2.17 (m, 2H), 2.07–2.01 (m, 1H), 1.97 (m, 1H), 1.92–1.86 (m, 1H), 1.74 (m, 2H), 1.67–1.51 (m, 2H), 1.40 (m, 1H), 1.02 (d, J=6.8 Hz, 3H), 0.60 (s, 3H); $^{13}$C NMR (100 MHz, CDCl$_3$) δ 157.28, 147.62, 141.86, 139.07, 133.60, 133.31, 129.24, 128.05, 124.73, 121.96, 117.08, 111.66, 70.67, 66.85, 58.26, 54.53, 49.82, 45.15, 42.87, 35.05, 31.95, 29.39, 28.63, 28.50, 23.45, 21.53, 16.82; IR (CHCl$_3$, cm$^{-1}$) 3283, 2948, 2874, 1486, 1326, 1163, 1093; HRMS m/z (M$^+$) calcd 505.238298 for C$_{29}$H$_{38}$O$_4$SNa$^+$ found 505.236512.

Example 18

Preparation of Compounds I(gg) and I(hh)

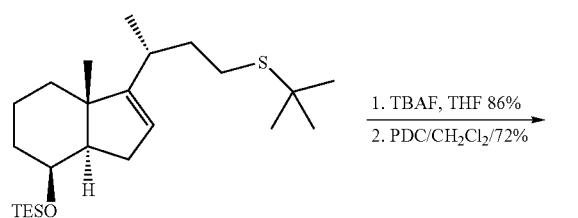

V x = 0, R$^4$ = t-butyl, ----- = dble bond

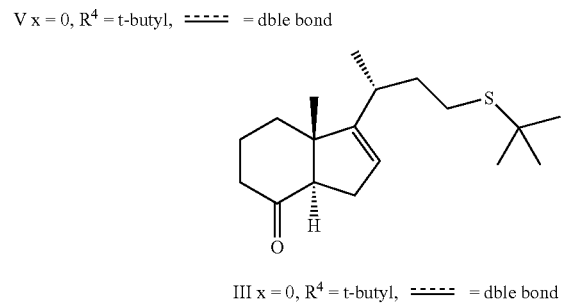

III x = 0, R$^4$ = t-butyl, ----- = dble bond

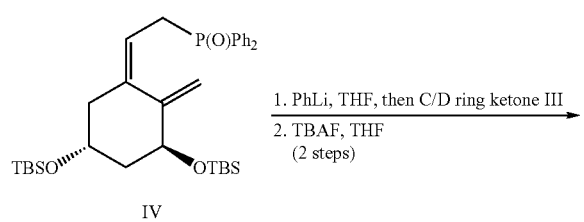

IV

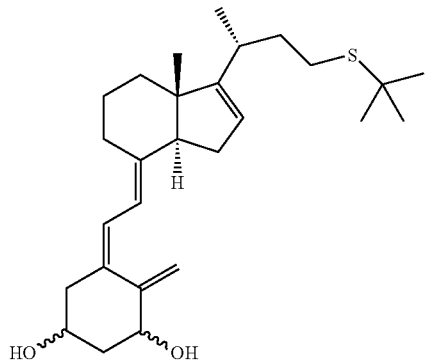

(−)-I(gg) 16-Ene-24-S (1a, 3β) 18%
(+)-I(hh) 16-Ene-24S (1b, 3α) 18%

(a) 16-Ene-8-Keto-24-Sulfide (+)-III (x=0, R$^4$=t-butyl, -----=dble bond): To a solution of triethylsilyl-ether (+)-V (x=0, R$^4$=t-butyl, -----=dble bond, see Example 11a) (90 mg, 0.22 mmol) in 5 mL of THF was added tetrabutylammonium fluoride (1 M in THF, 0.44 mL, 0.44 mmol). After 5 h at rt, the reaction mixture was concentrated in reduced pressure. The residue was purified by flashy chromatography (20% ethyl acetate/hexanes) to give the corresponding alcohol as a coloress oil (57 mg, 86%): [α]$^{25}_D$ +2.6 (c 4.8, CHCl$_3$); $^1$H NMR (400 MHz/CDCl$_3$) δ 5.31 (s, 1H), 4.16 (s, 1H), 2.52–2.39 (m, 2H), 2.26 (tt, J=13.2, 1.2 Hz, 2H), 2.02–1.70 (m, 6H), 1.65–1.34 (m, 5H), 1.28 (s, 9H), 0.99 (d, J=6.8 Hz, 3H), 1.04 (s, 3H); $^{13}$C NMR (100 MHz/CDCl$_3$) δ 159.38, 120.01, 69.06, 54.34, 46.32, 41.80, 36.29, 35.35, 33.87, 31.24, 30.97, 30.20, 26.36, 22.23, 18.32, 17.76; IR (neat, cm$^{-1}$) 3451, 2926, 1458, 1363; HRMS m/z (M$^+$) calcd 296.2174 for C$_{18}$H$_{32}$OS, found 296.2178.

To a solution of the alcohol (39 mg, 0.13 mmol) in 7 mL of dry CH$_2$Cl$_2$ was added 60 mg of oven dried celite and pyridinium dichlomate (60 mg, 0.16 mmol) at rt. After 16 h, the reaction mixture filtered through flashy silica pad, and then eluted with ethyl acetate. The filtrate was concentrated and purified by flash chromatography (20% ethyl acetate/hexanes) to give ketone (+)-V (x=0, R$^4$=t-butyl, -----=dble bond) as a colorless oil (29 mg, 72%): [α]$^{25}$D +14.8 (c 2.4, CHCl$_3$; $^1$H NMR (400 MHz/CDCl$_3$) δ 5.29 (s, 1H), 2.83 (dd, J=10.4, 6.4, 1H), 2.52–2.32 (m, 6H), 2.12–1.58 (m, 12H), 1.28 (s 9H), 1.05 (d, J=6.8 Hz, 3H), 0.81 (s, 3H); $^{13}$C NMR (100 MHz/CDCl$_3$) δ 210.95, 157.33, 120.53, 63.05, 58.82, 41.86, 40.48, 36.11, 34.28, 32.04, 30.94, 27.04, 26.13, 23.98, 21.59, 17.19; IR (neat, cm$^{-1}$) 2959, 1720, 1458, 1363; HRMS m/z (M$^+$) calcd 294.2017 for C$_{18}$H$_{30}$OS, found 294.2018.

(b) 16-Ene-24-Sulfide Calcitriol Analogs I(gg) and I(hh). To a solution of phosphine oxide (±)-IV (50 mg, 0.086 mmol) in 1 mL of anhydrous THF was treated dropwise with phenyl lithium (1.59 M in cyclohexane-ether, 0.054 mL, 0.086 mmol) at −78° C. The resulting reddish orange solution was stirred at −78° C. for 30 min and then a solution of ketone (+)-V (x=0, R$^4$=t-butyl, -----=dble bond) (23 mg, 0.080 mmol) in 1 mL of anhydrous THF was added dropwise. The reaction mixture was stirred until reddish color turned to pale yellow, and then quenched with 3 mL of a 1/1 mixture of 2 N sodium potassium tartrate solution and 2 N $K_2CO_3$ solution. The aqueous layer was extracted with ethyl acetate (50 mL×3). The combined organic extract was with brine (50 mL), dried over $MgSO_4$, and concentrated. The residue was purified by preparative TLC (ethyl acetate) to give coupled products, unreacted CD-ring ketone (+)-V (x=0, $R^4$=t-butyl, -----=dble bond) (9 mg, 39%) and A-ring phosphine oxide IV (21 mg, 41%).

To a solution of the above coupled products in 10 mL of THF was tetrabutylammonium floride (1 M in THF, 0.15 mL, 0.15 mmol). The solution was stirred at rt for 25 h in dark. The reaction mixture was concentrated in reduced pressure. The residue was purified by preparative TLC (ethyl acetate) to give diastereomeric diols I(gg) and I(hh) as colorless oil (16 mg, 47% from (+)-V). The diastereomers were separated by reverse phase HPLC (C-18 semi preparative column, 73% MeCN/27% $H_2O$, 3 mL/min) to give (−)-I(gg) as a colorless oil (6 mg, 17% from (+)-V, $t_R$ 51.5 min) and (−)-I(hh) as a colorless oil (3 mg, 9% from (+)-V, $t_R$ 49.4 min). (−)-I(gg)::$[\alpha]^{25}D$ −8.4 (c 0.65, $CHCl_3$); $^1H$ NMR (400 MHz/$CDCl_3$) δ 6.38 (d, J=11.2 Hz, 1H), 6.11 (d, J=11.2 Hz, 1H), 5.34 (s, 2H), 5.02 (s, 1H), 4.45 (m, 1H), 4.24 (m, 1H), 2.83 (d, J=12.4 Hz, 1H), 2.61 (d, J=12.8, 1H), 2.51–2.19 (m, 7H), 2.03–1.49 (m, 16H), 1.30 (s, 9H), 1.05 (d, J=6.8 Hz, 3H), 0.70 (s, 3H); $^{13}C$ NMR (100 MHz, $CDCl_3$) δ 159.16, 147.58, 142.53, 132.95, 124.92, 120.59, 116.83, 111.72, 70.74, 66.84, 58.35, 50.06, 45.19, 42.83, 41.87, 36.26, 35.21, 32.34, 31.00, 29.68, 29.38, 28.76, 26.29, 23.58, 21.53, 16.86; IR ($CHCl_3$, $cm^{-1}$) 3352, 2925, 1458, 1364, 1216, 1055; UV (EtOH) $\lambda_{max}$ 262 nm (ε 17,253); HRMS m/z ($M^+$) calcd 430.2906 for $C_{27}H_{42}O_2S$, found 430.2901. (−)-I(hh): $[\alpha]^{25}D$ −23.0 (c 0.37, $CHCl_3$); $^1H$ NMR (400 MHz/$CDCl_3$) δ 6.39 (d, J=11.2 Hz, 1H), 6.10 (d, J=11.2 Hz, 1H), 5.32 (s, 2H), 5.02 (s, 1H), 4.45 (m, 1H), 4.22 (m, 1H), 2.83 (d, J=12.4 Hz, 1H), 2.63 (dd, J=13.6, 3.6, 1H), 2.52–2.17 (m, 9H), 2.03–1.51 (m, 12H), 1.30 (s, 9H), 1.05 (d, J=7.2 Hz, 3H), 0.70 (s, 3H); $^{13}C$ NMR (100 MHz/$CDCl_3$) δ 159.17, 147.14, 142.60, 132.79, 124.95, 120.61, 116.83, 112.71, 71.43, 66.77, 58.35, 50.08, 45.49, 42.78, 41.86, 36.29, 35.19, 32.34, 31.01, 29.44, 28.75, 26.29, 23.57, 21.53, 16.88; IR ($CHCl_3$, $cm^{-1}$) 3608, 2928, 1459, 1366, 1046; UV (EtOH) $\lambda_{max}$ 263 nm (ε 15,240); HRMS m/z ($M^+$) calcd 430.2906 for $C_{27}H_{42}O_2S$, found 430.2897.

Example 19

Preparation of Compound I(ii)

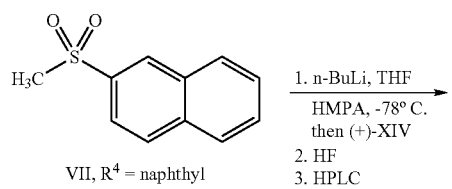

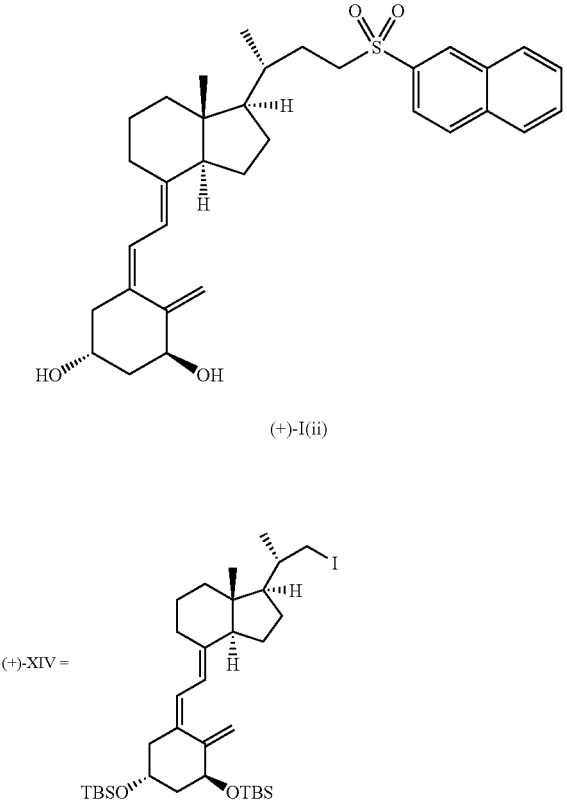

(a) Alkylation of 22-iodide (+)-XIV.

A flame-dried 5-mL recovery flask equipped with a magnetic stir bar, a septum along with an Ar balloon was charged with VII ($R^4$=naphthyl) (6 mg, 0.029 mmol) and dissolved in 0.5 mL freshly distilled THF. Then the flask was cooled down to −78° C. in an isopropanol/dry ice bath. To this solution was added 19 μL of n-BuLi (0.029 mmol, 1.6 M solution in hexanes) dropwise over several minutes followed by addition of 50 μL HMPA, resulting in a yellow color. This mixture was allowed to stir at −78° C. for an additional 30 min. Meanwhile, a flame-dried 5-mL pear shaped flask equipped with a septum along with an Ar balloon was charged with iodide (+)-XIV (Manchand, S. M.; Yiannikouros, G. P.; Belica, P. S.; Madan, P. *J. Org. Chem.* 1995, 60, 6574–6581) (5.0 mg, 0.0073 mmol), dissolved in 0.5 mL freshly distilled THF and cooled down to −78° C. in an isopropanol/dry ice bath. The solution of iodide (+)-XIV was transferred into the flask containing the lithiated sulfone at −78° C. via cannula over a few minutes. After the addition was complete, the mixture was stirred at −78° C. for about 6 hours and then at room temperature for 1 hour. TLC showed almost complete consumption of (+)-XIV. The reaction was quenched by addition of 2 mL pH 7 buffer, then rinsed into a separatory funnel with ethyl acetate. The mixture was extracted with ethyl acetate (3×10 mL). The combined extracts were washed with water (1×10 mL), brine solution (1×10 mL), dried over $Na_2SO_4$ and filtered. The filtrate was concentrated in vacuo to give the crude product that was purified by using silica gel preparative TLC plate eluted with 20% ethyl acetate in hexanes affording 4.2 mg of the protected coupled product in 75% yield.

(b) Deprotection of Coupled Product.

An argon purged 5 mL polypropylene vial equipped with a magnetic stir bar along with a cap was charged with the coupled product from (a) (4.0 mg, 0.0025 mmol) dissolved in 0.25 mL anhydrous acetonitrile to give ca. 0.01 M solution. To this well-stirred solution was added 0.10 μL of HF (0.024 mmol, 49% aqueous solution) via syringe at room temperature and the mixture was then allowed to stir at room temperature in the dark for 4 hours. TLC showed the completion of the reaction. This reaction mixture was diluted with ether (10 mL) and saturated solution of $NaHCO_3$ was added until no more carbon dioxide was liberated. The reaction mixture was then rinsed into a separatory funnel with ethyl acetate and was extracted with ethyl acetate (4×10 mL). The combined extracts were washed with water (1×10 mL), brine solution (1×10 mL), dried over $Na_2SO_4$ and filtered. The filtrate was concentrated in vacuo to give the crude product which was purified by flash column chromatography eluted with 99% ethyl acetate in the presence of 1% triethylamine to afford 2.8 mg of (+)-I(ii) (1α,3β) MK-24-SO$_2$-Naph in 89% yield. This was further purified by HPLC using a Chiralcel OD column (Semipreparative (1×25 cm), flow rate=2.0 mL/min) eluted with 25% isopropyl alcohol in hexanes to afford 2.1 mg (+)-I(ii) (1α,3β) MK-24-SO$_2$-Naph. The retention time for (+)-I(ii) is 35.8 min. Data for (+)-I(ii) (1α,3β) MK-24-SO$_2$-Naph: $[\alpha]_D$ =+52.53 (c=0.10, CHCl$_3$) $^1$H NMR (CDCl$_3$, 400 MHz): δ 8.49 (d, 1H, J=2.0 Hz), 8.03–8.00 (m, 2H), 7.95 (d, 1H, J=8.0 Hz), 7.87 (dd, 1H, J=1.6 Hz, J=8.4 Hz), 7.72–7.63 (m, 2H), 6.35 (d, 1H, J=11.2 Hz), 5.98 (d, 1H, J=11.2 Hz), 5.32 (t, 1H, J=1.6 Hz), 4.98 (t, 1H, J=1,2 Hz), 4.34–4.42 (m, 1H), 4.23–4.22 (m, 1H), 3.25–3.18 (m, 1H), 3.11–3.04 (m, 1H), 2.80 (dd, 1H, J=4.0 Hz, J=12.4 Hz), 2.59 (dd, 1H, J=4.0 Hz, J=13.6 Hz), 2.31 (dd, 1H, J=6.4 Hz, J=13.2 Hz), 2.05–1.86 (m, 5H), 1.79–1.63 (m, 4H), 1.55–1.40 (m, 5H), 1.28–1.18 (mn, 4H), 0.88 (d, 3H, J=6.4 Hz), 0.48 (s, 3H). $^{13}$C NMR (CDCl$_3$, 125 MHz): δ 147.58, 142.57, 136.01, 135.26, 133.14, 132.16, 129.82, 129.56, 129.40, 129.23, 128.0, 127.71, 124.83, 122.71, 117.23, 111.82, 70.11, 66.83, 56.15, 55.70, 53.64, 45.82, 45.23, 42.82, 40.31, 35.03, 28.93, 28.35, 27.32, 23.42, 22.11, 18.47, 11.94. IR: 3365 (m), 2942 (s), 2871 (m), 2837 (w), 1307 (s), 1219 (s), 1143 (m), 1119 (w), 1067 (w), 955 (w), 902 (s) cm$^{-1}$. HRMS: calcd for $C_{33}H_{42}O_4SNa^+$ [M+Na]: 557.2695; found: 557.2682. UV (MeOH) $\lambda_{max}$ 267 nm (ε 17,123).

Example 20

Preparation of Compound I(jj), I(kk), I(ll) and I(mm)

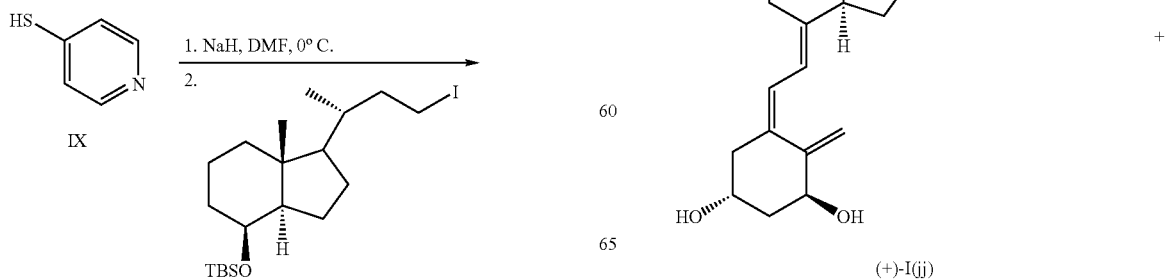

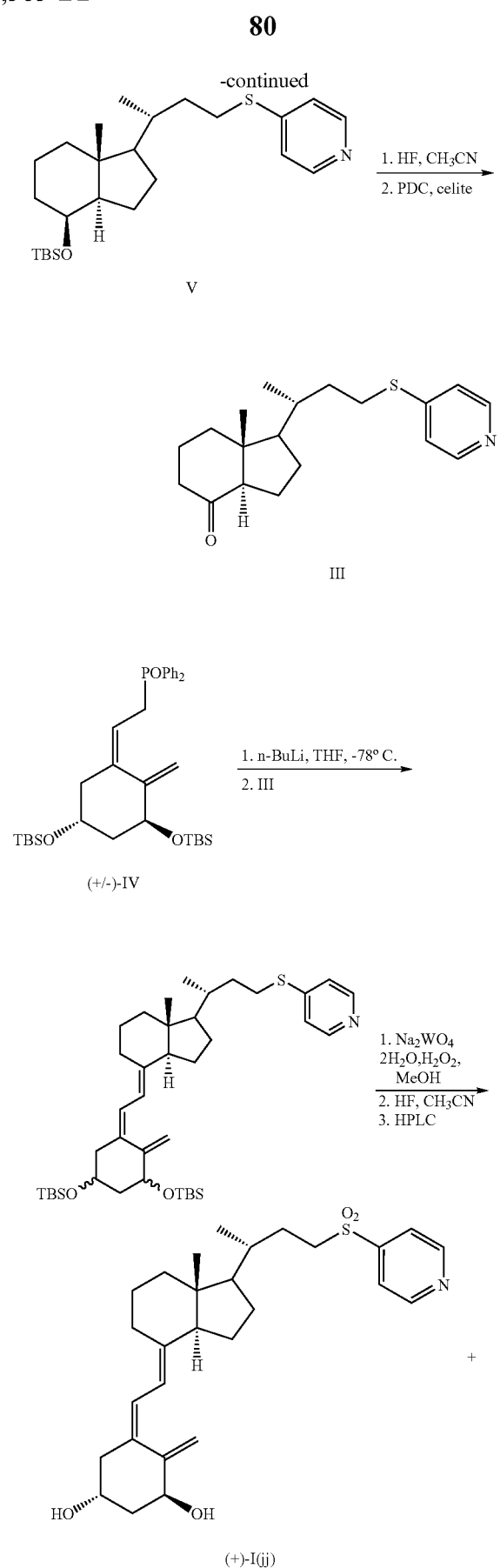

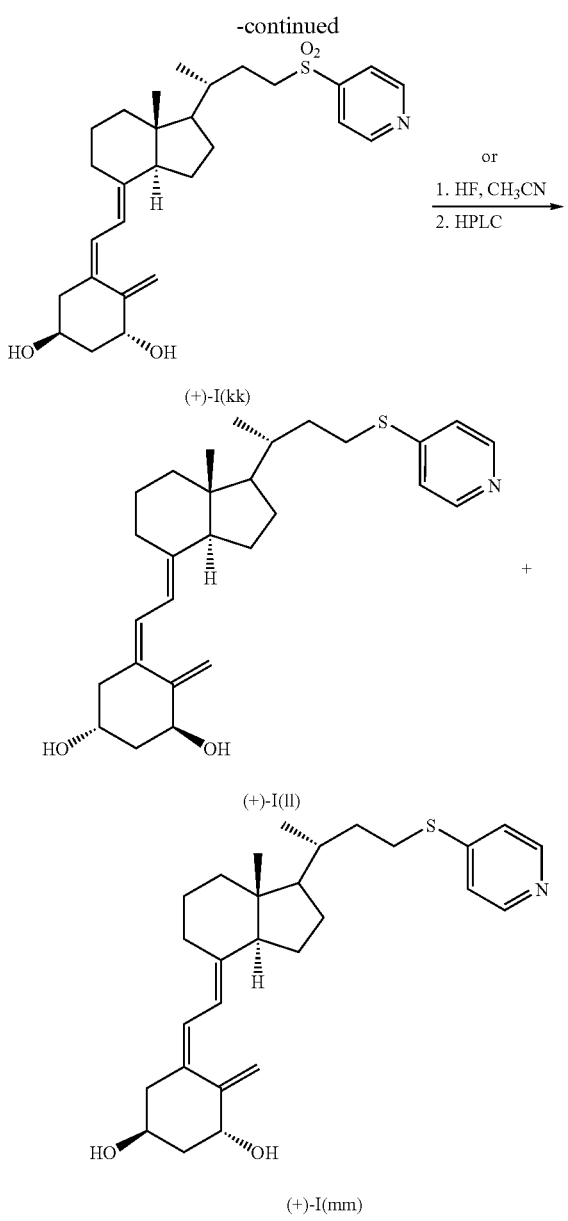

(+)-I(kk)

(+)-I(ll)

(+)-I(mm)

(a) 4-Pyridine Sulfide V: To a suspension of NaH (6.1 mg, 0.24 mmol) in 4 mL of DMF at 0 C), was added a solution of 4-mercaptopyridine IX (27 mg, 0.24 mmol) in 6 mL of DMF. After being stirred for 30 min at 0 C, a solution of iodide X (89.7 mg, 0.199 mmol) in 2 mL of THF was added via cannula. The resulting mixture was stirred for 2 h at room temperature, and then quenched with water. The mixture was extracted with EtOAc (3×15 mL). The combined organic layer was washed with water and brine, dried over $Na_2SO_4$, filtered, and concentrated in vacuo. Purification of the residue by flash column chromatography (50% EtOAc in hexanes) afforded 85.3 mg of sulfide V (0.197 mmol, 99% yield) as a colorless viscous oil. $[\alpha]_D^{25}$+69.6 (c 0.56, $CHCl_3$); $^1H$ δ 8.36 (d, J=6.4 Hz, 2H), 7.10 (dd, J=4.6 and 1.4 Hz, 2H), 3.99–3.98 (m, 1H), 3.03 (ddd, J=12.3, 10.3 and 4.7 Hz, 1H), 2.85 (ddd, J=12.3, 9.9 and 6.7 Hz, 1H), 1.95 (dt, J=12.4 and 2.8 Hz, 1H), 1.83–1.73 (m, 3H), 1.68–1.64 (m, 1H), 1.60–1.50 (m, 2H), 1.46–1.29 (m, 4H), 1.27–1.18 (m, 2H), 1.15–1.03 (m, 2H), 0.98 (d, J=6.4 Hz, 3H), 0.92 (s, 3H), 0.88 (s, 9H), 0.00 (s, 3H), -0.02 (s, 3H); $^{13}C$ δ 150.33, 148.63, 120.56, 69.29, 56.42, 52.97, 42.20, 40.63, 35.20, 34.40, 34.33, 28.06, 27.34, 25.77, 22.97, 18.39, 17.98, 17.59, 13.68, -4.82, -5.19; IR (neat, $cm^{-1}$) 2930, 2856, 1575, 1472, 1252, 1084, 1022, 837, 799, 774; HRMS m/z ([M+Na]$^+$) calcd 456.2727 for $C_{25}H_{43}NOSSiNa^+$, found 456.2709; ([M+H]$^+$) calcd 434.2907 for $C_{25}H_{44}NOSSi^+$, found 434.2921;.

(b) C,D-ring Ketone III: The sulfide V (54 mg, 0.124 mmol) in acetonitrile (4 mL) was treated with aqueous HF solution (48%, 20 μL, 0.57 mmol) and allowed to stir at rt for 2 h. The reaction mixture was quenched with saturated $NaHCO_3$ solution (5 mL), and was extracted with $CH_2Cl_2$ (10 mL×4). The organic layer was washed with water and brine, dried over sodium sulfate, filtered. Evaporation of solvent afforded 44.4 mg of the corresponding alcohol as a colorless viscous oil. A solution of this alcohol in $CH_2Cl_2$ (4 mL) was added PDC (94 mg, 0.25 mmol) and celite (100 mg). After being stirred for overnight at room temperature under argon atmosphere, the reaction mixture was diluted with EtOAc and filtered through a silica gel plug. The filtrate was concentrated in vacuo and then purified by column chromatography (50% EtOAc/petroleum ether) to give 21.2 mg of the C,D-ring ketone III (0.0668 mmol, 54% yield for two steps) as colorless viscous oil. $[\alpha]D^{23}$+29.4 (c 0.68, $CHCl_3$); $^1H$ δ 8.39 (d, J=4.4 Hz, 2H), 7.14 (d, J=5.6, 2H), 3.07 (ddd, J=12.3, 9.9 and 4.7 Hz, 1H), 2.89 (ddd, J=12.3, 9.5 and 6.7 Hz, 1H), 2.45 (dd, J=11.8 and 7.4 Hz, 1H), 2.32–2.18 (m, 2H), 2.15–2.10 (m, 1H), 2.06–1.98 (m, 1H), 1.97–1.69 (m, 4H), 1.64–1.44 (m, 5H), 1.36–1.25 (m, 1H), 1.06 (d, J=6.4 Hz, 3H), 0.66 (s, 3H); $^{13}C$ δ 211.57, 154.09, 145.86, 120.90, 61.78, 56.26, 49.81, 40.85, 38.86, 35.32, 34.05, 28.27, 27.56, 23.92, 19.03, 18.45, 12.47; IR (neat, $cm^{-1}$) 2956, 2928, 1709, 1575, 1481, 1112, 804; HRMS m/z ([M+Na]$^+$) calcd 340.1706 for $C_{19}H_{27}NOSNa^+$, found 340.1704; ([M+H]$^+$) calcd 318.1886 for $C_{19}H_{28}NOS+$, found 318.1875;.

(c) I(jj) and I(kk): Phosphine oxide (±)-IV and C,D-ring ketone III were separately azeotropically dried with benzene (4×4 mL) and held under vacuum (0.04 mm Hg) for 72 h immediately prior to use. To a solution of phosphine oxide IV (113.5 mg, 0.195 mmol) in THF (2 mL) at -78 C was added dropwise a 1.60 M solution of n-BuLi in hexanes (122 μL, 0.195 mmol) under argon atmosphere. The resulting deep red solution was allowed to stir for 20 min, at which time a pre-cooled (-78 C) solution of C,D-ring ketone III (18.8 mg, 0.059 mmol) in THF (2 mL) was transferred dropwise via cannula during a period of 5 min. The deep red solution was stirred in the dark for 6 h, during which time the color faded. Upon observation of a yellow color, the reaction mixture was quenched at -78 C with 3 mL of buffer water (pH=7.0). The mixture was allowed to warm to rt, extracted with EtOAc (10 mL×4), dried over $Na_2SO_4$, filtered, concentrated, and purified by silica gel column chromatography (50% EtOAc/petroleum ether) to give 34.9 mg of the coupled product (0.051 mmol, 86% yield). To a solution of this coupled product (15.6 mg, 0.0229 mmol) in 3 mL of MeOH, was added 2.0 mg of $Na_2WO_4.2H_2O$ (0.006 mmol) followed by $H_2O_2$ (50%, 13 μL, 0.23 mmol). The resulting mixture was stirred for 2 h at room temperature, and then quenched with the addition of saturated $Na_2SO_3$ aqueous solution The mixture was extracted with $CH_2Cl_2$ (3×15 mL). The combined organic layer was washed with water and brine, dried over $Na_2SO_4$, filtered, and concentrated in vacuo. Purification of the residue by flash column chromatography (6% MeOH in $CH_2Cl_2$) afforded 15.6 mg of sulfone (0.0218 mmol, 96% yield). The resulting sulfone was treated with aqueous HF solution (48%, 5 μL, 0.14 mmol). After being stirred for 2 h at rt in the dark, the reaction mixture was quenched with saturated $NaHCO_3$ solution (2 mL), and was extracted with $CH_2Cl_2$ (10 mL×4). The organic layer was washed with water and brine, dried over sodium sulfate, filtered, and concentrated in vacuo. Purification of the residue by flash column chromatography (10% MeOH in CH$_2$Cl$_2$) provided 10.3 mg of analogs I(jj) and I(kk) (0.0212 mmol, 97 yield). The diastereomers were isolated by HPLC [semi-preparative OJ chiral column, 20% iso-propanol/hexanes, 2.5 mL/min, 254 nm] to give 4.1 mg of (+)-I(jj) (t$_R$=83.6 min) and 1.7 mg of (+)-I(kk) (t$_R$=65.3 min). I(jj): [α]$_D^{24}$+28.0 (c 0.20, CHCl$_3$); $^1$H δ 8.93 (dd, J=4.4 and 1.6 Hz, 2H), 7.77 (dd, J=4.4 and 2.0 Hz, 2H), 6.36 (d, J=11.2 Hz, 1H), 6.00 (d, J=11.2 Hz, 1H), 5.33 (t, J=1.8 Hz, 1H), 4.99 (t, J=1.4 Hz, 1H), 4.45–4.41 (m, 1H), 4.26–4.20 (m, 1H), 3.20–3.12 (m, 1H), 3.06–3.00 (m, 1H), 2.82 (dd, J=12.4 and 4.0 Hz, 1H), 2.59 (dd, J=13.6 and 3.6 Hz, 1H), 2.31 (dd, J=13.2 and 6.8 Hz, 1H), 2.05–1.73 (m, 7H), 1.70–1.64 (m, 2H), 1.53–1.46 (m, 4H), 1.31–1.21 (m, 5H), 0.90 (d, J=6.4 Hz, 3H), 0.50 (s, 3H); $^{13}$C δ 150.77, 147.56, 142.34, 135.71, 133.29, 124.76, 121.48, 117.33, 111.87, 70.82, 66.82, 56.13, 55.63, 53.20, 45.84, 45.23, 42.82, 40.31, 35.07, 28.91, 27.99, 27.37, 23.40, 22.12, 18.45, 11.98; IR (neat, cm$^{-1}$) 3374, 2927, 2875, 1405, 1315, 1150, 755; UV (MeOH) λ$_{max}$ 265 nm (ε 8,997); HRMS m/z ([M+Na]$^+$) calcd 508.2492 for C$_{28}$H$_{39}$NO$_4$SNa$^+$, found 508.2522.

I(kk): [α]$_D^{24}$+6.7 (c 0.085, CHCl$_3$); $^1$H δ 8.93–8.92 (m, 2H), 7.77 (dd, J=4.4 and 1.6 Hz, 2H), 6.37 (d, J=11.6 Hz, 1H), 5.99 (d, J=11.2 Hz, 1H), 5.31 (m, 1H), 4.99 (m, 1H), 4.43 (m, 1H), 4.22 (m, 1H), 3.20–3.12 (m, 1H), 3.06–3.00 (m, 1H), 2.84–2.79 (m, 1H), 2.63–2.58 (m, 1H), 2.35–2.27 (m, 1H), 2.00–1.76 (m, 7H), 1.70–1.46 (m, 6H), 1.30–1.20 (m, 5H), 0.90 (d, J=6.4 Hz, 3H), 0.51 (s, 3H); $^{13}$C δ 147.26, 147.21, 142.40, 140.20, 133.16, 124.76, 117.32, 112.53, 71.29, 66.80, 56.13, 55.64, 53.18, 45.85, 45.44, 42.80, 40.29, 35.07, 29.70, 28.90, 28.00, 27.35, 23.39, 22.15, 18.45; IR (neat, cm$^{-1}$) 3354, 2924, 2854, 1456, 1315, 1150, 756; UV (MeOH) λ$_{max}$ 265 nm (ε 5,542); HRMS m/z ([M+Na]$^+$) calcd 508.2492 for C$_{28}$H$_{39}$NO$_4$SNa$^+$, found 508.2533.

(d) I(ll) and I(mm): In a like manner, compounds I(ll) and I(mm) may be prepared by deprotecting the coupled product obtained as above by reacting compound III with compound (+/–)-IV, followed by deprotection of the C1 and C3 hydroxy groups using HF in CH$_3$CN, followed by separation of the diastereomers using HPLC as described in part (c).

Example 21

Preparation of Compounds I(nn) and I(oo)

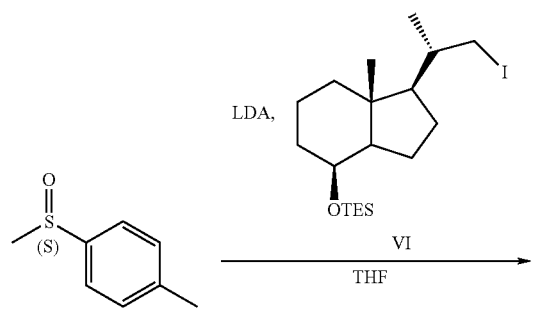

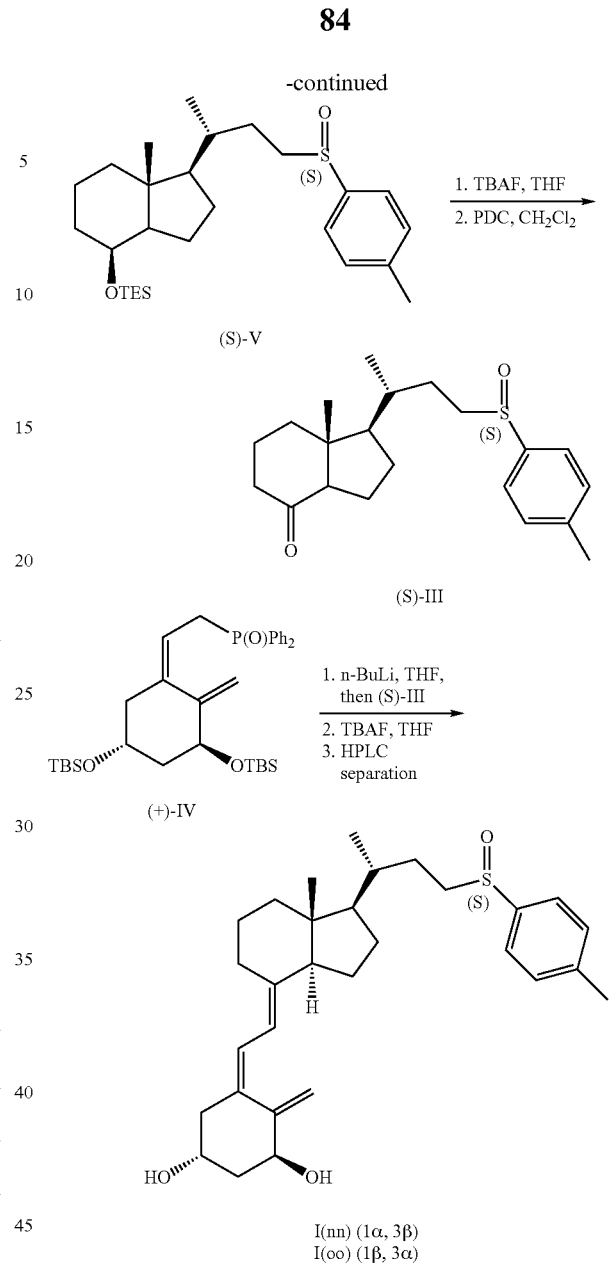

Reagents and Materials. (S)-(–)-methyl p-tolyl sulfoxide (S)-VII (R$^4$=pCH$_3$Ph, x 1, R$^5$, R$^6$=H) was purchased from Aldrich (99% ee /HPLC, [α]$^{20}_D$ –145 (c 2.0 CH$_3$COCH$_3$)).

(a) 24(S)-SO-pTol Silyl Ether (S)-V. To a solution of diisopropylamine (0.77 mL, 0.47 mmol) in THF (1 mL) was added 0.42 mL of nBuLi (1.33 M in hexanes, 0.47 mmol) at –78° C. After 30 min stirring, a precooled (–78° C.) solution of (S)-(–)-methyl p-tolyl sulfoxide (S)-VII (85.4 mg, 0.55 mmol) in THF (2 mL) was added at –78° C. After 30 min stirring, a precooled (–78° C.) solution of iodide VI (70.0 mg, 0.16 mmol) in THF (2 mL) was added at –78° C. via cannula. The mixture was slowly warmed to room temperature after 15 min and allowed to stir overnight. Water (5 mL) was added and the reaction solution was extracted with EtOAc (3×20 mL), washed with brine, dried over MgSO$_4$, concentrated in vacuo, and then purified by column chromatography (25% EtOAc/hexanes) to give 61.8 mg (83%) of 24(S)-SO-pTol Silyl Ether (S)-III as a colorless oil: [α]$^{24}_D$ –26.7 (c 3.09, CHCl$_3$); $^1$H NMR (400 MHz, CDCl$_3$)

δ 7.50 (d, J=8.4 Hz, 2H), 7.31 (d, J=8.4 Hz, 2H), 3.99 (d, J=2.4 Hz, 1H), 2.84–2.77 (m, 1H), 2.73–2.66 (m, 1H), 2.40 (s, 3H), 1.90–1.86 (m, 1H), 1.80–1.62 (m, 4H), 1.56–1.43 (m, 2H), 1.38–1.26 (m, 4H), 1.19–1.14 (m, 2H), 1.08–0.98 (m, 2H), 0.92 (t, J=8.0 Hz, 9H), 0.86 (d, J=6.4 Hz, 3H), 0.85 (s, 3H), 0.53 (q, J=8.0 Hz, 6H); $^{13}$C NMR (100 MHz, CDCl$_3$) δ 141.33, 140.74, 129.79, 124.16, 69.20, 56.16, 54.47, 52.92, 42.11, 40.62, 34.73, 34.49, 27.95, 27.03, 22.85, 21.38, 18.41, 17.57, 13.44. 6.90, 4.86; IR (neat, cm$^{-1}$) 2943, 2872, 1496, 1454, 1413, 1372, 1231, 1161, 1090, 1020, 808, 738, 720; HRMS m/z (M+Na) calcd 485.2879 for C$_{27}$H$_{46}$O$_2$SSiNa$^+$, found 485.2863.

(b) 24(S)-SO-pTol C, D ring ketone (S)-III. To a solution of silyl ether (S)-V (60.0 mg, 0.13 mmol) in THF (10.0 mL) was added 0.39 mL (0.39 mmol) of a 1.0 M solution of TBAF in THF, and then it was stirred at 0° C. for 1 h and stirred overnight at room temperature. The reaction mixture was quenched with water (5 mL), extracted with EtOAc (30 mL×2), washed with brine, dried over MgSO$_4$, concentrated in vacuo, and then purified by column chromatography (30% EtOAc/hexanes) to give 45.2 mg (100%) of alcohol as a colorless oil.

To a solution of the C,D-ring alcohol (45.2 mg, 0.13 mmol) in CH$_2$Cl$_2$ (15 mL) was added 150 mg of oven-dried Celite and PDC (146.3 mg, 0.39 mmol) at room temperature. The reaction mixture was stirred overnight and then passed through a 2 cm pad of flash silica gel and washed with EtOAc. The filtrate was concentrated and purified by column chromatography (67% EtOAc/hexanes) to give 42.0 mg (93%) of the desired C,D-ring ketone (S)-III as a colorless oil: [α]$^{23}_D$ −57.17 (c 2.41, CHCl$_3$); $^1$H NMR (400 MHz, CDCl$_3$) δ 7.47 (d, J=8.4 Hz, 2H), 7.29 (d, J=8.4 Hz, 2H), 2.80 (dt, J=12.8, 5.2 Hz, 1H), 2.68 (dt, J=12.8, 5.2 Hz, 1H), 2.40–2.36 (m, 1H), 2.38 (s, 3H), 2.26–2.12 (m, 2H), 2.04–1.93 (m, 2H), 1.90–1.80 (m, 1H), 1.78–1.62 (m, 3H), 1.55–1.33 (m, 5H), 1.26–1.16 (m, 1H), 0.91 (d, J=6.4 Hz, 3H), 0.56 (s, 3H); $^{13}$C NMR (100 MHz, CDCl$_3$) δ 211.60, 141.40, 140.43, 129.79, 124.03, 61.64, 55.97, 54.11, 49.68, 40.75, 38.70, 34.87, 27.72, 27.15, 23.83, 21.32, 18.87, 18.44, 12.34; IR (neat, cm$^{-1}$) 2954, 2860, 1701, 1490, 1460, 1448, 1225, 1084, 1037, 808, 755, 508; HRMS m/z (M+Na) calcd 369.1859 for C$_{21}$H$_{30}$O$_2$SSiNa$^+$, found 369.1861.

(c) 24(S)-SO-pTol analogues I(nn) and I(oo). A solution of 62.0 mg (0.11 mmol) of racemic phosphine oxide IV in 2.0 mL of anhydrous THF was cooled to −78° C. and treated with 79.9 μL (0.11 mmol, 1.33 M in hexanes) of n-BuLi under argon atmosphere. The mixture turned reddish orange and was stirred for 15 min at −78° C. To the solution was added dropwise a solution of 34.0 mg (0.09 mmol) of the C,D-ring ketone (S)-III in 1.0 mL of anhydrous THF. The reaction kept going until the reddish orange color faded to yellow (about 6 h). The reaction was quenched by adding 3.0 mL of pH 7 buffer, then warmed to room temperature, extracted with EtOAc (20 mL×2), washed with brine, dried over MgSO$_4$, concentrated in vacuo, and then purified by column chromatography (25%→50% EtOAc/hexanes) to afford 47.2 mg (68%) of the coupled product as a colorless oil.

The coupled product (45.0 mg, 0.063 mmol) was dissolved in 10 mL of anhydrous THF, and to this solution was added 0.25 mL (0.25 mmol) of a 1.0 M solution of TBAF in THF. The reaction was run in darkness overnight, then extracted with EtOAc (30 mL×2), washed with brine, dried over MgSO$_4$, concentrated in vacuo, and then purified by column chromatography (EtOAc only) to give 29.9 mg (98%) of a mixture of two diastereomers as a colorless oil. The diastereomers were separated by chiral HPLC (OD semipreparative column, 12% 2-Propanol/Hexanes, 2.5 mL/min) to afford 13.5 mg (45%) of I(nn) (1α,3β, t$_R$ 63 min) and 4.8 mg (16%) of I(oo) (1β,3α, t$_R$ 76 min) as colorless oils. I(nn): [α]$^{24}_D$ −25.84 (c 0.66, CHCl$_3$); $^1$H NMR (300 MHz, CDCl$_3$) δ 7.51 (d, J=8.0 Hz, 2H), 7.32 (d, J=8.0 Hz, 2H), 6.35 (d, J=11.2 Hz, 1H), 6.00 (d, J=11.2 Hz, 1H), 5.32 (s, 1H), 4.98 (s, 1H), 4.44–4.40 (m, 1H), 4.25–4.18 (m, 1H), 2.88–2.66 (m, 4H), 2.57 (dd, J=13.2, 3.2 Hz, 1H), 2.41 (s, 3H), 2.30 (dd, J=13.2, 6.4 Hz, 1H), 2.05–1.63 (m, 10H), 1.53–1.34 (m, 4H), 1.30–1.15 (m, 3H), 0.91 (d, J=6.4 Hz, 3H), 0.50 (s, 3H); IR (neat, cm$^{-1}$) 3377, 2931, 2860, 1642, 1590, 1443, 1373, 1296, 1025, 1008, 908, 808, 749, 626; UV (MeOH) λ$_{max}$ 242 nm (ε11490). I(oo): [α]$^{25}_D$ −26.43 (c 0.23, CHCl$_3$); $^1$H NMR (300 MHz, CDCl$_3$) δ 7.51 (d, J=8.0 Hz, 2H), 7.32 (d, J=8.0 Hz, 2H), 6.37 (d, J=11.2 Hz, 1H), 5.99 (d, J=11.2 Hz, 1H), 5.31 (s, 1H), 4.99 (s, 1H), 4.45–4.41 (m, 1H), 4.25–4.17 (m, 1H), 2.88–2.66 (m, 4H), 2.60 (dd, J=13.2, 3.6 Hz, 1H), 2.42 (s, 3H), 2.34–2.25 (m, 1H), 2.00–1.88 (m, 3H), 1.80–1.62 (m, 3H), 1.51–1.44 (m, 3H), 1.29–1.19 (m, 4H), 0.91 (d, J=6.3 Hz, 3H), 0.50 (s, 3H); IR (neat, cm$^{-1}$) 3377, 2931, 2860, 1660, 1642, 1595, 1443, 1372, 1296, 1084, 1025, 955, 808, 749, 626; UV (MeOH) λ$_{max}$ 242 nm (ε 12445).

Example 22

Preparation of Compounds I(pp) and I(qq)

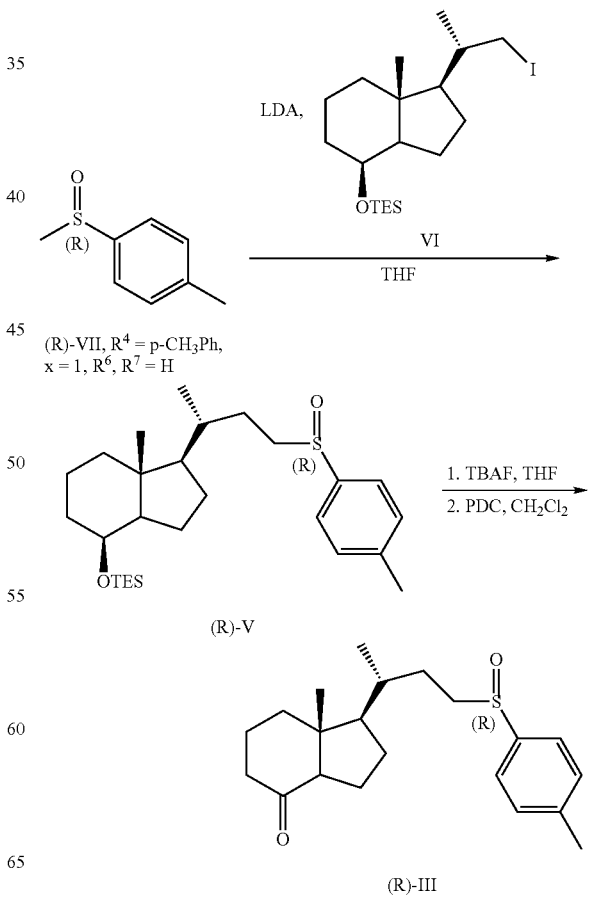

-continued

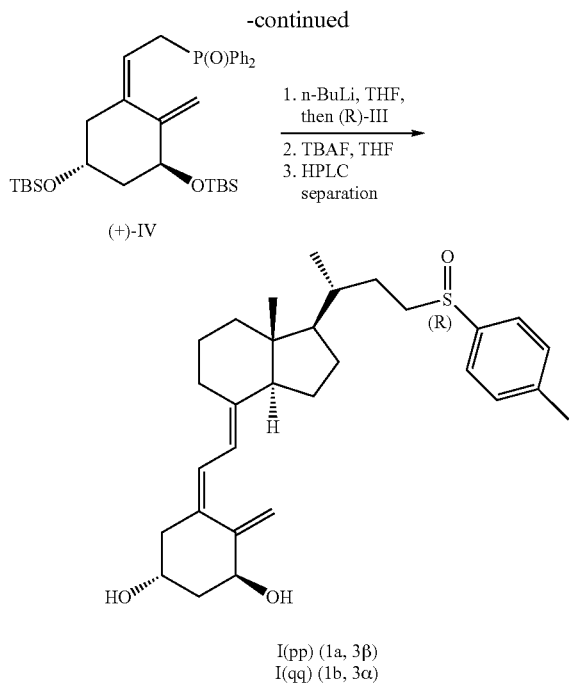

I(pp) (1α, 3β)
I(qq) (1β, 3α)

Reagents and Materials. (R)-VII (R$^4$=pCH$_3$Ph, x=1, R$^5$, R$^6$=H) was purchased from Aldrich (99% ee /HPLC, [α]$^{20}_D$ +145 (c 2.0, CH$_3$COCH$_3$))

(a) 24(R)-SO-pTol Silyl Ether (R)-V. To a solution of diisopropylamine (0.76 mL, 0.47 mmol) in THF (1 mL) was added 0.41 mL of nBuLi (1.33 M in hexanes, 0.47 mmol) at −78° C. After 30 min stirring, a precooled (−78° C.) solution of (R)-(+)-methylp-tolyl sulfoxide (R)-VII (85.0 mg, 0.55 mmol) in THF (2 mL) was added at −78 ° C. After 30 min stirring, a precooled (−78° C.) solution of iodide VI (70.0 mg, 0.16 mmol) in THF (2 mL) was added at −78° C. via cannula. The mixture was slowly warmed to room temperature after 15 min and allowed to stir overnight. Water (5 mL) was added and the reaction solution was extracted with EtOAc (3×20 mL), washed with brine, dried over MgSO$_4$, concentrated in vacuo, and then purified by column chromatography (30% EtOAc/hexanes) to give 56.7 mg (76%) of 24(R)-SO-pTol Silyl Ether (R)-V as a colorless oil: [α]$^{24}_D$ +127.61 (c 2.70, CHCl$_3$); $^1$H NMR (400 MHz, CDCl$_3$) δ 7.49 (d, J=8.4 Hz, 2H), 7.31 (d, J=8.4 Hz, 2H), 4.00 (d, J=2.4 Hz, 1H), 2.81–2.74 (m, 1H), 2.71–2.64 (m, 1H), 2.40 (s, 3H), 1.90–1.86 (m, 1H), 1.83–1.68 (m, 3H), 1.67–1.62 (m, 1H), 1.57–1.47 (m, 2H), 1.39–1.27 (m, 4H), 1.24–1.14 (m, 2H), 1.08–0.95 (m, 2H), 0.92 (t, J=8.0 Hz, 9H), 0.86 (s, 3H) 0.85 (d, J=6.0 Hz, 3H), 0.53 (q, J=8.0 Hz, 6H); $^{13}$C NMR (100 MHz, CDCl$_3$) δ 141.18, 140.81, 129.77, 124.00, 69.20, 56.14, 54.51, 52.92, 42.10, 40.62, 34.56, 34.49, 27.76, 27.09, 22.85, 21.36, 18.33, 17.57, 13.45. 6.90, 4.86; IR (neat, cm$^{-1}$) 2949, 2875, 1457, 1412, 1375, 1236, 1164, 1088, 1069, 1048, 1034, 1017, 972, 948, 846, 808, 740, 724, 509; HRMS m/z (M+Na) calcd 485.2879 for C$_{27}$H$_{46}$O$_2$SSiNa$^+$, found 485.2893.

(b) 24(R)-SO-pTol C, D ring ketone (R)-III. To a solution of silyl ether (R)-V (52.0 mg, 0.11 mmol) in THF (10.0 mL) was added 0.34 mL (0.34 mmol) of a 1.0 M solution of TBAF in THF, and then it was stirred at 0° C. for 1 h and stirred overnight at room temperature. The reaction mixture was quenched with water (5 mL), extracted with EtOAc (30 mL×2), washed with brine, dried over MgSO$_4$, concentrated in vacuo, and then purified by column chromatography (30% EtOAc/hexanes) to give 39.2 mg (100%) of alcohol as a colorless oil.

To a solution of the C,D-ring alcohol (39.2 mg, 0.11 mmol) in CH$_2$Cl$_2$ (15 mL) was added 126 mg of oven-dried Celite and PDC (126.8 mg, 0.33 mmol) at room temperature. The reaction mixture was stirred overnight and then passed through a 2 cm pad of flash silica gel and washed with EtOAc. The filtrate was concentrated and purified by column chromatography (67% EtOAc/hexanes) to give 40.5 mg (96%) of the desired C,D-ring ketone (R)-III as a colorless oil: [α]$^{24}_D$ +117.42 (c 2.02, CHCl$_3$); $^1$H NMR (400 MHz, CDCl$_3$) δ 7.47 (d, J=8.0 Hz, 2H), 7.29 (d, J=8.4 Hz, 2H), 2.80–2.64 (m, 2H), 2.42–2.37 (m, 1H), 2.39 (s, 3H), 2.27–2.13 (m, 2H), 2.05–1.93 (m, 2H), 1.90–1.78 (m, 3H), 1.74–1.63 (m, 1H), 1.56–1.45 (m, 3H), 1.42–1.33 (m, 2H), 1.30–1.21 (m, 1H), 0.91 (d, J=6.8 Hz, 3H), 0.58 (s, 3H); $^{13}$C NMR (100 MHz, CDCl$_3$) δ 211.60, 141.28, 140.55, 129.79, 123.92, 61.69, 56.05, 54.26, 49.70, 40.78, 38.75, 34.72, 27.64, 27.24, 23.86, 21.31, 18.91, 18.39, 12.39; IR (neat, cm$^{-1}$) 2954, 2872, 1707, 1490, 1458, 1372, 1302, 1219, 1084, 1037, 1014, 937, 808, 749, 487; HRMS m/z (M+Na) calcd 369.1859 for C$_{21}$H$_{30}$O$_2$SSiNa$^+$, found 369.1864.

(c) 24(R)-SO-pTol analogues I(pp) and I(qq). A solution of 62.0 mg (0.11 mmol) of racemic phosphine oxide IV in 2.0 mL of anhydrous THF was cooled to −78° C. and treated with 66.5 µL (0.11 mmol, 1.60 M in hexanes) of n-BuLi under argon atmosphere. The mixture turned reddish orange and was stirred for 15 min at −78° C. To the solution was added dropwise a solution of 30.0 mg (0.087 mmol) of the C,D-ring ketone (R)-III in 1.0 mL of anhydrous THF. The reaction kept going until the reddish orange color faded to yellow (about 3 h). The reaction was quenched by adding 3.0 mL of pH 7 buffer, then warmed to room temperature, extracted with EtOAc (20 mL×2), washed with brine, dried over MgSO$_4$, concentrated in vacuo, and then purified by column chromatography (25%→50% EtOAc/hexanes) to afford 43.0 mg (70%) of the coupled product as a colorless oil.

The coupled product (43.0 mg, 0.060 mmol) was dissolved in 10 mL of anhydrous THF, and to this solution was added 0.24 mL (0.24 mmol) of a 1.0 M solution of TBAF in THF. The reaction was run in darkness overnight, then extracted with EtOAc (30 mL×2), washed with brine, dried over MgSO$_4$, concentrated in vacuo, and then purified by column chromatography (EtOAc only) to give 28.0 mg (96%) of a mixture of two. diastereomers as a colorless oil. The diastereomers were separated by chiral HPLC (OD semipreparative column, 10% 2-Propanol/Hexanes, 2.5 mL/min) to afford 8.2 mg (34%) of I(pp) (1α,3β, t$_R$ 89 min) and 5.4 mg (23%) of I(qq) (1β,3α, t$_R$ 117 min) as colorless oils. I(pp): [α]$^{24}_D$ +18.97 (c 0.41, CHCl$_3$); $^1$H NMR (300 MHz, CDCl$_3$) δ 7.50 (d, J=8.0 Hz, 2H), 7.32 (d, J=8.0 Hz, 2H), 6.36 (d, J=11.2 Hz, 1H), 6.00 (d, J=11.2 Hz, 1H), 5.32 (s, 1H), 4.99 (s, 1H), 4.45–4.41 (m, 1H), 4.25–4.20 (m, 1H), 2.85–2.70 (m, 4H), 2.57 (m, 1H), 2.42 (s, 3H), 2.30 (m, 1H), 2.01–1.62 (m, 10H), 1.57–1.35 (m, 4H), 1.33–1.20 (m, 3H), 0.91 (d, J=6.5 Hz, 3H), 0.52 (s, 3H); IR (neat, cm$^{-1}$) 3377, 2931, 2860, 1713, 1654, 1596, 1443, 1378, 1255, 1213, 1084, 1020, 1008, 808, 749, 655; UV (MeOH) λ$_{max}$ 242 nm (ε3226). I(qq): [α]$^{24}_D$ +9.27 (c 0.27, CHCl$_3$); $^1$H NMR (300 MHz, CDCl$_3$) δ 7.51 (d, J=8.0 Hz, 2H), 7.32 (d, J=8.0 Hz, 2H), 6.38 (d, J=11.2 Hz, 1H), 5.99 (d, J=11.2 Hz, 1H), 5.31 (s, 1H), 4.99 (s, 1H), 4.44 (m, 1H), 4.22–4.18 (m, 1H), 2.88–2.65 (m, 4H), 2.61 (dd, J=13.2, 3.6 Hz, 1H), 2.41 (s, 3H), 2.34–2.23 (m, 1H), 2.00–1.60 (m, 6H), 1.56–1.42 (m, 3H), 1.28–1.15 (m, 4H), 0.89 (d, J=6.2 Hz, 3H), 0.52 (s, 3H); IR (neat, cm$^{-1}$) 3365, 2919, 2848, 1719, 1660, 1454, 1378, 1255, 1213, 1084, 1025, 803, 755; UV (MeOH) $\lambda_{max}$ 238 nm ($\epsilon$1,813).

Example 23

CYP24 Enzyme Assay (Induced HPK1A-ras Cells)

(i) Material and reagents:

1,25(OH)$_2$D$_3$ 10$^{-5}$ M (Sigma, St. Louis, Mo.);
Preparation of 10$^{-5}$ M working solution is as follows:
Dissolve 1 mg of 1,25(OH)$_2$D$_3$ into 480 μl of isopropanol to make 5×10$^{-3}$ M stock solution. Store at −70° C. until needed. Aliquot 1 μl of 1,25(OH)$_2$D$_3$ 5×10$^{-3}$ M stock solution to 499 μl of isopropanol to make 1,25(OH)$_2$D$_3$ 10$^{-5}$ working solution. Store at −20° C. until needed.

[$^3$H]-1,25(OH)$_2$D$_3$ 16,000 cpm/μL, 8 μM (Perkin Elmer, Boston, Mass.) HPK1A-ras cells (obtained from Dr. Glenville Jones, Queens University, Kingston, Ontario, Canada)
48-well plate
Methanol
Dichloromethane
Saturated KCl:KCl 30 g, H$_2$O 400 ml
1,2-Dianilinoethane (DPPD)
Ketoconazole (Sigma, St. Louis, Mo.)

(ii) Procedure:
1. Induction of HPK1A-ras cells (The day before assay)
When the HPK1A-ras cells were 80–90% confluent, added 1 μL 10$^{-5}$ M
1,25(OH)$_2$D$_3$ to 1 mL medium in the plate (final concentration is 10$^{-8}$ M).
2. Preparation of cell suspension
After 18 to 20 hours induction, removed the medium and washed the cell twice with PBS. Then tripsinized the cells from plate, centrifuged (2,000 rpm, 5 min) and suspended cells pellet in DMEM medium+1% BSA. Counted the cells and adjusted cells density to 250,000/150 μL, added 150 μL cell suspension to each well in 48-well plate (including 3 wells as a no cell control, and 3 well cells without drug or inhibitor as controls).
3. Added 25 μL ketoconazole (final concentration 10$^{-5}$ M, 10$^{-6}$M, 10$^{-7}$M, 10$^{-8}$M) or drugs (final concentration 10$^{-6}$M, 10$^{-7}$M, 10$^{-8}$M, 10$^{-9}$M) into each designated well. Kept the plate in 37° C. for 10 min.
4. Preparation of substrate
For each ml required, added 972 μl of DMEM+1%BSA medium, 20 μl of $^3$H-1,25(OH)$_2$D$_3$, and 8 μl of 100 nM DPPD to a tube and vortexed.
5. Incubation
Added 25 μL substrate to each well, incubated the plate at 37° C. for 2 hour.
Added 25 μL substrate to counting plate (2 well) as a total count.
6. Lipid extraction and counting
Added 500 μL methanol to each well to stop the reaction, transfered them to tube.
Added 250 μL dichloromethane and vortex.
Added 250 μL dichloromethane and 250 μL saturated KCl, and vortex.
Centrifuged at 4000 rpm for 5 min.
Transferred 100 μL of aqueous phase (upper phase) to counting plastic counting plate. Added 600 μL of scintillation fluid to each well. Counted the plate in scintillation counter.

7. Calculation enzyme activity
CPM of cell control after subtraction of CPM of non-cell control (NCC) was as 100% enzyme activity. Enzyme activity=(CPM in test compounds well−CPM in NCC well)/(CPM in Cell control−CPM in NCC well)*100%

| | Dilution of Ketoconazole Stock 10$^{-2}$ M | | |
|---|---|---|---|
| Concentration (final) | From previous step (μL) | DMEM + 1% BSA (μL) | Concentration (actual) |
| 10$^{-5}$ M | 4 | 496 | 8 × 10$^{-5}$ M |
| 10$^{-6}$ M | 12.5 | 112.5 | 8 × 10$^{-6}$ M |
| 10$^{-7}$ M | 12.5 | 112.5 | 8 × 10$^{-7}$ M |
| 10$^{-8}$ M | 12.5 | 112.5 | 8 × 10$^{-8}$ M |

| | Dilution of test compounds Stock 10$^{-3}$ M | | |
|---|---|---|---|
| Concentration (final) | From previous step (μL) | DMEM + 1% BSA (μL) | Concentration (actual) |
| 10$^{-6}$ M | 4 | 496 | 8 × 10$^{-6}$ M |
| 10$^{-7}$ M | 12.5 | 112.5 | 8 × 10$^{-7}$ M |
| 10$^{-8}$ M | 12.5 | 112.5 | 8 × 10$^{-8}$ M |
| 10$^{-9}$ M | 12.5 | 112.5 | 8 × 10$^{-9}$ M |

(iii) Results are shown in Table 1 and, for compound I(a), in FIG. 1A.

(iv) References:
Ray S, Ray R, Holick M. Metabolism of $^3$H-1alpha, 25-dihydroxy vitamin D$_3$ in the cultured human keratinocytes (1995) 59:117–122

Dilworth F J, Scott I, Green A, Strugnell S, Guo Y D, Roberts E A, Kremer R, Calverley, M J, Makin H L J, Jones G. Different mechanisms of hydroxylation site selection by liver and kidney cytochrome P450 species (CYP27 and CYP24) involved in Vitamin D metabolism. (1995) J Biochem 270(28):16766–16774.

Example 24

CYP24 Enzyme Assay (Using Stable Cell Line—V79-CYP24 cells)

(i) Material and reagents
1α,25(OH)$_2$D$_3$ 1 mM reconstituted in isopropanol
Substrates (1 mM) reconstituted in isopropanol
V79-CYP24 cells
DMEM media supplemented with hygromycin and 10% fetal bovine serum
DMEM+1% BSA media
DPPD
48-well plate
methanol
dichloromethane
saturated KCl: KCl 30g, H$_2$0 400 ml
ketoconazole (ii) Procedure:
1. Preparation of cell suspension On the day of the assay, washed the monolayer of V79-CYP24 cells once with 1×PBS buffer and then trypsinize for 5 min at room temperature (approx. 22° C.). Added 1×PBS. Collected cells into tube, centrifuged cells (500×g, 5 min) and resuspended in DMEM+1% BSA media. Counted cells and adjusted density to 250,000 cells/150 µl (1.67 million/1 mL).

2. Cell plating

Added 150 µl of cell suspension to appropriately labelled wells of a 48-well plate. Incubated plate for 30 minutes at 37° C. in a humidified atmosphere containing 5% $CO_2$ for adherence of cells to wells.

3. Compound addition

Added 25 µl of inhibitor ($10^{-6}$ to $10^{-9}$ M) and then after 10 min added 25 µl of substrate [$^3$H-1β]-1α,25$(OH)_2D_3$ (20 nM) for 2 hours at 37° C. in a humidified atmosphere containing 5% $CO_2$. Both inhibitor and substrate were prepared in. DMEM with 1% BSA media in the absence and presence of 100 µM DPPD.

4. Lipid extraction and counting

Added 500 µl of methanol to stop the reaction. Transferred to tube. Added 250 µl of dichloromethane and vortexed. Added 250 µl of dichloromethane and 250 µl of saturated KCL and vortexed. Centrifuged at 4000 rpm for 5 min. Triplicate 100 µl aliquots of aqueous fraction were mixed with 600 µl of scintillation fluid and the radioactivity was measured using a scintillation counter. All values were normalized for background.

(iii) Results.

Shown in Table 1

(iv) Reference.

1. PCT Patent Application Serial No. PCT/CA03/00620

Example 25

CYP27A1 Enzyme Assay (A) Procedure:

As described in:

Dilworth F J, Black S M, Guo Y D, Miller W L, Jones G. Construction of a P450c27 fusion enzyme: a useful tool for analysis of vitamin $D_3$ 25-hydroxylase (1996) Biochem J 320:267–271

Sawada N, Sakaki T, Ohta M, Inouye K. Metabolism of vitamin D (3) by human CYP27A1 (2000) Biochem Biophys Res Commun 273(3):977–84

(B) Results:

See Table 1 and (for compound I(a)) FIG. 1C.

Example 26

Assay of CYP1-alpha hydroxylase (CYP27B1) Using Transfected COS-1 Cells (A) Transit transfection (i) Reagent and material 1. COS-1 cells (50–80% confluent)
2. FuGene 6 Transfection Reagent
3. PcDNA vector containing CYP-1 alpha hydroxylase cDNA(1 µg/µl)
4. DMEM Medium+10% FCS
5. DMEM Medium (serum-free)
6. 6-well plate (ii) Transfection cocktail preparation (The amount depends on how many wells transfected)

1. To a sterile tube, add serum-free medium (100 µl per well), Then add FuGene 6 Reagent (3 µl per well). Tap gently to mix. Pay attention to the order. Add FuGene 6 Reagent directly to medium, do not allow undiluted Fugene 6 Reagent to come in contact with plastic surfaces other than the pipette tip.
2. Add DNA solution (1 µg per well) to the prediluted FuGene 6 Reagent from step 2
3. Gently tap the tube to mix the contents. Do not vortex. Incubate for 15 min at room temperature (no more than 45 min).

(iii) Cells preparation

1. Trypsinize Cos-1 cells, centrifuge cell suspension, suspend1 cells pellet in DMEM medium+10% FCS.
2. Dilute the cells suspension to 750,000 cell/ml (75cell/square), (iv) Transfection 1. Add 1.7 ml DMEM medium+I0%FCS to each well of 6 well plate.
2. Transfer the correct volume of the cell suspension (200 µl/well) to the transfection cocktail. Mix them gently
3. Add 0.3 ml of the mixture to each well. Make sure that the same amount cells are added to each well. Swirl the wells to ensure even dispersal.
4. Incubate the cells for 24 hours at 37 C, 5% $CO_2$ until enzyme activity assay.

(B) Enzyme Activity Assay (i) Reagent and material

DMEM medium+1% BSA

PBS

[$^3$H-26,27]-25(OH)$D_3$

DPPD 100 mM (ii) Procedure

1. Wash cells once with PBS. Be careful, don't disturb the attached cells.
2. Add 0.55 ml medium (DMEM+1%BSA) each well.
3. Add 0.025 ml medium containing test compounds
4. Incubate the cells for 10 minutes
5. Add 0.025ml medium containing [3H-26,27]-25(OH)$D_3$ (50,000 CPM) and DPPD (0.6 µl stock)
6. Incubate the cells for 2 hour.
7. Add 1.5 ml Methanol to stop reaction
8. Add internal standard.
9. Transfer the medium to labeled tube.
10. Add 0.75 ml dichloromethane, vortex and keep in room temperature for 15 minutes.
11. Add 0.75 ml dichloromethane and 0.75 ml saturated KCl
12. Vortex and centrifuge
13. Remove upper phase and dry the lower phase in Speed-Vac
14. Add 110 µl mobile phase, vortex and centrifuge for 5 min.
15. Transfer 105 µl to the insert in HPLC vial.
16. HPLC analysis conditions:

Solvent: Hexane/isopropanol/methanol (91/7/2)

Column: SIL 3 µm column

Flow rate: 2 ml/min

Detector: UV detector and radioactive detector.

(C) Results

See FIG. 1B for Compound I(a) and see Table 1.

(D) References

Shink T, Shimada H, Wakino S, Anazawa H, Hayashi M, Saruta T, Deluca H, Suda T. Cloning and expression of rat 25-hydroxyvitamin $D_3$-1-alpha -hydroxylase cDNA. (1997) Pro. Natl Acad Sci 94:12920–12925

Muralidharan K R, Rowland-goldsmith M, Lee S A, Park G, Norman A W, Henry H L, Okamura W H. Inhibitors of 25-hydroxyvitamin $D_3$-1alpha-hydroxylase: Thiavitamin D analogues and biological evaluation. (1997) J Steroid Biochem. Molec. Biol. 62(1):73–78.

Example 27

Assay of CYP1-alpha hydroxylase (CYP27B1) Using Human Epidermal Kertinocytes

Compound I(a) was assayed in vitro for CYP1-alpha hydroxylase activity in human epidermal kertinocytes using a standard protocol (Schuster, I. et al. Steroids 2001, 66, 409–422). See Table 1 for results.

Example 28

VDR Bindin2 Assay (i) Reagent and materials
1. VDR 9.4 pmol/μl (human, recombinant, Biomol).
2. $[^3H]$-I,25$(OH)_2D_3$ in ethanol
3. 1,25$(OH)_2D_3$ in ethanol
4. $TEK_{300}$

| Tris-HCl | 50 mM |
| EDTA | 1.5 mM |
| KCl | 300 mM |

Adjust pH to 7.4 (25 C)
5. $TEDK_{300}$
$TEK_{300}$
DTT (dithreitol) 10 mM (MW 154.24)
6. Tris buffer
22.50 g Tris-HCl
500 ml $H_2O$
13.25 g Tris-base
500 ml $H_2O$
Kept in 4 C
7. Dextran-T70 (Mol 70,000) Pharmacia
8. Charcoal (carbon decolorizing neutral, norit) Fisher Scientific
9. Gelatin (G-2625 Sigma)

(ii) Reagent Preparation
1. Charcoal dextran solution
(1) Tris buffer
    Mixed equal amount of Tris-HCl and Tris-base.
(2)

| Norit decolorizing neutral charcoal | 2.0 g |
| Tris buffer | 150 mL |

Stirred
(3) Dextran T-70 0.2 g
Tris buffer 50 ml.

(4) Slowly driped the suspended dextran into charcoal solution with stirring.
Kept in refrigerater overnight.
Thirty minutes before use, stored on ice with continuous mixing.
2. $TEK_{300}$/Gelatin solution
50 mg swine gelatin
5 ml $TEDK_{300}$ solution
heated, stirred then cooled to 4 C.
5 ml $TEDK_{300}$ solution
3. Preparation of 1,25$(OH)_2D_3$ and test compounds in ethanol
1,25$(OH)_2D_3$: 125, 250, 500, 1000, 2000, 4000 pg/25 μl. (stock 10–5 M/25μL=100,000 pg/25μL)

| Concentration (ng/mL) | Amount (pg/50 μL) |
| --- | --- |
| 5.0 | 125 |
| 10.0 | 250 |
| 20.0 | 500 |
| 40.0 | 1000 |
| 80.0 | 2000 |
| 160.0 | 4000 |

Test compounds: 12,500, 25,000, 50,000, 100,000, 200,000 and 400,000 pg/25 μL. (4*10–5M/25 μL=400,000 pg/25 μL)

4. Dilution of VDR:
1 μl stock VDR in 2.5 ml $TEDK_{300}$/Gelatin solution (500 μ/tube), (keep on ice)

(iii) Procedure
1. Reaction Setup
Label tubes according to the following chart, each in triplicate:

| No VDR Control | No VD3 Control | Standard | Test Compounds |
| --- | --- | --- | --- |
| Add 25 μL ethanol | Add 25 μL ethanol | Add 25 μL of each standard (in each concentration) | Add 25 μL of each sample (in each concentration) |
| Add 500 μL TEDK300/gelatin solution | Add 500 μL VDR working solution | Add 500 μL VDR working solution | Add 500 μL VDR working solution |

Mixed all tubes via vortex and incubated at room temperature for 1 hour. Added 10 μL of 3H-1,25$(OH)_2D_3$ Working Dilution, mixed by vortex and incubated at room temperature for 1 hour 2. Sample processing
Thirty minutes before addition, put Charcoal/Dextran Solution on ice with continuous mixing. Added 100 μL of Charcoal/Dextran Solution to each tube, mixed well and incubated on ice for 30 minutes. Centrifuged @ 2000 rpm for 10 minutes at 4° C.

3. Counting
Pipetted 100 μL of the upper, aqueous phase to a 24 well scintillation counting plate and added 600 μL scintillation fluid per well, covered and mixed well. Counted the plate using a scintillation counter for 5 min/sample.

(iv) Calculations:
The amount of 1,25$(OH)_2D_3$ to displace 50 percent $[^3H]$-1,25$(OH)_2D_3$ from VDR was calculated as $B_{50}$ for 1,25

(OH)$_2$ D$_3$. The VDR binding of other compounds was calculated as B$_{50}$ relative to a value of 1 for 1,25(OH)$_2$D$_3$.

Serial Dilution of 1,25(OH)D$_3$

| Concentration (pg/25 µl) | Final concentration M | 10$^{-5}$ M (µl) | Ethanol (µl) |
|---|---|---|---|
| 4,000 | 2 × 10$^{-8}$ | 6 | 144 |
| 2,000 | 10$^{-8}$ | 70 | 70 |
| 1,000 | 5 × 10$^{-9}$ | 70 | 70 |
| 500 | 2.5 × 10$^{-9}$ | 70 | 70 |
| 250 | 1.25 × 10$^{-9}$ | 70 | 70 |
| 125 | 6.25 × 10$^{-10}$ | 70 | 70 |

Serial Dilution of Test Compounds

| Concentration (pg/50 ul) | Final concentration M | 10$^{-3}$ M (µl) | Ethanol (µl) |
|---|---|---|---|
| 400,000 | 2 × 10$^{-6}$ | 6 | 144 |
| 200,000 | 10$^{-6}$ | 70 | 70 |
| 10,000 | 5 × 10$^{-7}$ | 70 | 70 |
| 5,000 | 2.5 × 10$^{-7}$ | 70 | 70 |
| 25,000 | 1.25 × 10$^{-7}$ | 70 | 70 |
| 12,500 | 6.25 × 10$^{-8}$ | 70 | 70 |

Figure 2:
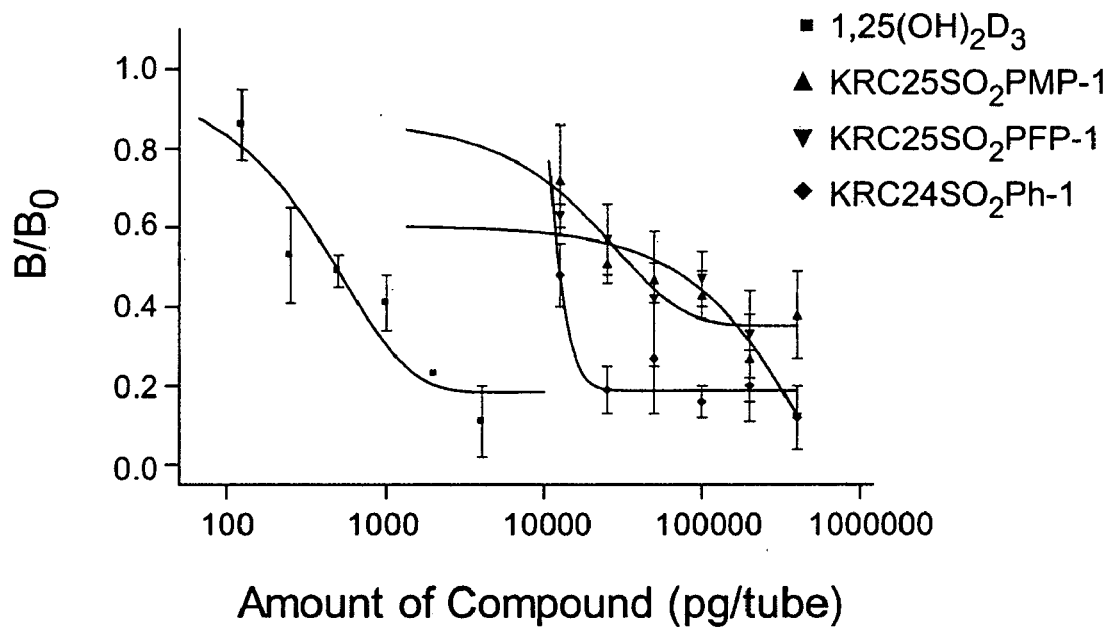
FIG. 2 is a graph showing the binding of compound I(a) (indicated as KRC24SO₂Ph-1) compared to 1α,25-dihydroxy vitamin D₃ at the vitamin D receptor.

(v) Results:
See Table 1 and FIG. 2.

(vi) References:
1. Ross T K, Prahl J M, DeLuka H. Overproduction of rat 1,25-dihydroxy vitamin D$_3$ receptor in insect cells using the baculovirus expression system. (1991) Proc Natl Acd Sci USA 88:6555–6559
2. Wecksler W R, Norman A W. An hydroxylapatite batch assay for the quantitation of 1 alpha, 25-dihydroxy vitamin D$_3$-receptor complexes (1979) Anal Biochem 92:314–323

Example 29

Transcriptional Activity Assay (A) Reagent and material:
pSG5-hVDR$^{1/3}$ from Drs. Mark Haussler and Kerr Whitfield, (University of Arizona,Tucson, Az.); hVDR$^{1/3}$ DNA inserted into the EcoRI site of pSG5vector (CT4)$^4$TKGH from Drs. Mark Haussler and Kerr Whitfield, (University of Arizona,Tucson, Az.); Four copies of the CT4 synthetic rat osteocalcin VDRE ligated and annealed into pTKGH vector which has a thymidine promoter linked to the human GH gene.
   hGH ELISA kit. Boehringer Mannheim
   Fugene 6 transfection reagent
   COS-1 cells
   DMEM medium and DMEM medium+10%FCS
   1α,25(OH)$_2$D$_3$ and test compounds (B) Transfection:
1. Subculture COS cells into 24-well plate (5,000 cell/well) one day before transfection.
2. Cocktail preparation.
   (1) To a sterile tube, add serum-free medium (100 µl per well), then add FuGene 6 Reagent (0.6 µl per well). Tap gently to mix. Add FuGene 6 Reagent directly to medium, do not allow undiluted Fugene 6 Reagent to come in contact with plastic surfaces other than the pipette tip.
   (2) Add DNA solution (pSG5-hVDRI/3 and (CT4)$^4$TKGH vectors) (0.1 µg each per well) to the prediluted FuGene 6 Reagent.
   (3) Gently tap the tube to mix the contents. Do not vortex. Incubate for 15 min at room temperature (no more than 45 min).
3. Remove the medium and replaced with 0.4 ml fresh medium
4. Add the 100µl cocktail to each well in drop-wise manner.

(C) Treatment of transfected cells with different concentrations of 1α,25(OH)$_2$D$_3$ and test compounds:
30 min to 1 hour after transfection, 1α,25(OH)$_2$D$_3$ (as control) and test compounds are added to the medium in 20 µl medium. The concentration range for 1α,25(OH)$_2$D$_3$ is 10$^{-10}$ to 10$^{-8}$ M (10$^{-10}$, 3×10$^{-9}$, 10$^{-9}$, 3×10$^{-8}$, 10$^{-8}$ M) and for test compounds is from 3×10$^{-9}$M to 10$^{-7}$M (3×10$^{-9}$, 10$^{-9}$, 3×10$^{-8}$, 10$^{-8}$, 3×10$^{-8}$, 10$^{-7}$ M). Incubate cells for 24 hours at 37° C. in humidified atmosphere plus 5% CO$_2$.

(D) Measurement of GH content in medium:
After 24 hour incubation, add 200 µL diluted aliquots of medium (dilution of 20–50 times) for human GH determination. Measure GH content according to instructions of hGH ELISA kit.

Figure 3:
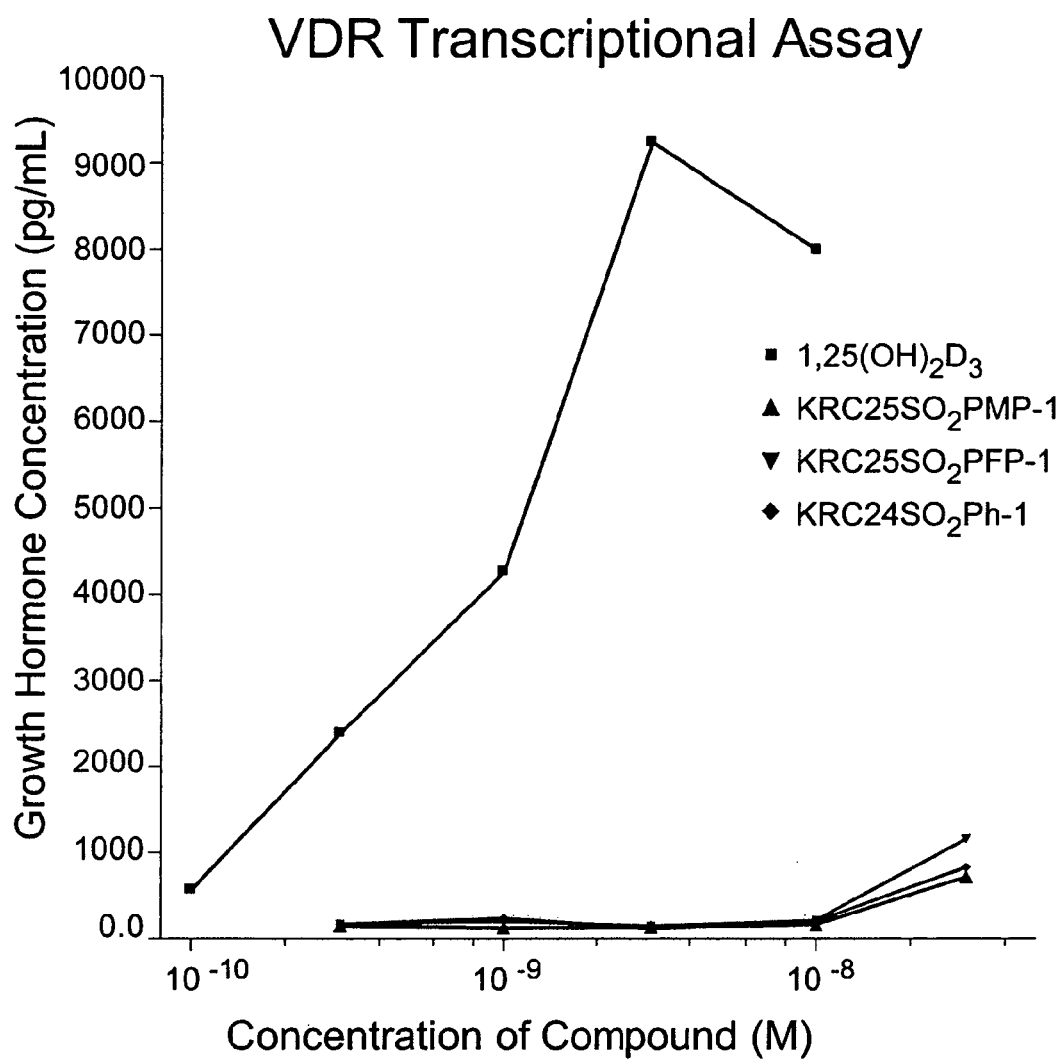
FIG. 3 is a graph showing the activity of compound I(a) (indicated as KRC24SO₂Ph-1) in the vitamin D transcription assay compared to 1α,25-dihydroxy vitamin D₃.

(E) Results:
See FIG. 3 and Table 1.

(F) References
Hashimoto Y, Ikeda I, Ikeda M, Takahashi Y, Hosaka M, Uchida H, Kono N, Fukui H, Makino T, Honjo M. Construction of a specific and sensitive sandwich enzyme immunoassay for 20 KD human growth hormone (1998) J Immunol Methods 221:77–85

Jone G, Byford V, Makin H L J, Kremer R, Rice R H, deGraffenried L A, Knutson J C, Bishop C W. Anti-proliferative activity and target cell catabolism of the vitamin D analogue 1 alpha, 24(OH)2D 2 in normal and immortalized human epidermal cells (1996) Biochem Pharmacol 52:133–140

Example 30

DBP Binding Assay (Human Plasma)

(A) Reagents:
  1. Tris-HCl buffer:
  22.50 g Tris-HCl in 500 ml H$_2$O
  2. 13.25 g Tris-base in 500 ml H$_2$O
  Stored at 4 C
  3. Dextran-T70 (Mol 70,000) Pharmacia
  4. Charcoal (carbon decolorizing neutral, norit) Fisher
  5. DBP (vitamin D binding protein) (human plasma)
  6. [$^3$H ] 25(OH)D$_3$
  7. Gelatin (G-2625 Sigma)

(B) Reagent preparation:
  1. Tris buffer
  Mix equal volume of two Tris buffer and pH to 8.6.
  2. Dextran coated charcoal solution
    (1) preparation of charcoal solution

| | |
|---|---|
| Norit decolorizing neutral charcoal | 2.0 g |
| Tris buffer | 150 mL |

Stirring
(2) preparation of dextran solution
Dextran T—70 0.2 g
Tris buffer 50 ml
(3) preparation of dextran coated charcoal solution
Slowly drip the dextran solution into charcoal solution with stirring.
Keep in refrigerate overnight.
Thirty minute before use, keep it on ice with continuous mixing.
This solution can be kept in 4 C for 2 months.
3. Tris buffer/Gelatin solution
250 mg swine gelatin
50 ml Tris buffer
heating, stirring and cooling on ice.
Prepared just before use.
4. DBP solution
Human plasma is diluted to 1:5000 with Tris buffer/gelatin solution
5. Dilution of Standard 25(OH)$D_3$
Stock 10,000 pg/50 μl
Diluted to 0, 62.5, 125, 250, 500, 750, 1000, 10,000 pg/50 μl with 100% ethanol
6. Dilution of Standard 1α,25(OH)$_2$$D_3$
Stock 200,000 pg/50 μL (10–5 M/50 μl)
Diluted to 6,250; 12,500; 25,000; 50,000; 100,000; 200,000 pg/50 μl with 100% ethanol
7. Dilution of test compounds
Stock 200,000 pg/50 μl ($10^{-3}$ M)
Diluted to 12,500; 25,000; 50,000; 100,000; 200,000 and 400,000 pg/50 μl with
100% ethanol
8. [$^3$H-26,27]-25(OH)$_2$$D_3$ solution
The stock solution is diluted in Tris buffer, 20,000 CPM/50 μl.

(C) Assay (E) Dilution of 25(OH)$D_3$:

| Amount (mol/50 ul) | From previous steps (μl) | Ethanol (μl) |
|---|---|---|
| $2.5 \times 10^{-11}$ ($5*10^{-7}$ M) | $5*10^{-7}$ M | |
| $2.5 \times 10^{-12}$ | 40 | 360 |
| $1.875 \times 10^{-12}$ | 90 | 30 |
| $1.25 \times 10^{-12}$ | 130 | 130 |
| $6.25 \times 10^{-13}$ | 130 | 130 |
| $3.125 \times 10^{-13}$ | 130 | 130 |
| $1.5625 \times 10^{-13}$ | 130 | 130 |

(F) Dilution of 1α, 25(OH)$D_3$

| Amount (mol in 50 μl) | From previous steps (μl) | Ethanol (μl) |
|---|---|---|
| $5 \times 10^{-10}$ ($10^{-5}$ M) | | |
| $2.5 \times 10^{-10}$ | 130 | 130 |
| $1.25 \times 10^{-10}$ | 130 | 130 |
| $6.25 \times 10^{-11}$ | 130 | 130 |
| $3.215 \times 10^{-11}$ | 130 | 130 |
| $1.625 \times 10^{-11}$ | 130 | 130 |

(G) Dilution of test compounds:

| Amount (mol in 50 μl) | From previous steps (μl) | Ethanol (μl) |
|---|---|---|
| Stock ($10^{-3}$ M) | | |
| $1.0 \times 10^{-9}$ | 5 | 245 |
| $5.0 \times 10^{-10}$ | 130 | 130 |
| $2.5 \times 10^{-10}$ | 130 | 130 |
| $1.25 \times 10^{-10}$ | 130 | 130 |
| $6.25 \times 10^{-11}$ | 130 | 130 |
| $3.125 \times 10^{-11}$ | 130 | 130 |

| Label | 25(OH)$D_3$ (μl) | Test cpds (μl) | $^3$H-25(OH)$D_3$ (μl) | DBP (μl) | Supermix | Incubation (Rm T) | Charcoal dextran (μl) | On ice | Centrifuge | Counting |
|---|---|---|---|---|---|---|---|---|---|---|
| 1–3 (total) | — | — | 50 | — | 600 600 | — | — | — | — | — |
| 4–8 | — | — | 50 | 500 | — | — | — | — | — | — |
| STD 5–35 | 50 | — | 50 | — | — | 4 h | 200 | 1 hr | 2000 rpm 15 min, 4 C | 200 μl Supernatant + 600 μl Supermix scintillation fluid |
| Test 36- | — | 50 | 50 | — | | | | | | |

(D) Calculation:

The amount of 25(OH)$D_3$ to displace 50 percent [$^3$H]-25(OH)$D_3$ is calculated as $B_{50}$ for 25(OH)$D_3$ DBP binding. The DBP binding of other compounds is calculated as $B_{50}$ relative to a value of 1 for 25(OH)$D_3$.

Figure 4:
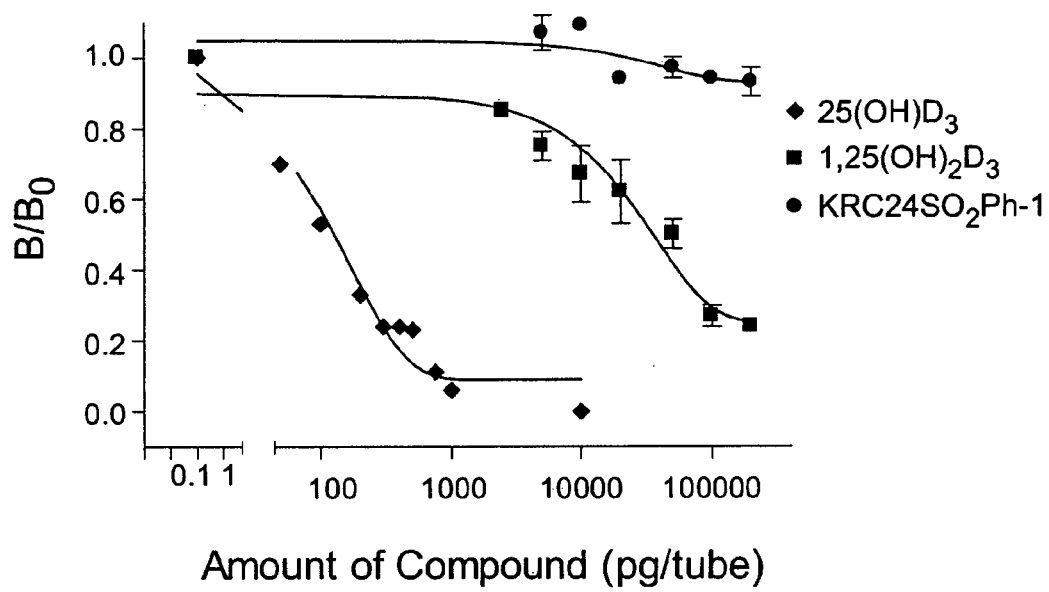
FIG. 4 is a graph showing the activity of compound I(a) (indicated as KRC24SO₂Ph-1) in the DBP binding assay compared to 1α,25-dihydroxy vitamin D₃.

(H) Results:
See FIG. 4 and Table 1.

(I) References:
Bouillon R, van Baelen H, Moor P D. Comparative study of the affinity of the serum vitamin D-binding protein. (1980) J Steroid Biochem 13:1029–44.
Jones L, Byrnes B, Palma F, Segev D, Mazur E. Displacement potency of vitamin $D_2$ analogue in competitive protein-binding assay for 25-hydroxyvitamin $D_3$, 24,25- dihydroxyvitamin $D_3$ and 1,25-dihydroxyvitamin $D_3$ (1.980) J Clin Endocrinol Metab 15 50:773–775

Example 31

Calcium Excretion

Figure 5:
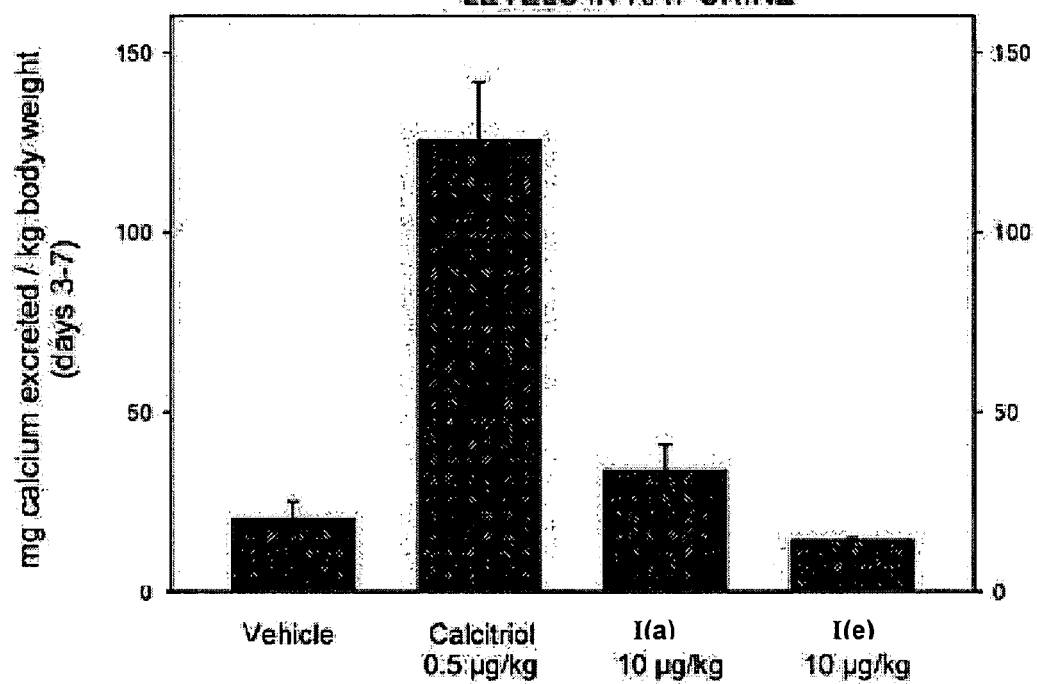
FIG. 5 is a bar graph showing the effects of compounds I(a) and I(e) on urinary calcium excretion in rats. Values are mean±SE from three animals in each group.

Compounds I(a) and I(e) were tested for their effect on calcium excretion and weight gain in rats using a protocol described in Posner et al. *J. Med. Chem.* 41, 3008–3014, 1998. In brief, the animals were treated with 0.5–10 µg/kg body weight of test compound po for 7 consecutive days and urinary excretion of calcium was measured during days 3–7. As shown in FIG. 5, compounds I(a) and I(e) produced no statistically significant urinary calcium elevation above control even at a 20-fold higher dose that calcitriol. Compound I(u) was also tested and found to be strongly non-calcemic.

Example 32

Keratinocyte Proliferation

Compound I(y) was assayed in vitro for antiproliferative activity in murine keratinocytes using a standard protocol (Posner, G. H. et al. J. med. Chem. 1992, 35, 3280–3287). Compound I(y) showed strong cell anti-proliferative activity as compared to calcitriol.

Example 33

Human Epidermal Keratinocyte Prolferation Assay (HEK) Assay (i) Material and reagents
  Normal HEK cells (Cambrex, Walkersville, Md.)
  Bullet kit KGM-Ca media (Cambrex, Walkersville, Md.)
  Reagent pack (Cambrex, Walkersville, Md.)
  Calcium chloride (Cambrex, Walkersville, Md.)
  25 $cm^2$ tissue culture flasks
  96-well tissue culture plates
  [$^3$H]-thymidine (Perkin Elmer, Boston, Mass.)
  calcitriol (1 mM) reconstituted in isopropanol (Sigma, St. Louis, Mo.)
  96-well filter plates
  scintillation fluid
  scintillation counter
  Tomtec cell harvester (Tomtec, Hamden, Conn.)

(ii) Reagent Preparation
  1. HEK cell media
  Supplemented KGM media with additional reagents provided in the bullet kit as per supplier's instructions. Added calcium chloride to final concentration of 0.3 mM.
  2. Calcitriol dilutions

| Stock: Calcitriol (1 mM) | | | | |
|---|---|---|---|---|
| Concentration (final) | from previous step (µl) | KGM media (µl) | Isopropanol (µl) | Concentration (actual) |
| $10^{-6}$ M | 8 of stock | 992 | 12 | $8 \times 10^{-6}$ M |
| $10^{-7}$ M | 100 | 882 | 18 | $8 \times 10^{-7}$ M |
| $10^{-8}$ M | 100 | 882 | 18 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-10}$ M |
| $10^{-11}$ M | 100 | 882 | 18 | $8 \times 10^{-11}$ M |

3. Substrate dilutions

| Stock: substrate (0.1 mM) | | | | |
|---|---|---|---|---|
| Concentration (final) | from previous step (µl) | KGM media (µl) | Isopropanol (µl) | Concentration (actual) |
| $10^{-7}$ M | 8 of stock | 992 | 12 | $8 \times 10^{-6}$ M |
| $5 \times 10^{-8}$ M | 500 | 490 | 10 | $8 \times 10^{-7}$ M |
| $10^{-8}$ M | 200 | 784 | 16 | $8 \times 10^{-8}$ M |
| $10^{-9}$ M | 100 | 882 | 18 | $8 \times 10^{-9}$ M |
| $10^{-10}$ M | 100 | 882 | 18 | $8 \times 10^{-11}$ M |

Figure 6:
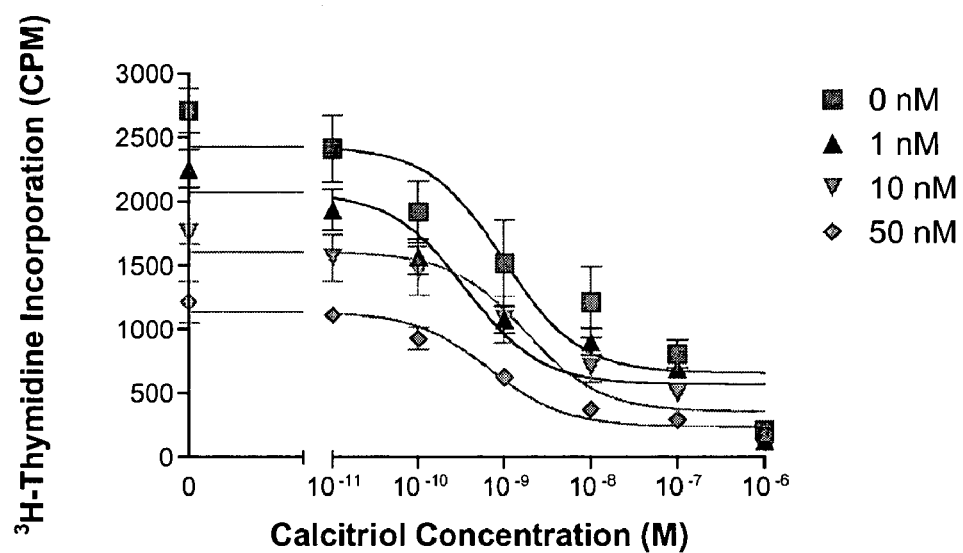
FIG. 6 is a graph showing that compound I(a) and calcitriol act to inhibit the proliferation of normal human epidermal keratinocytes (NHEK). NHEK were treated with specified concentrations of calcitriol and compound I(a) for three days. Cells were then incubated with [³H]-thymidine for 18 h at 37° C. in a humidified atmosphere containing 5% CO₂. Plates were harvested and radioactivity measured. Dose response curves in the absence of I(a), 1 nM I(a), 10 nM I(a) and 50 nM I(a) are shown.
Figure 7:
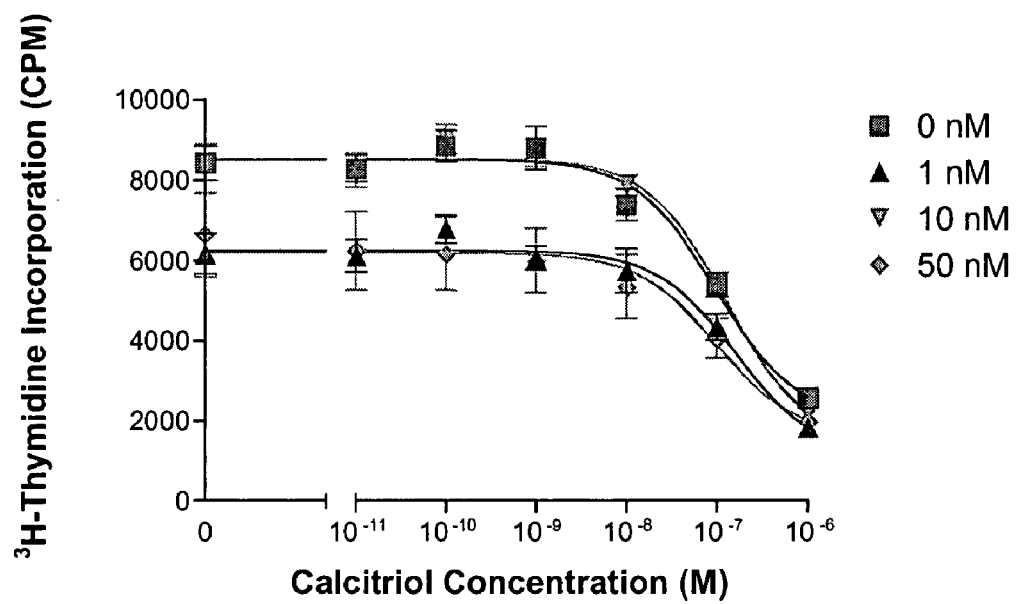
FIG. 7 is a graph showing that compound I(i) and calcitriol act to inhibit the proliferation of normal human epidermal keratinocytes (NHEK). NHEK were treated with specified concentrations of calcitriol and compound I(i) for three days. Cells were then incubated with [³H]-thymidine for 18 h at 37° C. in a humidified atmosphere containing 5% CO₂. Plates were harvested and radioactivity measured. Dose response curves in the absence of I(i), 1 nM I(i), 10 nM I(i) and 50 nM I(i) are shown.
Figure 8:
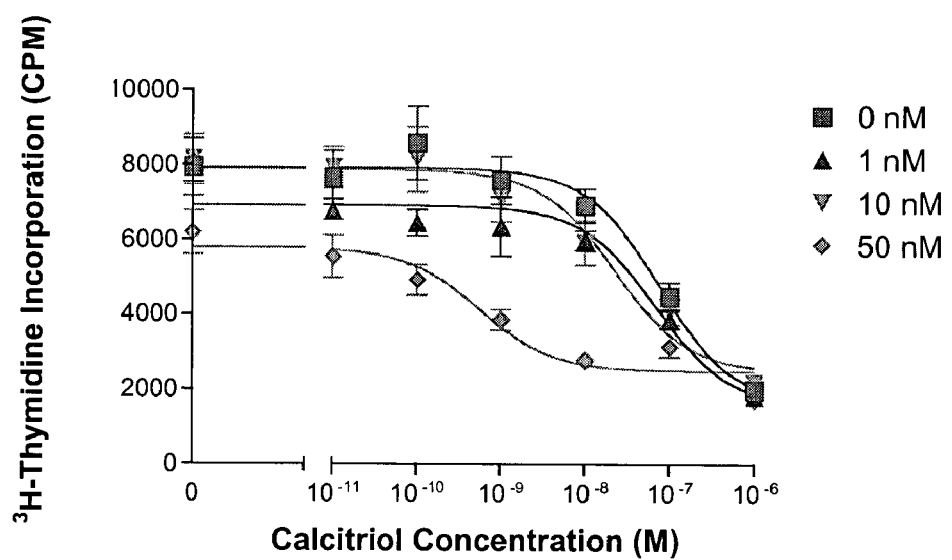
FIG. 8 is a graph showing that compound I(cc) and calcitriol act to inhibit the proliferation of normal human epidermal keratinocytes (NHEK). NHEK were treated with specified concentrations of calcitriol and compound I(cc) for three days. Cells were then incubated with [³H]-thymidine for 18 h at 37° C. in a humidified atmosphere containing 5% CO₂. Plates were harvested and radioactivity measured. Dose response curves in the absence of I(cc), 1 nM I(cc), 10 nM I(cc) and 50 nM I(cc) are shown

(iii) Procedure:
  1. Cell culture
  Thawed one vial of HEK cells containing at least 500 K, and divided into 5 25 $cm^2$ flasks with 5 ml HEK cell media. 24 h later, removed media and replenished with 5 ml fresh media. Changed media again 48 h later.
  2. Preparation of cell suspension
  On the day of the assay, washed the monolayer of HEK cells once with 1×PBS buffer (provided in reagent pack) and then trypsinized for 5 min at 37 ° C. Added trypsin neutralizing solution (provided in reagent pack). Collected cells into tube, centrifuged cells (500× g, 5 min) and resuspended in HEK cell media. Counted cells and adjusted density to 150,000 cells/ml. Diluted cells further 1:30 with HEK cell media.
  2. Cell plating
  Added 150 µl of cell suspension to appropriately labelled wells of a 96-well plate. Incubated plate for 48 h at 37° C. in a humidified atmosphere containing 5% $CO_2$ for adherence of cells to wells.
  3. Compound addition
  Added 25 µl of calcitriol ($10^{-6}$ to $10^{-11}$ M, final) and added 25 µl of substrate ($10^{-7}$ to $10^{-10}$ M, final) and incubated for 32 hours at 37° C. in a humidified atmosphere containing 5% $CO_2$.
  4. Cell harvesting and counting
  Added 0.2 µCi/well of [$^3$H]-thymidine in 20 µl of HEK cell media to each well. Incubated plates for 18 h at 37° C. in a humidified atmosphere containing 5% $CO_2$. Aspirated media and washed with 1×PBS. Trypsinize cells for 30 min at 37° C. in a humidified atmosphere containing 5% $CO_2$. Harvested cells onto filter plates using Tomtec cell harvester as per manufacturer's instructions. Added 25 µl scintillation fluid per well. Measured radioactivity using a scintillation counter. All values were normalized for background.
  5. Results:
  Graphs showing results for compounds I(a), I(i), and I(cc) are shown in FIGS. 6–8 respectfully

Example 34

[$^3$H]-thymidine Proliferation Assay with MCF-7 Cells (i) Materials and Methods:
MCF-7 cells (ATCC)
MEM supplemented with sodium pyruvate, non-essential amino acids, bovine insulin, gentamycin and 10% Fetal bovine serum (growth media)
RPMI1640 supplemented with tri-iodothyronine, hydrocortisone, transferin, bovine insulin and 5% Fetal bovine serum (proliferation media)
1α,25(OH)$_2$D$_3$ 1 mM reconstituted in isopropanol
substrates (1 mM) reconstituted in isopropanol
Trypsin:EDTA solution
1×PBS
75 cm$^2$ tissue culture flasks
96 well tissue culture plates
Liquid scintillation fluid
96 well filter plate (Millipore)

Figure 9:
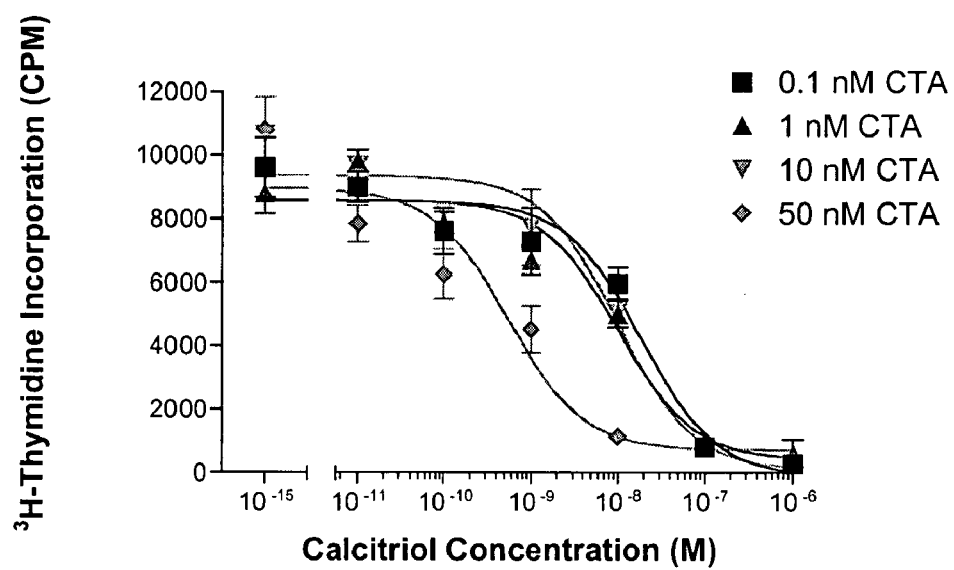
FIG. 9 is a graph showing that compound I(a) and calcitriol act to inhibit the proliferation of MCF-7 cells. MCF-7 cells were treated with specified concentrations of calcitriol and compound I(a) for three days. Cells were then incubated with [³H]-thymidine for 18 h at 37° C. in a humidified atmosphere containing 5% CO₂. Plates were harvested and radioactivity measured. Dose response curves in the presence of 0.1 nM I(a), 1 nM I(a), 10 nM I(a) and 50 nM I(a) are shown.
Figure 10:
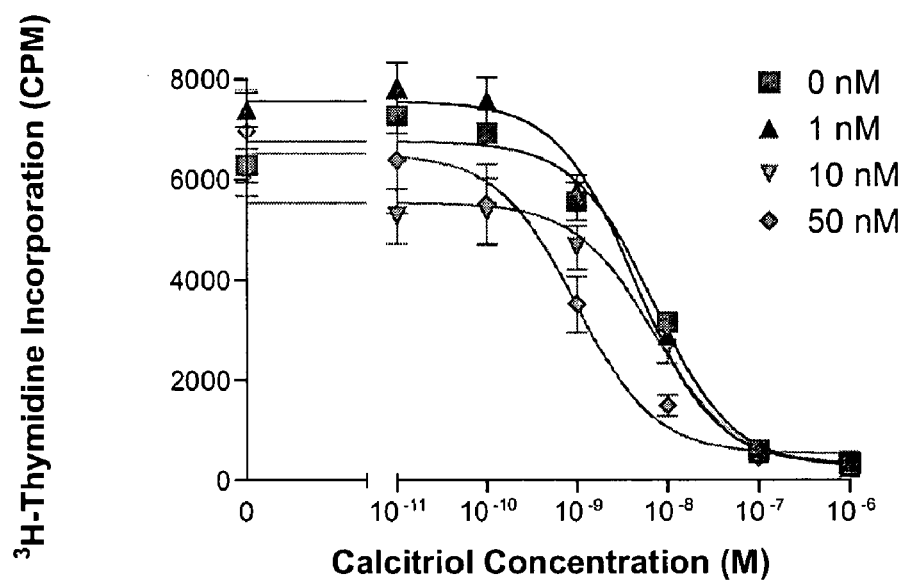
FIG. 10 is a graph showing that compound I(i) and calcitriol act to inhibit the proliferation of MCF-7 cells. MCF-7 cells were treated with specified concentrations of calcitriol and compound I(i) for three days. Cells were then incubated with [3H]-thymidine for 18 h at 37° C. in a humidified atmosphere containing 5% CO₂. Plates were harvested and radioactivity measured. Dose response curves in the absence of I(i), 1 nM I(i), 10 nM I(i) and 50 nM I(i) are shown.
Figure 11:
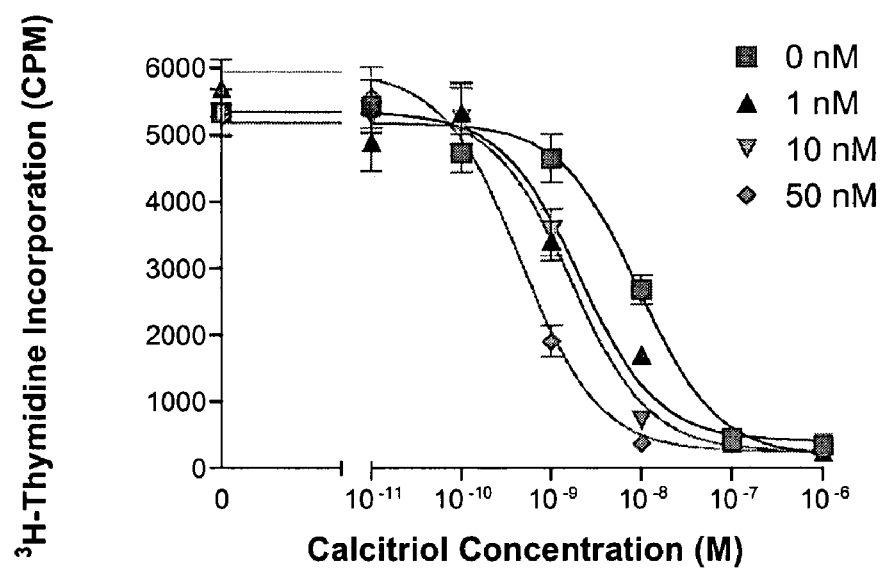
FIG. 11 is a graph showing that compound I(cc) and calcitriol act to inhibit the proliferation of MCF-7 cells. MCF-7 cells were treated with specified concentrations of calcitriol and compound I(cc) for three days. Cells were then incubated with [$^3$H]-thymidine for 18 h at 37° C. in a humidified atmosphere containing 5% $CO_2$. Plates were harvested and radioactivity measured. Dose response curves in the absence of I(cc), 1 nM I(cc), 10 nM I(cc) and 50 nM I(cc) are shown.

(ii) Procedure:
1. Preparation of cell suspension
    When MCF-7 cells were 70–80% confluent, aspirated growth media. Washed the cells with 1×PBS. Trypsinized with trypsin-EDTA from the plate, collected cells from the tissue culture flask, centrifuged (500×g, 5 min) and resuspended in growth media.
2. Cell plating.
    Counted the cells and adjusted the cell density to 25,000/ml. Added 200 μl per well in a 96 well plate. Incubated plate for 24 h at 37° C. in a humidified atmosphere plus 5% CO$_2$. Aspirated used media and replaced with 150 μl per well with proliferation media.
3. Substrate addition.
    Added 25 μl of 1α,25(OH)$_2$D$_3$ (final concentration $10^{-6}$ M, $10^{-7}$ M, $10^{-8}$ M, $10^{-9}$ M, $10^{-10}$ M, $10^{-11}$ M) into each designated well. Added 25 μl of substrate (final concentration $10^{-7}$ M, $5\times10^{-8}$ M, $10^{-8}$ M or $10^{-9}$M) into each designated well.
Incubated plates for 3 days at 37° C. in a humidified atmosphere plus 5% CO$_2$.
4. $^3$H-Thymidine incorporation.
    Added $^3$H-thymidine at 0.02 μCi per well and incubated at 37° C. in a humidified atmosphere plus 5% CO$_2$ for 6 h.
5. Plate Harvesting.
    Aspirated all media and washed cells with 1×PBS. Trypsinized cells for 30 min at 37° C. in a humidified atmosphere plus 5% CO$_2$. Harvested cells onto a 96 well filter plate (Millipore) using a Tomtec Cell Harvestor, according to manufacturers instructions.
6. Scintillation Counting.
    Added 25 μl of scintillation fluid per well. Counted the plate using a scintillation counter.
7. Results.
    Graphs showing results for compounds I(a), I(i) and I(cc) are shown in FIGS. 9–11 respectfully.

Example 35

Proposed Topical Composition Containing a Compound of the Invention

Dissolve a compound of the invention (1 mg) in 1 g of almond oil. To this solution add mineral oil (40 g) and self emulsifying beeswax (20 g). Heat the mixture to liquefy, and add hot water (40 mL) and stir the mixture well to provide a cream containing approximately 10 μg of a compound of the invention per gram of cream.

Example 36

Proposed Cream Containing 50 μg of a Compound of the Invention/g

| Compound of the invention | 50 mg |
| --- | --- |
| Cetomacrogol 1000 | 25 g |
| Cetostearyl alcohol | 75 g |
| Chloroallylhexaminium chloride | 0.5 g |
| Glycerol | 30 g |
| Disodium hydrogenphosphate | 2 g |
| Sodium dihydrogenphosphate | 0.1 g |
| Liquid paraffin | 60 g |
| Polyoxyethylene stearylether | 12 g |
| White petrolatum | 160 g |
| Purified water up to | 1000 g |

Dissolve a compound of the invention in a solution of glycerol, disodium hydrogenphosphate, sodium dihydrogenphosphate and polyoxyethylene stearylether dissolved in water. Mix with the melted cetomacrogol 1000, liquid paraffin, cetostearyl alcohol and white petrolatum. Homogenize the emulsion and cool. Dissolve chloroallylhexaminium chloride in part of the water and mix until homogeneous with the emulsion. Fill the cream in aluminium tubes.

Example 37

Proposed Cream Containing 100 μg of a Compound of the Invention/g

| Compound of the invention | 100 mg |
| --- | --- |
| Cetomacrogol 1000 | 30 g |
| Cetostearyl alcohol | 60 g |
| Chloroallylhexaminium chloride | 0.5 g |
| Propylenglycol | 30 g |
| Disodium hydrogenphosphate | 2 g |
| Sodium dihydrogenphosphate | 0.1 g |
| Liquid paraffin | 50 g |
| White petrolatum | 170 g |
| Purified water up to | 1000 g |

Melt cetomacrogol 1000, cetostearyl alcohol, liquid paraffin and white petrolatum at 75° C. Dissolve propylenglycol in water at 75° C. and mix the solution with the fatty phase. Homogenize the emulsion and cool to 30° C. Mill the compound of the invention to particle size below 5 μm and suspend in an aqueous solution of disodium hydrogenphosphate, sodium dihydrogenphosphate and chloroallylhexaminium chloride. Add the suspension to the emulsion and fill the cream in tubes.

Example 38

Proposed Lotion Containing 50 μg of a Compound of the Invention/g

| Compound of the invention | 50 mg |
| --- | --- |
| Absolute alcohol | 400 g |
| Hydroxypropylcellulose | 1 g |

-continued

| Menthol | 1 g |
| Sodium citrate | 1 g |
| Propylenglycol | 40 g |
| Purified water up to | 1000 ml |

Dissolve hydroxypropylcellulose, sodium citrate and propylenglycol in water. Mix with a solution of a compound of the invention and menthol in absolute alcohol. Fill the lotion in polyethylen plastic bottles.

Example 39

Proposed Capsules Containing a Compound of the Invention

A compound of the invention is suspended in arachis oil to a final concentration of 5 µg/ml oil. Mix together, with heating, 10 parts by weight of gelatine, 5 parts by weight of glycerine, 0.08 parts by weight potassium sorbate, and 14 parts by weight distilled water and form into soft gelatine capsules. Then fill each capsule with 100 µl of compound in oil suspension, such that each capsule contains 0.5 µg of the compound.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

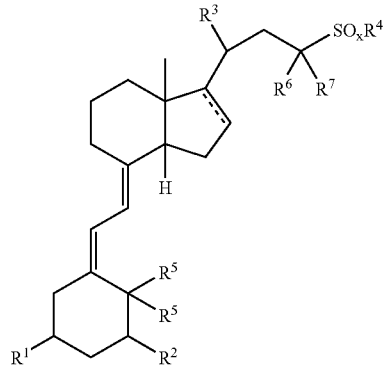

wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, nitro, $NHC_{1-4}$alkyl, $N(C_{1-4}$alkyl$)(C_{1-4}$alkyl$)$, CN, C(O)OH, $C(O)OC_{1-4}$alkyl, $C(O)NHC_{1-4}$alkyl, CH=N—$OC_{1-4}$alkyl, $NHC(O)C_{1-4}$alkyl, $OC(O)C_{1-4}$alkyl, $SOC_{1-4}$alkyl, $SO_2C_{1-4}$alkyl, $SO_2NHC_{1-4}$alkyl and $SO_2NH_2$;
$R^5$ are either both H or together form =$CH_2$;
$R^6$ and $R^7$ are both H or are taken together to form a $C_{3-6}$cyloalkyl ring;
x is 0–2; and
⁃⁃⁃⁃⁃ represents a single or a double bond.

TABLE 1

Summary of Biological Activity for Compounds of the Invention

| Cpd # | CYP24 IC$_{50}$ (nM) (HPK1A ras cells) | CYP24 IC$_{50}$ (nM) (V79-CYP24 cells) | CYP27B1 IC$_{50}$ (nM) (COS-1 cells) | CYP27B1 IC$_{50}$ (nM) (HEK cells) | CY27A1 IC$_{50}$ (nM) | VDR Binding B50 (nM) | Transcription (nM) | DBP Binding B50 (nM) |
|---|---|---|---|---|---|---|---|---|
| I(a) | 28 | | >10,000 | >1000 | >10,000 | >2000 | 30 | >1000 |
| I(e) | 94 | | >1000 | | | 1301 | | |
| I(g) | 212 | | >1000 | | | | | |
| I(i) | 92 | | >1000 | | | 536 | | |
| I(v) | 219 | | >10,000 | | | 534 | | |
| I(w) | 90 | | 9200 | | >1000 | 2000 | | |
| I(u) | | 160 | | | | >2000 | | |
| I(y) | 146 | | >10,000 | | | | | |
| I(cc) | | 27 | | | | >2000 | | |
| I(gg) | 467 | | 8460 | | | | | |
| I(jj) | | 188 | | | >1000 | | | |
| I(nn) | | 343 | | | >1000 | | | |
| I(oo) | | 171 | | | >1000 | | | |

We claim:

1. A compound of Formula I, and pharmaceutically acceptable salts, hydrates, solvates and prodrugs thereof:

2. The compound according to claim 1, wherein $R^1$ and $R^2$ are independently selected from the group consisting OH, $OCH_3$, and fluoro.

3. The compound according to claim 2, wherein $R^1$ and $R^2$ are both OH.

4. The compound according to claim 1, wherein $R^3$ is $CH_3$.

5. The compound according to claim 1, wherein $R^4$ is selected from the group consisting of unsubstituted and substituted phenyl, pyridyl, thienyl, furanyl and pyrrolo.

6. The compound according to claim 5, wherein $R^4$ is selected from unsubstituted or substituted phenyl.

7. The compound according to claim 1, wherein both aryl and heteroaryl are either unsubstituted or substituted with 1–3 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$, CN, C(O)OH, C(O)$OC_{1-4}$alkyl, CH=N—$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$.

8. The compound according to claim 7, wherein both aryl and heteroaryl are either unsubstituted or substituted with 1–2 groups independently selected from methyl, 3-hydroxy-3-pentyl, methoxy, OH, $CF_3$, $OCF_3$, halo, $NH_2$, $NMe_2$ and CH=N—OMe.

9. The compound according to claim 8, wherein both aryl and heteroaryl are either unsubstituted or substituted with 1–2 groups independently selected from methyl, 3-hydroxy-3-pentyl, Cl, F and CH=N—OMe.

10. The compound according to claim 6, wherein $R^4$ is selected from the group consisting of phenyl, 4-chlorophenyl, 3,4-dichloropheny, 4-fluorophenyl, 4-methylphenyl, 3,4-difluorophenyl, 4-(3-hydroxy-3-pentyl)phenyl, 4-(CH=N—OMe)phenyl, 4-methoxyphenyl, 4-trifluoromethylphenyl and 4-nitrophenyl.

11. The compound according to claim 10, wherein $R^4$ is selected from the group consisting of 4-chlorophenyl, 3,4-dichloropheny, 4-(3-hydroxy-3-pentyl)phenyl, 4-fluorophenyl and 4-methylphenyl.

12. The compound according to claim 1, wherein $R^6$ and $R^7$ are both H or are taken together to form a $C_{3-4}$cyloalkyl ring.

13. The compound according to claim 1, wherein x is 2.

14. The compound according to claim 1, wherein ----- represents a single bond.

15. A compound of Formula I, and pharmaceutically acceptable salts, hydrates, solvates and prodrugs thereof:

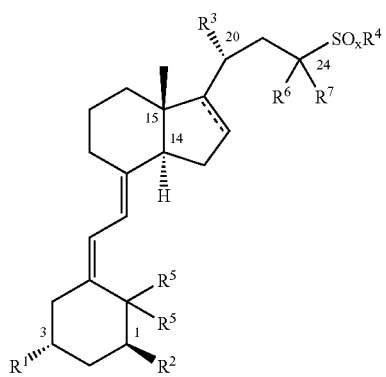

wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl; OH, $CF_3$, $OCF_3$, halo, SH, $SC_{1-4}$alkyl, $NH_2$, nitro, $NHC_{1-4}$alkyl, $N(C_{1-4}alkyl)(C_{1-4}alkyl)$, CN, C(O)OH, C(O)$OC_{1-4}$alkyl, C(O)$NHC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$;
$R^5$ are either both H or together form =$CH_2$;
$R^6$ and $R^7$ are both H or are taken together to form a $C_{3-6}$cyloalkyl ring;
x is 0–2; and
----- represents a single or a double bond.

16. A compound of Formula I, and pharmaceutically acceptable salts, hydrates, solvates and prodrugs thereof:

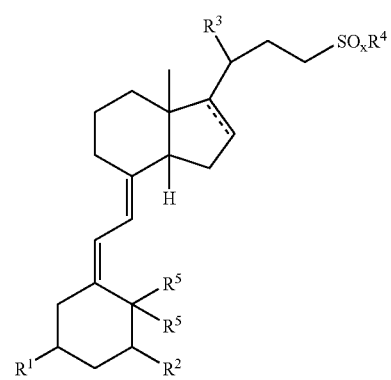

wherein
$R^1$ and $R^2$ are independently selected from the group consisting of OH, $OC_{1-4}$alkyl, and halo;
$R^3$ is $C_{1-4}$alkyl;
$R^4$ is selected from the group consisting of aryl and heteroaryl with both aryl and heteroaryl being unsubstituted or substituted with 1–5 groups independently selected from $C_{1-4}$alkyl, hydroxy-substituted $C_{1-6}$alkyl, $OC_{1-4}$alkyl, OH, $CF_3$, $OCF_3$, halo, SH, $SC_{1-4}$alkyl, $NH_2$, $NHC_{1-4}$alkyl, $N(C_{1-4}alkyl)(C_{1-4}alkyl)$, CN, C(O)OH, C(O)$OC_{1-4}$alkyl, C(O)$NHC_{1-4}$alkyl, CH=N—$OC_{1-4}$alkyl, NHC(O)$C_{1-4}$alkyl, OC(O)$C_{1-4}$alkyl, $SOC_{1-4}$alkyl, $SO_2C_{1-4}$alkyl, $SO_2NHC_{1-4}$alkyl and $SO_2NH_2$;
$R^5$ are either both H or together form =$CH_2$;
x is 0–2; and
----- represents a single or a double bond.

17. The compound according to claim 1 selected from the group consisting of:

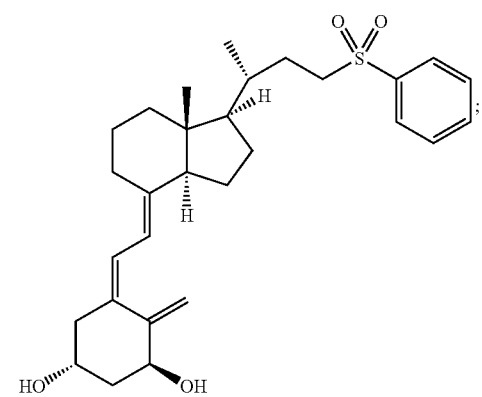
I(a)
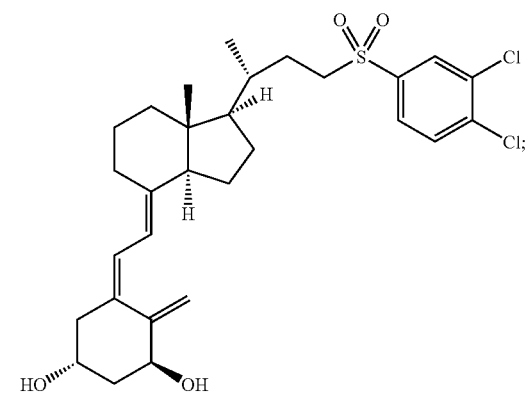
I(i)
I(c)
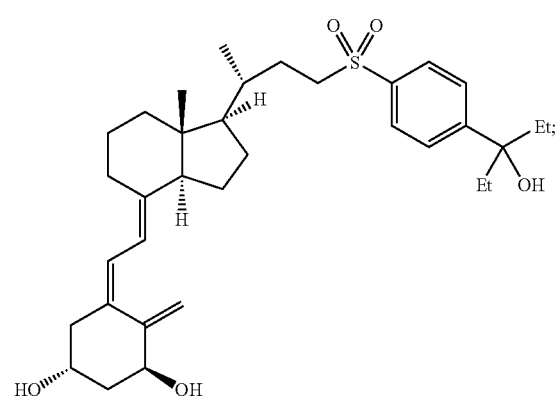
I(k)
I(e)
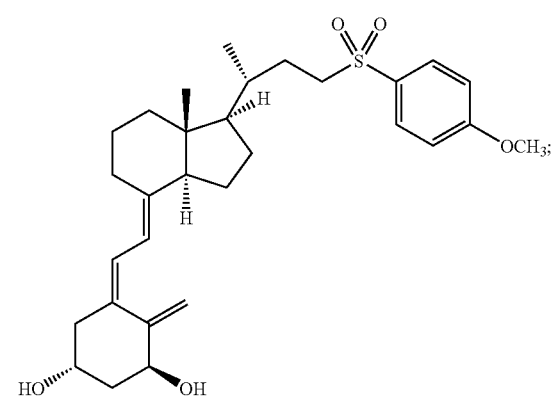
I(m)
I(g)
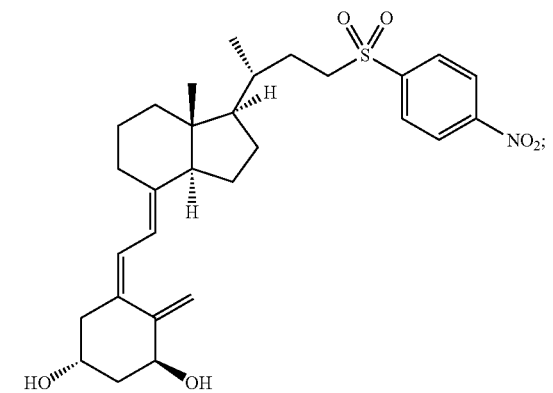
I(o)

-continued
I(q)
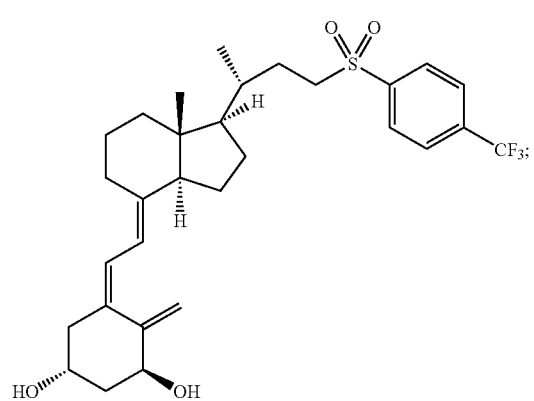
I(s)
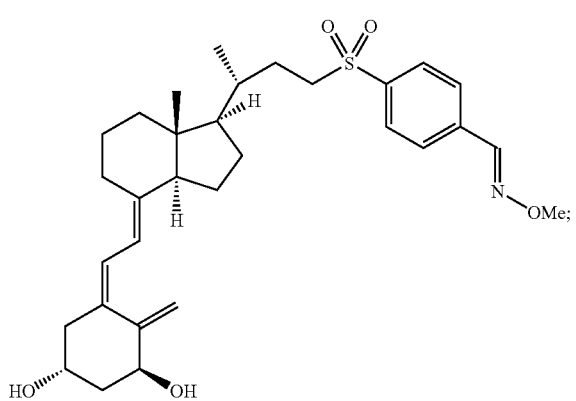
I(u)
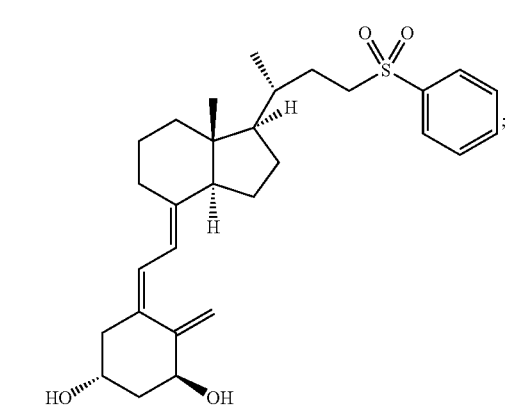
I(cc)
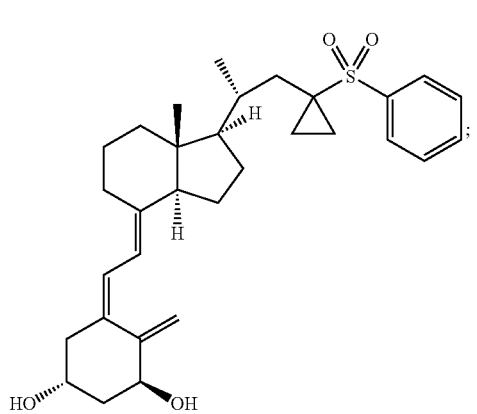
-continued
I(ee)
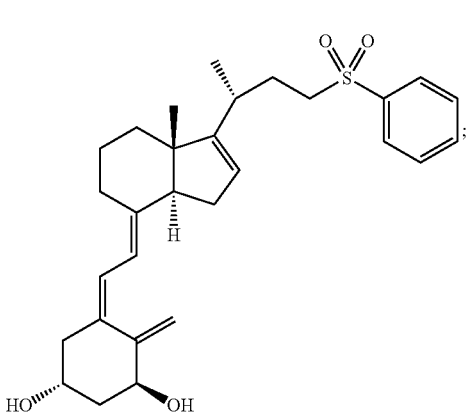
I(ii)
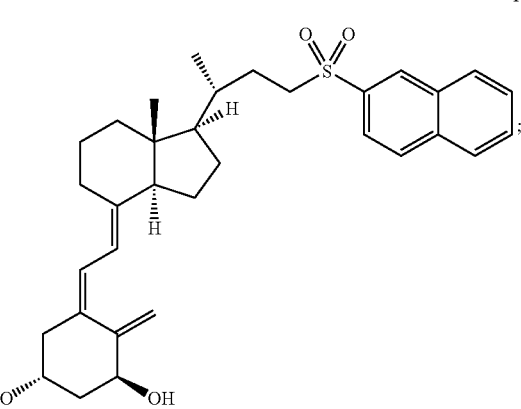
I(jj)
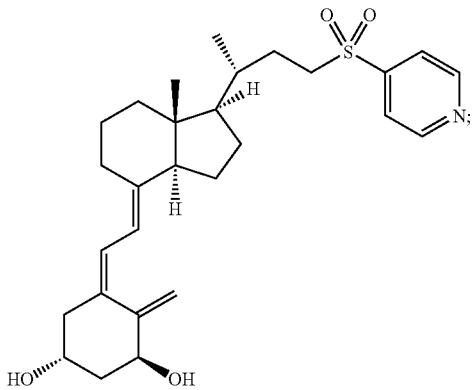

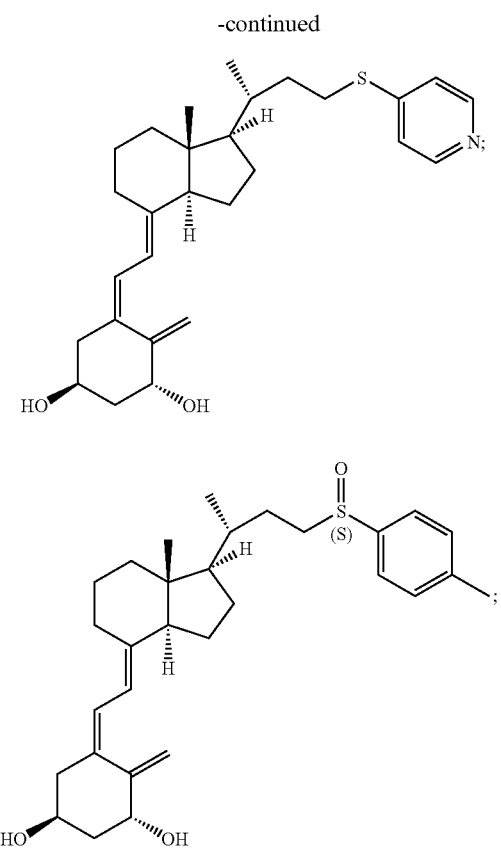

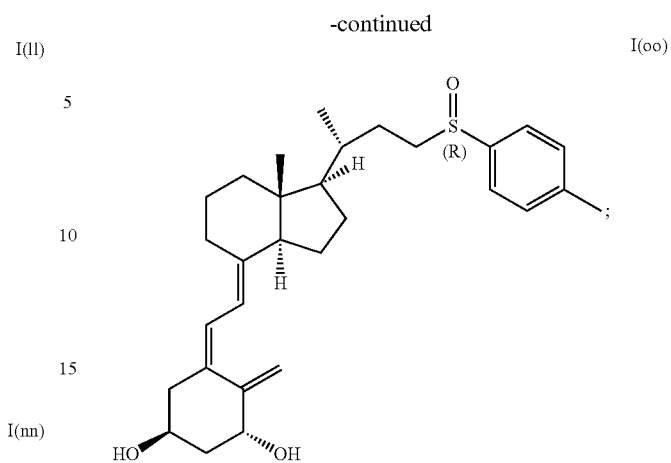

and pharmaceutically acceptable salts, hydrates, solvates and prodrugs thereof.

18. The compound according to claim 17, selected from the group consisting of I(a), I(e), I(g), I(i), I(m), I(o), I(q), I(u), J(cc), I(ee), I(jj), I(ll), I(nn) and I(oo).

19. The compound according to claim 17, selected from the group consisting of I(a), I(e), I(g), I(i), I(u), I(cc), I(ee), I(jj), I(nn) and I(oo).

20. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,166,585 B2  
APPLICATION NO. : 10/612302  
DATED : January 23, 2007  
INVENTOR(S) : Gary H. Posner et al.

Page 1 of 1

It is certified that error appears in the above-identified patent and that said Letters Patent is hereby corrected as shown below:

In the Claims:

At Column 104, line 35 "$C_{3-6}$cyloalkyl" should be -- $C_{3-6}$cycloalkyl --.

At Column 105, line 27, "3,4-dichloropheny" should be -- 3,4-dichlorophenyl --.

At Column 105, line 32-33, "3,4-dichloropheny" should be -- 3,4-dichlorophenyl --.

At Column 106, line 10, "OH, $OCF_3$" should be -- OH, $CF_3$, $OCF_3$ --.

At Column 106, line 18 "$C_{3-6}$cyloalkyl" should be -- $C_{3-6}$cycloalkyl --.

Signed and Sealed this

Fourteenth Day of August, 2007

JON W. DUDAS  
*Director of the United States Patent and Trademark Office*

UNITED STATES PATENT AND TRADEMARK OFFICE
CERTIFICATE OF CORRECTION

PATENT NO. : 7,166,585 B2  
APPLICATION NO. : 10/612302  
DATED : January 23, 2007  
INVENTOR(S) : Gary H. Posner et al.

Page 1 of 1

It is certified that error appears in the above-identified patent and that said Letters Patent is hereby corrected as shown below:

At column 18, lines 40-50, compound I(u) 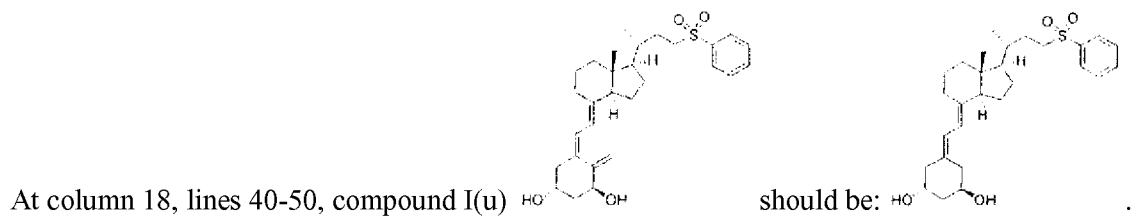 .

In Claim 17 at column 109, lines 35-50, compound I(u) 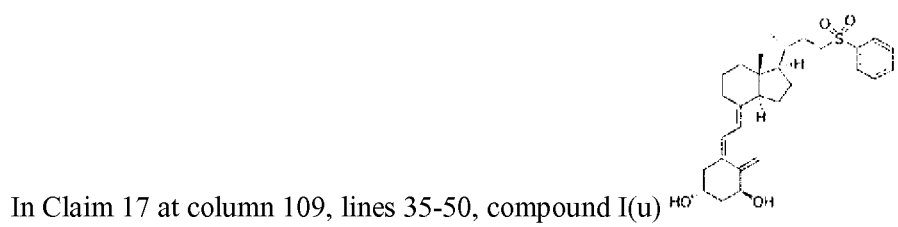

should be: .

Signed and Sealed this
Eighteenth Day of September, 2012

David J. Kappos
*Director of the United States Patent and Trademark Office*